United States Patent
Komiya et al.

(10) Patent No.: US 10,407,395 B2
(45) Date of Patent: *Sep. 10, 2019

(54) BENZIMIDAZOLE COMPOUND AND MEDICAL USE THEREOF

(71) Applicant: Sumitomo Dainippon Pharma Co., Ltd., Osaka (JP)

(72) Inventors: Masafumi Komiya, Osaka (JP); Kohei Iwamoto, Osaka (JP); Toshio Kanai, Osaka (JP); Shingo Mizushima, Osaka (JP); Keiji Adachi, Osaka (JP); Kuniko Urashima, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,185

(22) PCT Filed: Sep. 9, 2016

(86) PCT No.: PCT/JP2016/076645
§ 371 (c)(1),
(2) Date: Dec. 30, 2016

(87) PCT Pub. No.: WO2017/043636
PCT Pub. Date: Mar. 16, 2017

(65) Prior Publication Data
US 2018/0170881 A1 Jun. 21, 2018

(30) Foreign Application Priority Data
Sep. 11, 2015 (JP) .................................. 2015-179663

(51) Int. Cl.
| | |
|---|---|
| *C07D 235/08* | (2006.01) |
| *C07D 401/04* | (2006.01) |
| *C07D 401/12* | (2006.01) |
| *C07D 405/04* | (2006.01) |
| *C07D 405/06* | (2006.01) |
| *C07D 405/14* | (2006.01) |

(Continued)

(52) U.S. Cl.
CPC ............ *C07D 235/08* (2013.01); *A61P 13/00* (2018.01); *A61P 25/00* (2018.01); *A61P 25/04* (2018.01); *C07D 235/06* (2013.01); *C07D 401/04* (2013.01); *C07D 401/10* (2013.01); *C07D 401/12* (2013.01); *C07D 403/12* (2013.01); *C07D 405/04* (2013.01);

(Continued)

(58) Field of Classification Search
None
See application file for complete search history.

(56) References Cited

U.S. PATENT DOCUMENTS

| | | | |
|---|---|---|---|
| 9,688,670 B2 * | 6/2017 | Komiya | ............... C07D 403/12 |
| 2004/0010141 A1 | 1/2004 | Noe et al. | |
| 2005/0272765 A1 | 12/2005 | Feng et al. | |
| 2013/0274243 A1 | 10/2013 | Bagal et al. | |
| 2013/0296281 A1 | 11/2013 | Kyle et al. | |
| 2014/0275011 A1 | 9/2014 | Mastracchio et al. | |
| 2015/0133500 A1 | 5/2015 | Tafesse et al. | |

FOREIGN PATENT DOCUMENTS

| | | |
|---|---|---|
| JP | 2005/529895 | 10/2005 |
| JP | 2008/501714 | 1/2008 |

(Continued)

OTHER PUBLICATIONS

International Search Report and Written Opinion in Application No. PCT/JP2016/076645, dated Nov. 15, 2016.
EP Extended European Search Report in Application No. 16844497.4, dated Feb. 19, 2019, 7 pages.
Dib-Hajj et al., "The NaV1.7 sodium channel: from molecule to man," Nat. Rev. Neurosci., Jan. 2013, 14:49-62.
Hay et al., "Discovery and Optimization of Small-Molecule Ligands for the CBP/p300 Bromodomains," Journal of the American Chemical Society, Jun. 2014, 136:9308-9319.
Minett et al., "Distinct Nav1.7-dependent pain sensations require different sets of sensory and sympathetic neurons," Nat. Commun., Apr. 2012, 3:791.

*Primary Examiner* — Kamal A Saeed
(74) *Attorney, Agent, or Firm* — Fish & Richardson P.C.

(57) ABSTRACT

The present invention provides a medicament for treating a disease involving Nav 1.7 such as neuropathic pain, nociceptive pain, inflammatory pain, small-fiber neuropathy, erythromelalgia, paroxysmal extreme pain disorder, dysuria, and multiple sclerosis, which comprises a compound of formula (I):

(I)

or a pharmaceutically acceptable salt thereof, wherein $R^{1a}$, $R^{1b}$, $R^{1c}$ and $R^{1d}$ are hydrogen, halogen, cyano, $C_{1-4}$ alkyl, $C_{1-4}$ alkoxy, or the like, provided that at least one of $R^{1a}$, $R^{1b}$, $R^{1c}$ and $R^{1d}$ is $C_{6-10}$ aryl, $C_{6-10}$ aryloxy, or the like, $R^2$ and $R^3$ are hydrogen, $C_{1-6}$ alkyl, $C_{3-10}$ cycloalkyl, or the like, $R^4$ is hydrogen, $C_{1-6}$ alkyl, $C_{3-7}$ cycloalkyl, or the like, m is 1, 2 or 3, L is $CR^7R^8$, and $R^7$ and $R^8$ are hydrogen, hydroxyl, $C_{1-4}$ alkyl, $C_{1-4}$ alkoxy, or the like.

27 Claims, No Drawings

(51) Int. Cl.
- *C07D 413/14* (2006.01)
- *C07D 417/14* (2006.01)
- *C07D 403/12* (2006.01)
- *C07D 401/10* (2006.01)
- *C07D 413/10* (2006.01)
- *C07D 413/04* (2006.01)
- *C07D 235/06* (2006.01)
- *A61P 25/00* (2006.01)
- *A61P 25/04* (2006.01)
- *A61P 13/00* (2006.01)

(52) U.S. Cl.
CPC ......... *C07D 405/06* (2013.01); *C07D 405/14* (2013.01); *C07D 413/04* (2013.01); *C07D 413/10* (2013.01); *C07D 413/14* (2013.01); *C07D 417/14* (2013.01)

(56) References Cited

FOREIGN PATENT DOCUMENTS

| | | |
|---|---|---|
| JP | 2013/530180 | 7/2013 |
| JP | 2015/509110 | 3/2015 |
| WO | WO 2012/057262 | 5/2012 |
| WO | WO 2014/054635 | 4/2014 |
| WO | WO 2015/008861 | 1/2015 |
| WO | WO 2016/057834 | 4/2016 |
| WO | WO 2016/117647 | 7/2016 |
| WO | WO 2016/150971 | 9/2016 |
| WO | WO 2016/172358 | 10/2016 |

* cited by examiner

BENZIMIDAZOLE COMPOUND AND MEDICAL USE THEREOF

CROSS REFERENCE TO RELATED APPLICATIONS

This application is a U.S. National Phase under 35 U.S.C. § 371 of International Application No. PCT/JP2016/076645, filed Sep. 9, 2016, which published as WO2014/054635, and which claims priority to Japanese Application No. 2015-179663, filed Sep. 11, 2015. All of the above are hereby incorporated by reference in their entireties.

TECHNICAL FIELD

The present invention may relate to a medicament for treating or preventing a disease involving Na channel, particularly SCN9A (Nav 1.7), which comprises a novel compound having a benzimidazole skeleton or a pharmaceutically-acceptable salt thereof as an active ingredient. In more detail, it relates to a medicament for treating or preventing a disease such as neuropathic pain, nociceptive pain, inflammatory pain, small-fiber neuropathy, erythromelalgia, paroxysmal extreme pain disorder, dysuria, and multiple sclerosis.

BACKGROUND ART

Voltage-dependent Na channel a subunit that forms pore is known to include 9 kinds at present. Recently, it has been evidenced that the subunit, particularly Nav 1.7 is broadly concerned in the signal transduction of acute and chronic pain.

SCN9A (Nav 1.7) is tetrodotoxin (TTX)-sensitive Na channel localized in the peripheral sensory nerve or sympathetic nerve, which is also referred to as NENA or PN1. Physiologically, Nav 1.7 channel functions to amplify a pain signal (i.e., generate a generator potential) at the sensory nerve ending. In the field of genetic investigation, it has been getting evident that a human whose SCN9A gene mutates to result in loss-of-function shows congenital insensitivity to pain. Reversely, in patients suffering from a severe orphan disease such as erythromelalgia and paroxysmal extreme pain disorder, it is observed that SCN9A gene mutates to result in gain-of-function. Furthermore, it has been reported that approximately 30% of patients suffering from small fiber neuropathy have genetic polymorphism to enhance Nav 1.7 function (Non-Patent Literature 1). And, it is suggested that Nav 1.7 channel function is directly concerned in the hyperexcitability of DRG neuron in patients suffering from pain since the expression level and activity increase in DRG neuron of model animals suffering from chronic pain, and neuropathic pain and inflammatory pain decrease in a knockout experiment (Non-Patent Literature 2).

Patent Literature 1 discloses a benzimidazole derivative represented by the following formula (A), but the compound have 2-((4-cyclopropylpyridin-2-yl)amino)isonicotinonitrile as an essential partial structure, which is different from the compound of the present invention. And, the invention described in Patent Literature 1 is directed to a Syk tyrosine kinase inhibitor, thus Patent Literature 1 does not disclose the present invention at all.

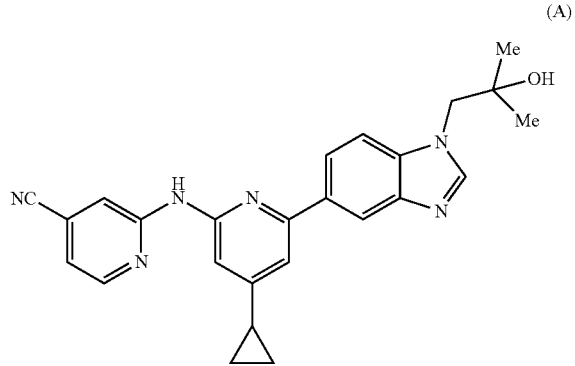 [SMILES: CC(C)(O)Cn1cnc2cc(-c3cc(C4CC4)cc(Nc4cc(C#N)ccn4)n3)ccc21]

(A)

CITATION LIST

Patent Literature

[Patent Literature 1] WO 2012/057262

Non-Patent Literature

[Non-Patent Literature 1] Nat Rev Neurosci. 14: 49, 2013
[Non-Patent Literature 2] Nat Commun. 3: 791, 2012

SUMMARY OF INVENTION

Technical Problem

The purpose of the present invention may be to provide a medicament for treating or preventing a disease involving Nav 1.7, specifically such as neuropathic pain, nociceptive pain, inflammatory pain, small-fiber neuropathy, erythromelalgia, paroxysmal extreme pain disorder, dysuria, and multiple sclerosis.

Solution to Problem

The present inventors have conducted intensive studies in an attempt to solve the aforementioned problem and found that a compound having a benzimidazole ring mentioned below or a pharmaceutically acceptable salt thereof can inhibit the membrane potential change or the Na ion current itself via Na channel in Nav 1.7 gene expressing cell, i.e., the compound or a pharmaceutically acceptable salt thereof is a blocker having a inhibitory activity for Nav 1.7. In addition, the present inventors have found that the derivative is useful as a medicament for treating or preventing a disease such as neuropathic pain, nociceptive pain, inflammatory pain, small-fiber neuropathy, erythromelalgia, and paroxysmal extreme pain disorder, which resulted in the completion of the present invention. Accordingly, the present invention can provide a benzimidazole compound represented by the following formula (I) (hereinafter, also referred to as "compound represented by formula (I)" or "compound of formula (I)") or a pharmaceutically acceptable salt thereof (hereinafter, also referred to as "compound of the present invention").

The present invention can show as follows.

Term 1

A compound of formula (I):

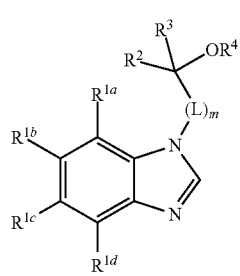

or a pharmaceutically acceptable salt thereof, wherein
$R^{1a}$, $R^{1b}$, $R^{1c}$, and $R^{1d}$ are independently hydrogen, halogen, cyano, $C_{1-4}$ alkyl, $C_{1-4}$ alkoxy, $C_{1-4}$ alkylamino, (wherein each alkyl moiety of the alkyl, the alkoxy and the alkylamino may be independently substituted with 1 to 5 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino, (wherein each cycloalkyl moiety of the cycloalkyl, the cycloalkoxy and the cycloalkylamino may be independently substituted with 1 to substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, or 5- to 12-membered heteroaryloxy, (wherein each aryl moiety of the aryl and the aryloxy and each heteroaryl moiety of the heteroaryl and the heteroaryloxy may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen, $C_{1-6}$ alkyl which may be independently substituted with 1 to 5 substituents selected independently from the group consisting of cyano, halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, or $C_{3-10}$ cycloalkyl, $R^4$ is hydrogen, $C_{1-6}$ alkyl which may be substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $C_{3-7}$ cycloalkyl which may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, m is 1, 2 or 3, L is $CR^7R^8$ provided that when m is 2 or 3, each $CR^7R^8$ are independently the same or different, $R^7$ and $R^8$ are independently hydrogen, hydroxyl, $C_{1-4}$ alkyl, $C_{1-4}$ alkoxy, (wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy, (wherein each cycloalkyl moiety of the cycloalkyl and the cycloalkoxy may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or in $R^2$, $R^3$ and —$OR^4$, $R^2$ and $R^3$ may be combined together with the carbon atom to which they are attached to form the following group of formula (II) with —$OR^4$

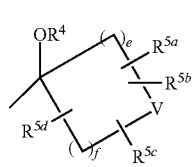

(II)

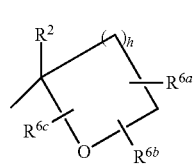

(III)

in formula (II), e and f are independently 1, 2 or 3, $R^4$ is as defined above, V is single bond or oxygen atom, $R^{5a}$, $R^{5b}$, $R^{5c}$, and $R^{5d}$ are independently hydrogen, halogen, hydroxyl, $C_{1-4}$ alkyl, or $C_{1-4}$ alkoxy, wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or in $R^2$, $R^3$, —$OR^4$ and $CR^7R^8$ in L, $R^2$ and $R^7$ may be combined together with the carbon atom to which they are attached to form the following group of formula (IV) with $R^3$, —$OR^4$ and $R^8$

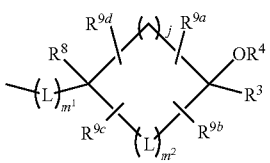

(IV)

in formula (IV), $m^1$ is 0 or 1, $m^2$ is 0 or 1 and j is 1, 2, 3 or 4 when $m^1$ is 1, or $m^2$ is 0, 1 or 2 and j is 1, 2, 3 or 4 when $m^1$ is 0, $R^3$, $R^4$, $R^8$ and L are as defined above, $R^{9a}$, $R^{9b}$, $R^{9c}$, and $R^{9d}$ are independently hydrogen, halogen, hydroxyl, $C_{1-4}$ alkyl, or $C_{1-4}$ alkoxy, wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $R^3$ and —$OR^4$ may be combined together with the carbon atom to which they are attached to form the following group of formula (III) with $R^2$ in formula (III), h is 1, 2, 3, or 4, $R^2$ is as defined above, $R^{6a}$, $R^{6b}$, and $R^{6c}$ are independently hydrogen, halogen, hydroxyl, $C_{1-4}$ alkyl, or $C_{1-4}$ alkoxy, wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, provided that all of $R^2$, $R^3$ and —$OR^4$ are not combined together to form a ring, Substituent-group A is independently halogen, hydroxyl, $C_{1-4}$ alkoxy, $C_{3-7}$ cycloalkyl, or $C_{3-7}$ cycloalkoxy, and Substituent-group B is independently halogen, hydroxyl, $C_{1-4}$ alkyl, $C_{1-4}$ alkoxy, $C_{3-7}$ cycloalkyl, or $C_{3-7}$ cycloalkoxy, provide that the following compounds are excluded:

6-[6-chloro-2-(morpholin-4-yl)pyrimidin-4-yl]-1-(2-methoxyethyl)-1H-benzimidazole, 2-[5-(3,5-dimethyl-1,2-oxazol-4-yl)-1H-benzimidazol-1-yl]ethanol, 2-{5-[5-(tetrahydrofuran-3-yl)-4H-1,2,4-triazol-3-yl]-1H-benzimidazol-1-yl}ethanol, 2-{5-[3-(2-methoxyethyl)-1-(2,2,2-trifluoroethyl)-1H-1,2,4-triazol-5-yl]-1H-benzimidazol-1-yl}ethanol, 2-{5-[3-methyl-1-(1-methylpiperidin-4-yl)-1H-1,2,4-triazol-5-yl]-1H-benzimidazol-1-yl}ethanol, 2-butyl-6-[1-(2-hydroxyethyl)-1H-benzimidazol-6-yl]-3,4-dihydropyrrolo[1,2-a]pyrazin-1(2H)-one, 6-[1-(2-hydroxyethyl)-1H-benzimidazol-6-yl]-2-(3-methylbutyl)-3,4-dihydropyrrolo[1,2-a]pyrazin-1(2H)-one, 2-{5-[1-(2-hydroxyethyl)-1H-benzimidazol-5-yl]-1H-1,2,4-triazol-1-yl}ethanol, 6-(2-chlorophenyl)-1-(2-hydroxyethyl)-1H-benzimidazole-7-carbonitrile, 2-chloro-6-{7-fluoro-1-[(1S,3S)-3-methoxycyclohexyl]-1H-benzimidazol-5-yl}-9-(tetrahydro-2H-pyran-2-yl)-9H-purine, and 2-{5-[2-(tetrahydrofuran-3-yl)-1H-imidazol-1-yl]-1H-benzimidazol-1-yl}ethanol.

Term 2

The compound of Term 1 presented in formula (I):

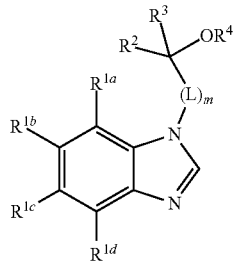

or a pharmaceutically acceptable salt thereof, wherein $R^{1a}$, $R^{1b}$, $R^{1c}$, and $R^{1d}$ are independently hydrogen, halogen, cyano, $C_{1-4}$ alkyl, $C_{1-4}$ alkoxy, $C_{1-4}$ alkylamino, (wherein each alkyl moiety of the alkyl, the alkoxy and the alkylamino may be independently substituted with 1 to 5 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino, (wherein each cycloalkyl moiety of the cycloalkyl, the cycloalkoxy and the cycloalkylamino may be independently substituted with 1 to substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen, $C_{1-6}$ alkyl which may be independently substituted with 1 to 5 substituents selected independently from the group consisting of cyano, halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, or $C_{3-10}$ cycloalkyl, $R^4$ is hydrogen, $C_{1-6}$ alkyl which may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $C_{3-7}$ cycloalkyl which may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, m is 1, 2 or 3, L is $CR^7R^8$ provided that when m is 2 or 3, each $CR^7R^8$ are independently the same or different, $R^7$ and $R^8$ are independently hydrogen, hydroxyl, $C_{1-4}$ alkyl, $C_{1-4}$ alkoxy, (wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy, (wherein each cycloalkyl moiety of the cycloalkyl and the cycloalkoxy may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), or in $R^2$, $R^3$ and —$OR^4$, $R^2$ and $R^3$ may be combined together with the carbon atom to which they are attached to form the following group of formula (II) with —$OR^4$

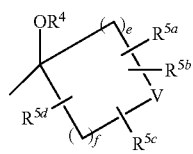

(II)

in formula (II), e and f are independently 1, 2 or 3, $R^4$ is as defined above, V is single bond or oxygen atom, $R^{5a}$, $R^{5b}$, $R^{5c}$, and $R^{5d}$ are independently hydrogen, halogen, hydroxyl, $C_{1-4}$ alkyl, or $C_{1-4}$ alkoxy, wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $R^3$ and —$OR^4$ may be combined together with the carbon atom to which they are attached to form the following group of formula (III) with $R^2$

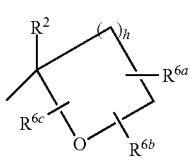

(III)

in formula (III), h is 1, 2, 3, or 4, $R^2$ is as defined above, $R^{6a}$, $R^{6b}$, and $R^{6c}$ are independently hydrogen, halogen, hydroxyl, $C_{1-4}$ alkyl, or $C_{1-4}$ alkoxy, wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, provided that all of $R^2$, $R^3$ and —$OR^4$ are not combined together to form a ring, Substituent-group A is independently halogen, hydroxyl, $C_{1-4}$ alkoxy, $C_{3-7}$ cycloalkyl, or $C_{3-7}$ cycloalkoxy, and Substituent-group B is independently halogen, hydroxyl, $C_{1-4}$ alkyl, $C_{1-4}$ alkoxy, $C_{3-7}$ cycloalkyl, or $C_{3-7}$ cycloalkoxy.

Term 3

The compound of Term 1 or 2 or a pharmaceutically acceptable salt thereof, wherein $R^{1a}$, $R^{1b}$, $R^{1c}$, and $R^{1d}$ are independently, hydrogen, halogen, cyano, $C_{1-4}$ alkyl, $C_{1-4}$ alkoxy (wherein each alkyl moiety of the alkyl and the alkoxy may be independently substituted with the same or different and 1 to 3 halogens), $C_{6-10}$ aryl, $C_{6-10}$ aryloxy, 5- to 12-membered heteroaryl, or 5- to 12-membered heteroaryloxy (wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A).

Term 4

The compound of any one of Terms 1 to 3 or a pharmaceutically acceptable salt thereof, wherein $R^{1a}$, $R^{1b}$, $R^{1c}$, and $R^{1d}$ are independently, hydrogen, $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen and $C_{1-4}$ alkyl optionally-substituted with 1 to 3 substituents selected independently from Substituent-group A.

Term 5

The compound of any one of Terms 1 to 4 or a pharmaceutically acceptable salt thereof, wherein $R^{1a}$ and $R^{1d}$ are hydrogen.

Term 6

The compound of any one of Terms 1 and 3 to 5 or a pharmaceutically acceptable salt thereof, wherein $R^2$ and $R^3$ are independently hydrogen or $C_{1-6}$ alkyl which may be independently substituted with 1 to 5 substituents selected independently from the group consisting of cyano, halogen, hydroxyl, and $C_{1-4}$ alkoxy optionally-substituted with 1 to 3 substituents selected independently from Substituent-group A, provided that both of $R^2$ and $R^3$ are not hydrogen, or $R^2$ and $R^3$ may be combined together with the carbon atom to which they are attached to form the following group of formula (IIa) with —$OR^4$

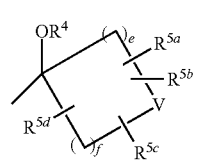

(IIa)

in formula (IIa), e and f are independently 1 or 2, $R^4$ and V are as defined in Term 1, and $R^{5a}$, $R^{5b}$, $R^{5c}$, and $R^{5d}$ are independently hydrogen or halogen, or in $R^2$, $R^3$, —$OR^4$ and $CR^7R^8$ in L, $R^2$ and $R^7$ may be combined together with the carbon atom to which they are attached to form the following group of formula (IVa) with $R^3$, —$OR^4$ and $R^8$

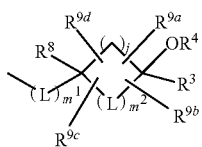
(IVa)

in formula (IVa),
$m^1$ is 0,
$m^2$ is 1 or 2,
j is 1, 2 or 3,
$R^3$ is as defined above,
$R^4$, $R^8$ and L are as defined in Term 1, and
$R^{9a}$, $R^{9b}$, $R^{9c}$, and $R^{9d}$ are independently hydrogen or halogen.

Term 7

The compound of any one of Terms 1 and 3 to 6 or a pharmaceutically acceptable salt thereof, wherein
$R^2$ and $R^3$ are independently $C_{1-6}$ alkyl optionally-substituted with the same or different and 1 to 5 halogens, or
$R^2$ and $R^3$ may be combined together with the carbon atom to which they are attached to form the following group of formula (IIb) with —$OR^4$

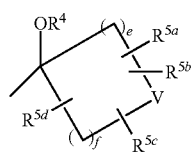
(IIb)

in formula (IIb),
e and f are independently 1 or 2,
$R^4$ and V are as defined in Term 1, and
$R^{5a}$, $R^{5b}$, $R^{5c}$, and $R^{5d}$ are independently hydrogen or halogen, or
in $R^2$, $R^3$, —$OR^4$ and $CR^7R^8$ in L,
$R^2$ and $R^7$ may be combined together with the carbon atom to which they are attached to form the following group of formula (IVa) with $R^3$, —$OR^4$ and $R^8$

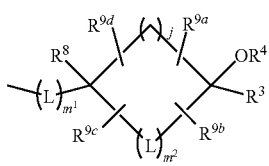
(IVa)

in formula (IVa),
$m^1$ is 0,
$m^2$ is 1 or 2,
j is 1, 2 or 3,
$R^4$ is hydrogen,
$R^8$ and L are as defined in Term 1, and
$R^{9a}$, $R^{9b}$, $R^{9c}$, and $R^{9d}$ are independently hydrogen or halogen.

Term 8

The compound of any one of Terms 1 to 6 or a pharmaceutically acceptable salt thereof, wherein
$R^2$ and $R^3$ are independently hydrogen or $C_{1-6}$ alkyl which may be independently substituted with 1 to 5 substituents selected independently from the group consisting of cyano, halogen, hydroxyl, and $C_{1-4}$ alkoxy optionally-substituted with 1 to 3 substituents selected independently from Substituent-group A, or
$R^2$ and $R^3$ may be combined together with the carbon atom to which they are attached to form the following group of formula (IIa) with —$OR^4$

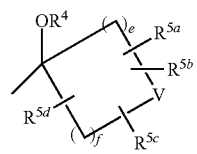
(IIa)

in formula (IIa),
e and f are independently 1 or 2,
$R^4$ and V are as defined in Term 1, and
$R^{5a}$, $R^{5b}$, $R^{5c}$, and $R^{5d}$ are independently hydrogen or halogen.

Term 9

The compound of any one of Terms 1 to 6 or a pharmaceutically acceptable salt thereof, wherein
$R^2$ and $R^3$ are independently hydrogen or $C_{1-6}$ alkyl optionally-substituted with the same or different and 1 to 5 halogens, or
$R^2$ and $R^3$ may be combined together with the carbon atom to which they are attached to form the following group of formula (IIb) with —$OR^4$

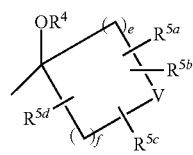
(IIb)

in formula (IIb),
e and f are independently 1 or 2,
$R^4$ and V are as defined in Term 1, and
$R^{5a}$, $R^{5b}$, $R^{5c}$, and $R^{5d}$ are independently hydrogen or halogen.

Term 10

The compound of any one of Terms 1 to 9 or a pharmaceutically acceptable salt thereof, wherein
$R^2$ and $R^3$ are independently hydrogen or $C_{1-6}$ alkyl optionally-substituted with the same or different and 1 to 5 halogens, and $R^2$ and $R^3$ are not combined together with the carbon atom to which they are attached to form a ring.

Term 11

The compound of any one of Terms 1 to 5 and 10 or a pharmaceutically acceptable salt thereof, wherein
$R^4$ is hydrogen, $C_{1-4}$ alkyl optionally-substituted with the same or different and 1 to 3 halogens, or $C_{3-7}$ cycloalkyl which may be substituted with 1 to 3 substituents selected independently from the group consisting of halogen, hydroxyl, and $C_{1-4}$ alkoxy optionally-substituted with 1 to 3 substituents selected independently from Substituent-group A, or
$R^3$ and —$OR^4$ may be combined together with the carbon atom to which they are attached to form the following group of formula (IIIa) with $R^2$

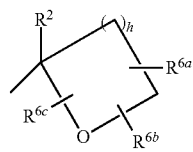

(IIIa)

in formula (IIIa),
h is 1, 2, or 3,
$R^2$ is as defined in Term 1,
$R^{6a}$, $R^{6b}$, and $R^{6c}$ are independently, hydrogen, halogen, or $C_{1-4}$ alkyl optionally-substituted with the same or different and 1 to 3 halogens.

Term 12

The compound of any one of Terms 1 to 11 or a pharmaceutically acceptable salt thereof, wherein $R^4$ is hydrogen, $C_{1-4}$ alkyl optionally-substituted with the same or different and 1 to 3 halogens, or $C_{3-7}$ cycloalkyl which may be substituted with 1 to 3 substituents selected independently from the group consisting of halogen, hydroxyl, and $C_{1-4}$ alkoxy optionally-substituted with 1 to 3 substituents selected independently from Substituent-group A, and $R^3$ and —$OR^4$ are not combined together with the carbon atom to which they are attached to form a ring.

Term 13

The compound of any one of Terms 1 to 12 or a pharmaceutically acceptable salt thereof, wherein $R^4$ is hydrogen.

Term 14

The compound of any one of Terms 1 to 13 or a pharmaceutically acceptable salt thereof, wherein $R^7$ and $R^8$ are independently hydrogen or $C_{1-4}$ alkyl which may be substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, and m is 1 or 2.

Term 15

The compound of any one of Terms 1 to 14 or a pharmaceutically acceptable salt thereof, wherein $R^7$ and $R^8$ are hydrogen, and m is 1.

Term 16

The compound of any one of Terms 1 to 15 or a pharmaceutically acceptable salt thereof, wherein $R^{1b}$ or $R^{1c}$ is $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A.

Term 17

The compound of any one of Terms 1 to 16 or a pharmaceutically acceptable salt thereof, wherein $R^{1b}$ is $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A.

Term 18

The compound of any one of Terms 1 to 16 or a pharmaceutically acceptable salt thereof, wherein $R^{1c}$ is $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A.

Term 19

The compound of any one of Terms 1 to 16 or a pharmaceutically acceptable salt thereof, wherein $R^{1b}$ or $R^{1c}$ is $C_{6-10}$ aryloxy or 5- to 12-membered heteroaryloxy wherein the aryl moiety of the aryloxy and the heteroaryl moiety of the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A.

Term 20

The compound of any one of Terms 1 to 16 or a pharmaceutically acceptable salt thereof, wherein $R^{1b}$ or $R^{1c}$ is $C_{6-10}$ aryl or 5- to 12-membered heteroaryl wherein the aryl and the heteroaryl may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A.

Term 21

The compound of any one of Terms 1 to 20 or a pharmaceutically acceptable salt thereof, wherein $R^2$ and $R^3$ are independently $C_{1-6}$ alkyl optionally-substituted with the same or different and 1 to 5 halogens.

Term 22

The compound of any one of Terms 1 and 3 to 20 or a pharmaceutically acceptable salt thereof, wherein $R^2$ and $R^3$ may be combined together with the carbon atom to which they are attached to form the following group of formula (IIb) with —$OR^4$

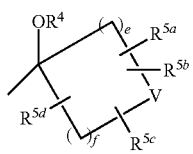
(IIb)

in formula (IIb),
e and f are independently 1 or 2,
$R^4$ and V are as defined in Term 1, and
$R^{5a}$, $R^{5b}$, $R^{5c}$, and $R^{5d}$ are independently hydrogen or halogen, or
in $R^2$, $R^3$, —$OR^4$ and $CR^7R^8$ in L,
$R^2$ and $R^7$ may be combined together with the carbon atom to which they are attached to form the following group of formula (IVa) with $R^3$, —$OR^4$ and $R^8$

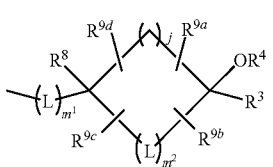
(IVa)

in formula (IVa),
$m^1$ is 0,
$m^2$ is 1 or 2,
j is 1, 2 or 3,
$R^4$ is hydrogen,
$R^8$ and L are as defined in Term 1, and
$R^{9a}$, $R^{9b}$, $R^{9c}$, and $R^{9d}$ are independently hydrogen or halogen.

Term 23

The compound of Term 1 or 2, or a pharmaceutically acceptable salt thereof, which is selected from the following compounds:

Example 1: 1-[6-(4-fluorophenoxy)-1H-benzimidazol-1-yl]-2-methylpropan-2-ol,
Example 2: 6-(4-fluorophenoxy)-1-(tetrahydrofuran-2-ylmethyl)-1H-benzimidazole,
Example 7: 1-(tetrahydrofuran-2-ylmethyl)-6-[4-(trifluoromethyl)phenyl]-1H-benzimidazole,
Example 9: 2-methyl-1-{6-[4-(trifluoromethyl)phenyl]-1H-benzimidazol-1-yl}propan-2-ol,
Example 10: 1-[2-(cyclopentyloxy)ethyl]-6-[4-(trifluoromethyl)phenyl]-1H-benzimidazole,
Example 11: 2-methyl-1-{6-[5-(trifluoromethyl)pyridin-2-yl]-1H-benzimidazol-1-yl}propan-2-ol,
Example 12: 1-[2-(cyclopentyloxy)ethyl]-6-[5-(trifluoromethyl)pyridin-2-yl]-1H-benzimidazole,
Example 14: 2-methyl-1-[6-(4-methylphenoxy)-1H-benzimidazol-1-yl]propan-2-ol,
Example 15: 2-methyl-1-{6-[4-(trifluoromethyl)phenoxy]-1H-benzimidazol-1-yl}propan-2-ol,
Example 20: 1-[6-(4-chlorophenoxy)-1H-benzimidazol-1-yl]-2-methylpropan-2-ol,
Example 22: 2-methyl-1-{6-[4-(trifluoromethoxy)phenoxy]-1H-benzimidazol-1-yl}propan-2-ol,
Example 24: 2-methyl-1-{6-[(6-methylpyridin-3-yl)oxy]-1H-benzimidazol-1-yl}propan-2-ol,
Example 25: 2-methyl-1-(6-{[6-(trifluoromethyl)pyridin-3-yl]oxy}-1H-benzimidazol-1-yl)propan-2-ol,
Example 28: 2-methyl-1-(6-{[5-(trifluoromethyl)pyridin-2-yl]oxy}-1H-benzimidazol-1-yl)propan-2-ol,
Example 51: 2-methyl-1-(5-{[5-(trifluoromethyl)pyrazin-2-yl]oxy}-1H-benzimidazol-1-yl)propan-2-ol,
Example 52: 2-methyl-1-(5-{[5-(trifluoromethyl)pyrimidin-2-yl]oxy}-1H-benzimidazol-1-yl)propan-2-ol,
Example 53: 1-(5-{[3-fluoro-5-(trifluoromethyl)pyridin-2-yl]oxy}-1H-benzimidazol-1-yl)-2-methylpropan-2-ol,
Example 54: 1-{5-[(5-chloro-3-fluoropyridin-2-yl)oxy]-1H-benzimidazol-1-yl}-2-methylpropan-2-ol,
Example 56: 3-[(6-{[5-(trifluoromethyl)pyridin-2-yl]oxy}-1H-benzimidazol-1-yl)methyl]oxetan-3-ol,
Example 58: 1-[(6-{[5-(trifluoromethyl)pyridin-2-yl]oxy}-1H-benzimidazol-1-yl)methyl]cyclobutanol,
Example 59: 2-methyl-4-(6-{[5-(trifluoromethyl)pyridin-2-yl]oxy}-1H-benzimidazol-1-yl)butan-2-ol,
Example 60: 2-methyl-1-(6-{[5-(2,2,2-trifluoroethyl)pyridin-2-yl]oxy}-1H-benzimidazol-1-yl)propan-2-ol,
Example 93: 3-({6-[4-(trifluoromethyl)phenoxy]-1H-benzimidazol-1-yl}methyl)oxetan-3-ol,
Example 94: 3-({6-[4-(trifluoromethoxy)phenoxy]-1H-benzimidazol-1-yl}methyl)oxetan-3-ol,
Example 101: 4-[6-(4-chlorophenoxy)-1H-benzimidazol-1-yl]-2-methylbutan-2-ol,
Example 110: 3-{[6-(2-chloro-4-fluorophenoxy)-1H-benzimidazol-1-yl]methyl}oxetan-3-ol,
Example 118: cis-4-(6-{[5-(trifluoromethyl)pyridin-2-yl]oxy}-1H-benzimidazol-1-yl)cyclohexanol,
Example 123: 1-{6-[2-fluoro-4-(trifluoromethyl)phenyl]-1H-benzimidazol-1-yl}-2-methylpropan-2-ol,
Example 130: 1-[6-(4-chloro-2-fluorophenyl)-1H-benzimidazol-1-yl]-2-methylpropan-2-ol,
Example 148: 3-({6-[2-methoxy-4-(trifluoromethyl)phenyl]-1H-benzimidazol-1-yl}methyl)oxetan-3-ol,
Example 173: 4-{6-[2-methoxy-4-(trifluoromethyl)phenyl]-1H-benzimidazol-1-yl}-2-methylbutan-2-ol,
Example 176: 1-{5-[2-methoxy-4-(trifluoromethyl)phenyl]-1H-benzimidazol-1-yl}-2-methylpropan-2-ol,
Example 179: 2-methyl-1-{5-[4-(trifluoromethoxy)phenyl]-1H-benzimidazol-1-yl}propan-2-ol,
Example 181: 1-{5-[2-fluoro-4-(trifluoromethyl)phenyl]-1H-benzimidazol-1-yl}-2-methylpropan-2-ol,
Example 205: 3-({5-[2-methoxy-4-(trifluoromethyl)phenyl]-1H-benzimidazol-1-yl}methyl)oxetan-3-ol, and
Example 229: (3S)-2-methyl-3-(6-{[5-(trifluoromethyl)pyridin-2-yl]oxy}-1H-benzimidazol-1-yl)butan-2-ol.

Term 24

The compound of Term 1 or 2, or a pharmaceutically acceptable salt thereof, which is selected from the following compounds:

Example 1: 1-[6-(4-fluorophenoxy)-1H-benzimidazol-1-yl]-2-methylpropan-2-ol,
Example 2: 6-(4-fluorophenoxy)-1-(tetrahydrofuran-2-ylmethyl)-1H-benzimidazole,
Example 7: 1-(tetrahydrofuran-2-ylmethyl)-6-[4-(trifluoromethyl)phenyl]-1H-benzimidazole,
Example 9: 2-methyl-1-{6-[4-(trifluoromethyl)phenyl]-1H-benzimidazol-1-yl}propan-2-ol,
Example 10: 1-[2-(cyclopentyloxy)ethyl]-6-[4-(trifluoromethyl)phenyl]-1H-benzimidazole,
Example 11: 2-methyl-1-{6-[5-(trifluoromethyl)pyridin-2-yl]-1H-benzimidazol-1-yl}propan-2-ol,
Example 12: 1-[2-(cyclopentyloxy)ethyl]-6-[5-(trifluoromethyl)pyridin-2-yl]-1H-benzimidazole,
Example 14: 2-methyl-1-[6-(4-methylphenoxy)-1H-benzimidazol-1-yl]propan-2-ol, Example 15: 2-methyl-1-{6-[4-(trifluoromethyl)phenoxy]-1H-benzimidazol-1-yl}propan-2-ol,
Example 20: 1-[6-(4-chlorophenoxy)-1H-benzimidazol-1-yl]-2-methylpropan-2-ol,
Example 22: 2-methyl-1-{6-[4-(trifluoromethoxy)phenoxy]-1H-benzimidazol-1-yl}propan-2-ol,
Example 24: 2-methyl-1-{6-[(6-methylpyridin-3-yl)oxy]-1H-benzimidazol-1-yl}propan-2-ol,
Example 25: 2-methyl-1-(6-{[6-(trifluoromethyl)pyridin-3-yl]oxy}-1H-benzimidazol-1-yl)propan-2-ol,
Example 28: 2-methyl-1-(6-{[5-(trifluoromethyl)pyridin-2-yl]oxy}-1H-benzimidazol-1-yl)propan-2-ol,
Example 51: 2-methyl-1-(5-{[5-(trifluoromethyl)pyrazin-2-yl]oxy}-1H-benzimidazol-1-yl)propan-2-ol,
Example 52: 2-methyl-1-(5-{[5-(trifluoromethyl)pyrimidin-2-yl]oxy}-1H-benzimidazol-1-yl)propan-2-ol,
Example 53: 1-(5-{[3-fluoro-5-(trifluoromethyl)pyridin-2-yl]oxy}-1H-benzimidazol-1-yl)-2-methylpropan-2-ol,
Example 54: 1-{5-[(5-chloro-3-fluoropyridin-2-yl)oxy]-1H-benzimidazol-1-yl}-2-methylpropan-2-ol,
Example 56: 3-[(6-{[5-(trifluoromethyl)pyridin-2-yl]oxy}-1H-benzimidazol-1-yl)methyl]oxetan-3-ol,
Example 58: 1-[(6-{[5-(trifluoromethyl)pyridin-2-yl]oxy}-1H-benzimidazol-1-yl)methyl]cyclobutanol,
Example 59: 2-methyl-4-(6-{[5-(trifluoromethyl)pyridin-2-yl]oxy}-1H-benzimidazol-1-yl)butan-2-ol, and
Example 60: 2-methyl-1-(6-{[5-(2,2,2-trifluoroethyl)pyridin-2-yl]oxy}-1H-benzimidazol-1-yl)propan-2-ol.

Term 25
The compound of Term 1 or 2, or a pharmaceutically acceptable salt thereof, which is selected from the following compounds:
Example 1: 1-[6-(4-fluorophenoxy)-1H-benzimidazol-1-yl]-2-methylpropan-2-ol,
Example 9: 2-methyl-1-{6-[4-(trifluoromethyl)phenyl]-1H-benzimidazol-1-yl}propan-2-ol,
Example 11: 2-methyl-1-{6-[5-(trifluoromethyl)pyridin-2-yl]-1H-benzimidazol-1-yl}propan-2-ol,
Example 15: 2-methyl-1-{6-[4-(trifluoromethyl)phenoxy]-1H-benzimidazol-1-yl}propan-2-ol,
Example 20: 1-[6-(4-chlorophenoxy)-1H-benzimidazol-1-yl]-2-methylpropan-2-ol,
Example 22: 2-methyl-1-{6-[4-(trifluoromethoxy)phenoxy]-1H-benzimidazol-1-yl}propan-2-ol,
Example 24: 2-methyl-1-{6-[(6-methylpyridin-3-yl)oxy]-1H-benzimidazol-1-yl}propan-2-ol,
Example 28: 2-methyl-1-(6-{[5-(trifluoromethyl)pyridin-2-yl]oxy}-1H-benzimidazol-1-yl)propan-2-ol,
Example 51: 2-methyl-1-(5-{[5-(trifluoromethyl)pyrazin-2-yl]oxy}-1H-benzimidazol-1-yl)propan-2-ol,
Example 53: 1-(5-{[3-fluoro-5-(trifluoromethyl)pyridin-2-yl]oxy}-1H-benzimidazol-1-yl)-2-methylpropan-2-ol,
Example 59: 2-methyl-4-(6-{[5-(trifluoromethyl)pyridin-2-yl]oxy}-1H-benzimidazol-1-yl)butan-2-ol,
Example 60: 2-methyl-1-(6-{[5-(2,2,2-trifluoroethyl)pyridin-2-yl]oxy}-1H-benzimidazol-1-yl)propan-2-ol,
Example 94: 3-({6-[4-(trifluoromethoxy)phenoxy]-1H-benzimidazol-1-yl}methyl)oxetan-3-ol,
Example 101: 4-[6-(4-chlorophenoxy)-1H-benzimidazol-1-yl]-2-methylbutan-2-ol,
Example 118: cis-4-(6-{[5-(trifluoromethyl)pyridin-2-yl]oxy}-1H-benzimidazol-1-yl)cyclohexanol,
Example 123: 1-{6-[2-fluoro-4-(trifluoromethyl)phenyl]-1H-benzimidazol-1-yl}-2-methylpropan-2-ol,
Example 148: 3-({6-[2-methoxy-4-(trifluoromethyl)phenyl]-1H-benzimidazol-1-yl}methyl)oxetan-3-ol,
Example 205: 3-({5-[2-methoxy-4-(trifluoromethyl)phenyl]-1H-benzimidazol-1-yl}methyl)oxetan-3-ol, and
Example 229: (3S)-2-methyl-3-(6-{[5-(trifluoromethyl)pyridin-2-yl]oxy}-1H-benzimidazol-1-yl)butan-2-ol.

Term 26
The compound of Term 1 or 2, or a pharmaceutically acceptable salt thereof, which is selected from the following compounds:
Example 1: 1-[6-(4-fluorophenoxy)-1H-benzimidazol-1-yl]-2-methylpropan-2-ol,
Example 9: 2-methyl-1-{6-[4-(trifluoromethyl)phenyl]-1H-benzimidazol-1-yl}propan-2-ol,
Example 11: 2-methyl-1-{6-[5-(trifluoromethyl)pyridin-2-yl]-1H-benzimidazol-1-yl}propan-2-ol,
Example 15: 2-methyl-1-{6-[4-(trifluoromethyl)phenoxy]-1H-benzimidazol-1-yl}propan-2-ol,
Example 20: 1-[6-(4-chlorophenoxy)-1H-benzimidazol-1-yl]-2-methylpropan-2-ol,
Example 22: 2-methyl-1-{6-[4-(trifluoromethoxy)phenoxy]-1H-benzimidazol-1-yl}propan-2-ol,
Example 24: 2-methyl-1-{6-[(6-methylpyridin-3-yl)oxy]-1H-benzimidazol-1-yl}propan-2-ol,
Example 28: 2-methyl-1-(6-{[5-(trifluoromethyl)pyridin-2-yl]oxy}-1H-benzimidazol-1-yl)propan-2-ol,
Example 51: 2-methyl-1-(5-{[5-(trifluoromethyl)pyrazin-2-yl]oxy}-1H-benzimidazol-1-yl)propan-2-ol,
Example 53: 1-(5-{[3-fluoro-5-(trifluoromethyl)pyridin-2-yl]oxy}-1H-benzimidazol-1-yl)-2-methylpropan-2-ol,
Example 59: 2-methyl-4-(6-{[5-(trifluoromethyl)pyridin-2-yl]oxy}-1H-benzimidazol-1-yl)butan-2-ol, and
Example 60: 2-methyl-1-(6-{[5-(2,2,2-trifluoroethyl)pyridin-2-yl]oxy}-1H-benzimidazol-1-yl)propan-2-ol.

Term 27
A pharmaceutical composition comprising the compound of any one of Terms 1 to 26 or a pharmaceutically acceptable salt thereof.

Term 28
A medicament for treating a disease involving Nav 1.7 (SCN9A), comprising the compound of any one of Terms 1 to 26 or a pharmaceutically acceptable salt thereof as an active ingredient.

Term 29
A compound of any one of Terms 1 to 26 or a pharmaceutically acceptable salt thereof, or a compound selected from the group consisting of
6-[6-chloro-2-(morpholin-4-yl)pyrimidin-4-yl]-1-(2-methoxyethyl)-1H-benzimidazole,
2-[5-(3,5-dimethyl-1,2-oxazol-4-yl)-1H-benzimidazol-1-yl]ethanol,
2-{5-[5-(tetrahydrofuran-3-yl)-4H-1,2,4-triazol-3-yl]-1H-benzimidazol-1-yl}ethanol,
2-{5-[3-(2-methoxyethyl)-1-(2,2,2-trifluoroethyl)-1H-1,2,4-triazol-5-yl]-1H-benzimidazol-1-yl}ethanol,
2-{5-[3-methyl-1-(1-methylpiperidin-4-yl)-1H-1,2,4-triazol-5-yl]-1H-benzimidazol-1-yl}ethanol,
2-butyl-6-[1-(2-hydroxyethyl)-1H-benzimidazol-6-yl]-3,4-dihydropyrrolo[1,2-a]pyrazin-1(2H)-one,
6-[1-(2-hydroxyethyl)-1H-benzimidazol-6-yl]-2-(3-methylbutyl)-3,4-dihydropyrrolo[1,2-a]pyrazin-1(2H)-one,
2-{5-[1-(2-hydroxyethyl)-1H-benzimidazol-5-yl]-1H-1,2,4-triazol-1-yl}ethanol,
6-(2-chlorophenyl)-1-(2-hydroxyethyl)-1H-benzimidazole-7-carbonitrile,
2-chloro-6-{7-fluoro-1-[(1S,3S)-3-methoxycyclohexyl]-1H-benzimidazol-5-yl}-9-(tetrahydro-2H-pyran-2-yl)-9H-purine, and 2-{5-[2-(tetrahydrofuran-3-yl)-1H-imidazol-1-yl]-1H-benzimidazol-1-yl}ethanol,
or a pharmaceutically acceptable salt thereof.

Term 30

A medicament for treating a disease involving Nav 1.7 (SCN9A), comprising the compound of Term 29 or a pharmaceutically acceptable salt thereof as an active ingredient.

Term 29 is the same as any one of Terms 1 to 26, provided that the 11 compounds excluded at the proviso in the end of Term 1 should not be excluded.

Term 31

A medicament for treating neuropathic pain, nociceptive pain, inflammatory pain, small-fiber neuropathy, erythromelalgia, paroxysmal extreme pain disorder, dysuria, or multiple sclerosis, which comprises the compound of any one of Terms 1 to 26 or a pharmaceutically acceptable salt thereof as an active ingredient.

Term 32

A medicament for treating neuropathic pain, nociceptive pain, inflammatory pain, small-fiber neuropathy, erythromelalgia, paroxysmal extreme pain disorder, dysuria, or multiple sclerosis, which comprises the compound of Term 29 or a pharmaceutically acceptable salt thereof as an active ingredient.

Term 33

A pharmaceutical combination comprising the compound of any one of Terms 1 to 26 or a pharmaceutically acceptable salt thereof, and at least one drug selected from the group consisting of an antiepileptic agent, an antidepressive agent, a narcotic analgesic, an anti-inflammatory agent, a reductase inhibitor, and a prostaglandin derivative drug.

Term 34

A pharmaceutical combination comprising the compound of Term 29 or a pharmaceutically acceptable salt thereof, and at least one drug selected from the group consisting of an antiepileptic agent, an antidepressive agent, a narcotic analgesic, an anti-inflammatory agent, a reductase inhibitor, and a prostaglandin derivative drug.

Term 35

Use of the compound of any one of Terms 1 to 26 or a pharmaceutically acceptable salt thereof in the manufacture of a medicament for treating neuropathic pain, nociceptive pain, inflammatory pain, small-fiber neuropathy, erythromelalgia, paroxysmal extreme pain disorder, dysuria, or multiple sclerosis.

Term 36

Use of the compound of Term 29 or a pharmaceutically acceptable salt thereof in the manufacture of a medicament for treating neuropathic pain, nociceptive pain, inflammatory pain, small-fiber neuropathy, erythromelalgia, paroxysmal extreme pain disorder, dysuria, or multiple sclerosis.

Term 37

A method for treating neuropathic pain, nociceptive pain, inflammatory pain, small-fiber neuropathy, erythromelalgia, paroxysmal extreme pain disorder, dysuria, or multiple sclerosis, which comprises administering a therapeutically effective amount of the compound of any one of Terms 1 to 26 or a pharmaceutically acceptable salt thereof to a mammal in need thereof.

Term 38

A method for treating neuropathic pain, nociceptive pain, inflammatory pain, small-fiber neuropathy, erythromelalgia, paroxysmal extreme pain disorder, dysuria, or multiple sclerosis, which comprises administering a therapeutically effective amount of the compound of Term 29 or a pharmaceutically acceptable salt thereof to a mammal in need thereof.

Effect of Invention

The present invention provides a Nav 1.7 blocker comprising a novel benzimidazole compound or a pharmaceutically acceptable salt thereof. The compounds of the present invention are useful as a medicament for treating or preventing a disease involving Nav 1.7 (SCN9A), namely, the compounds are applicable to a patient suffering from neuropathic pain, nociceptive pain, inflammatory pain, small-fiber neuropathy, erythromelalgia, paroxysmal extreme pain disorder, and the like.

DESCRIPTION OF EMBODIMENTS

Hereafter, the present invention is explained in more detail. The number of carbon atoms in the "substituent group" used herein can be sometimes expressed, for example, as "$C_{1-6}$". Specifically, the term "$C_{1-6}$ alkyl" means an alkyl having 1 to 6 carbon atoms. In the present description, a substituent group which is not accompanied with "optionally-substituted" or "substituted" means an "unsubstituted" substituent group. For example, "$C_{1-6}$ alkyl" means "unsubstituted $C_{1-6}$ alkyl".

The substituent groups in the present description may be sometimes expressed without the term "group". In case that "optionally-substituted" is used in the definition of substituent groups, the number of the substituting groups is not limited as long as the substitutions are available, i.e., it is one or more. It means that the possible number of substituting groups is the substitution-available number on carbon atoms or carbon-nitrogen atoms in a substituent group which are acceptable for substitution. Unless otherwise specified, the definition of each substituent group also extends over the case of partially-including the substituent group or the case that the substituent group substituting another substituent groups.

Unless otherwise specified, the binding site of substituent groups is not limited as long as the site is available to be bound.

The "halogen" includes, for example, fluorine, chlorine, bromine, and iodine, preferably fluorine and chlorine.

The "$C_{1-2}$ alkyl" means a saturated hydrocarbon group having 1 to 2 carbon atoms, the "$C_{1-3}$ alkyl" means a saturated straight or branched chain hydrocarbon group having 1 to 3 carbon atoms, the "$C_{1-4}$ alkyl" means a saturated straight or branched chain hydrocarbon group having 1 to 4 carbon atoms, and the "$C_{1-6}$ alkyl" means a saturated straight or branched chain hydrocarbon group having 1 to 6 carbon atoms. The "$C_{1-2}$ alkyl" includes, for example, methyl and ethyl; the "$C_{1-3}$ alkyl" includes, for example, propyl and isopropyl, besides the above alkyl; the "$C_{1-4}$ alkyl" includes, for example, butyl, isobutyl, sec-butyl, and tert-butyl, besides the above alkyl; and the "$C_{1-6}$ alkyl" includes, for example, pentyl, isopentyl, neopentyl, 1-ethylpropyl, hexyl, and a structural isomer thereof, besides the above alkyl. Preferred examples of the "$C_{1-6}$ alkyl" or "$C_{1-4}$ alkyl" include "$C_{1-3}$ alkyl", and more preferably methyl and ethyl.

The "$C_{3-7}$ cycloalkyl" means a non-aromatic cyclic hydrocarbon group (i.e., saturated hydrocarbon group and partially-unsaturated hydrocarbon group) having 3 to 7 carbon atoms, and the "$C_{3-10}$ cycloalkyl" means a non-aromatic cyclic hydrocarbon group (i.e., saturated hydrocarbon group and partially-unsaturated hydrocarbon group) having 3 to 10 carbon atoms. The "$C_{3-7}$ cycloalkyl" and the "$C_{3-10}$ cycloalkyl" also include a bridged one. The "$C_{3-7}$ cycloalkyl" includes, for example, cyclopropyl, cyclobutyl, cyclopentyl, cyclohexyl, cyclopentenyl, cyclohexenyl, and cycloheptyl. The "$C_{3-10}$ cycloalkyl" includes, for example, cyclooctyl and adamantyl, besides the above, preferably, "$C_{3-7}$ cycloalkyl".

The "$C_{3-7}$ cycloalkyl" and the "$C_{3-10}$ cycloalkyl" also include a bi-cyclic condensed ring in which the "$C_{3-7}$ cycloalkyl" and "$C_{3-10}$ cycloalkyl" are fused with benzene or a 5- or 6-membered ring having one heteroatom selected from nitrogen, sulfur, or oxygen atom, or the same or different and two or more (for example, 2 to 4) heteroatoms thereof (for example, "5- or 6-membered mono-cyclic heteroaryl" mentioned below, and 5- or 6-membered ring in "3- to 7-membered non-aromatic heterocyclyl" mentioned below), respectively. Examples of the bi-cyclic condensed ring include groups of the following formulae.

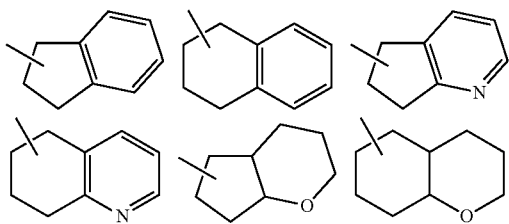

The "$C_{6-10}$ aryl" means an aromatic hydrocarbon group having 6 to 10 carbon atoms, preferably phenyl. The "$C_{6-10}$ aryl" includes, for example, phenyl, 1-naphthyl and 2-naphthyl.

The "$C_{6-10}$ aryl" also includes a condensed ring in which "phenyl" is fused with a 5- or 6-membered ring having one heteroatom selected from nitrogen, sulfur, or oxygen atom, or the same or different and two or more (for example, 2 to 4) heteroatoms thereof (for example, "5- or 6-membered mono-cyclic heteroaryl" mentioned below, and 5- or 6-membered ring in "3- to 7-membered non-aromatic heterocyclyl" mentioned below), or a 5- to 7-membered cycloalkyl ring (for example, cyclopentane, cyclohexane and cycloheptane). Examples of the condensed ring include groups of the following formulae.

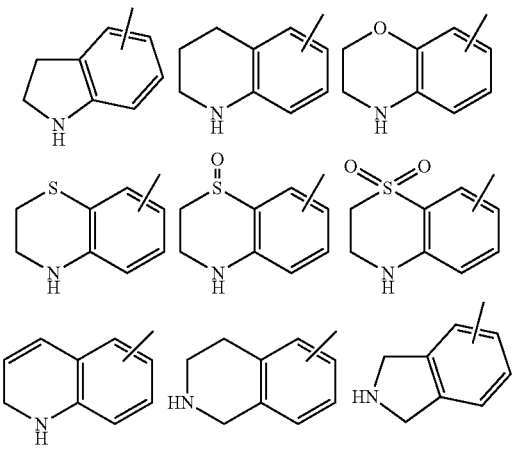

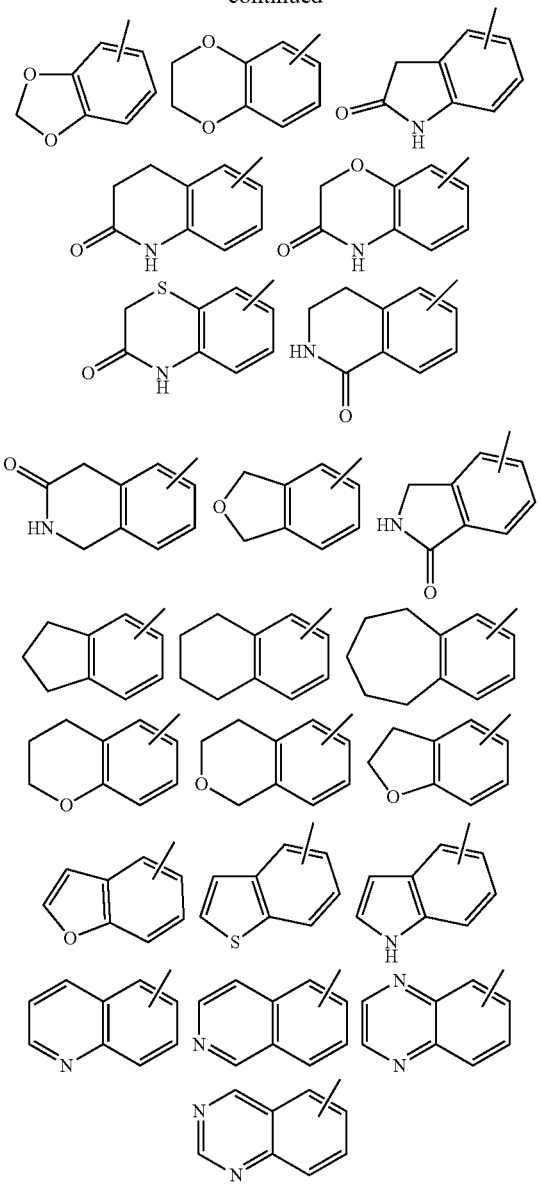

The "5- to 12-membered heteroaryl" means a 5- to 12-membered mono- or multiple-cyclic aromatic group having one heteroatom selected from nitrogen, sulfur, or oxygen atom, or the same or different and two or more (for example, 2 to 4) heteroatoms thereof, besides carbon atoms as the ring atoms, preferably, "5- or 6-membered mono-cyclic heteroaryl" The "5- or 6-membered mono-cyclic heteroaryl" means a 5- or 6-membered mono-cyclic aromatic group within the "5- to 12-membered heteroaryl".

The multiple-cyclic heteroaryl in the "5- to 12-membered heteroaryl" includes, for example, a condensed ring in which the same or different two mono-cyclic heteroaryls are fused, or a mono-cyclic heteroaryl and an aromatic ring (for example, benzene) or a non-aromatic ring (for example, cyclohexane) are fused.

The "5- to 12-membered heteroaryl" includes, for example, groups of the formulae shown below. Preferably, the "5- to 12-membered heteroaryl" includes pyrazolyl, imidazolyl, pyridyl, pyrimidinyl, pyrazinyl, and pyridazinyl. Another embodiment includes, preferably, benzofuranyl in which the binding site is on the heteroaryl (furan) ring, pyridyl, pyrimidinyl, pyrazinyl, and pyridazinyl. Examples of the "5- or 6-membered mono-cyclic heteroaryl" include mono-cyclic groups out of the groups of the following formulae.

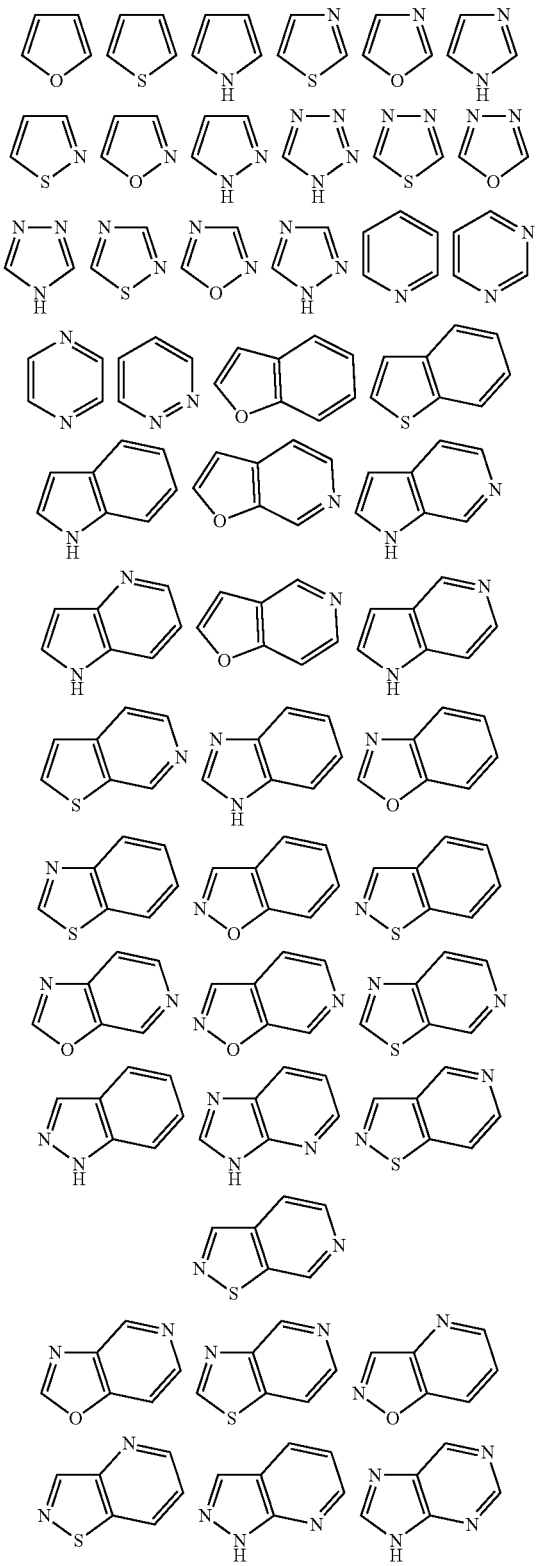

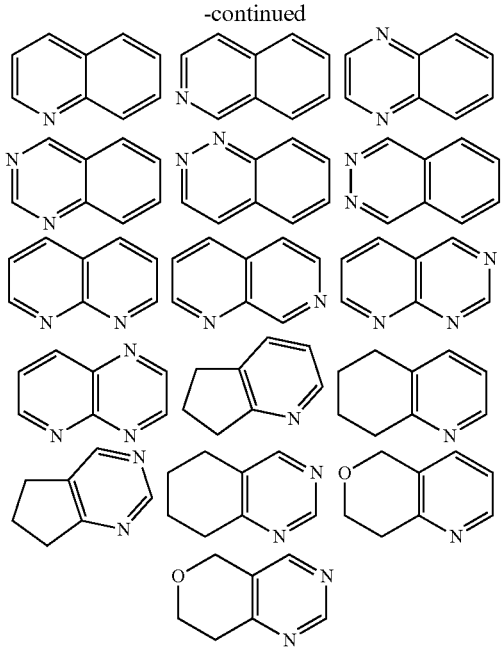

The "3- to 7-membered non-aromatic heterocyclyl" means 3- to 7-membered cyclic group having one heteroatom selected from nitrogen, oxygen, or sulfur atom, or the same or different and two or more (for example, 2 to 4, preferably 2 to 3) heteroatoms thereof, besides carbon atoms as the ring atoms. The heterocyclyl is non-aromatic, which may be a saturated one or a partially-unsaturated one. Preferred one thereof is a saturated heterocyclyl, more preferably 5- or 6-membered saturated heterocyclyl. The "3- to 7-membered non-aromatic heterocyclyl" includes, for example, oxetanyl, azetidinyl, pyranyl, tetrahydrofuryl, pyrrolidinyl, pyrazolidinyl, imidazolidinyl, piperidinyl, morpholinyl, thiomorpholinyl, dioxothiomorpholinyl, hexamethyleneiminyl, oxazolidinyl, thiazolidinyl, imidazolidinyl, oxoimidazolidinyl, dioxoimidazolidinyl, oxo-oxazolidinyl, dioxo-oxazolidinyl, dioxothiazolidinyl, tetrahydropyranyl, and tetrahydropyridinyl, and preferably pyranyl, tetrahydrofuryl, pyrrolidinyl, piperidinyl, and morpholinyl.

The "3- to 7-membered non-aromatic heterocyclyl" also includes a condensed ring in which the 3- to 7-membered non-aromatic heterocyclyl is fused with benzene or a 6-membered heteroaryl (for example, pyridine, pyrimidine or pyridazine) The examples thereof include dihydroindolyl, dihydroisoindolyl, dihydropurinyl, dihydrothiazolopyrimidinyl, dihydrobenzodioxanyl, isoindolinyl, indazolyl, pyrrolopyridinyl, tetrahydroquinolinyl, decahydroquinolinyl, tetrahydroisoquinolinyl, decahydroisoquinolinyl, tetrahydronaphthyridinyl, and tetrahydropyrido-azepinyl.

The "$C_{1-2}$ alkoxy" means oxy group substituted with the above "$C_{1-2}$ alkyl", and the "$C_{1-4}$ alkoxy" means oxy group substituted with the above "$C_{1-4}$ alkyl". The "$C_{1-2}$ alkoxy" includes, for example, methoxy and ethoxy, and the "$C_{1-4}$ alkoxy" includes, for example, propoxy, isopropoxy, butoxy, isobutoxy, sec-butoxy, and tert-butoxy, besides the above examples. Preferably, the "$C_{1-4}$ alkoxy" includes methoxy, ethoxy, and isopropoxy.

The "$C_{3-7}$ cycloalkoxy" means oxy group substituted with the above "$C_{3-7}$ cycloalkyl". The "$C_{3-7}$ cycloalkoxy" includes, for example, cyclopropyloxy, cyclobutyloxy, cyclopentyloxy, and cyclohexyloxy, and preferably cyclohexyloxy. The "$C_{5-6}$ cycloalkoxy" means a cycloalkoxy having 5 or 6 carbon atoms within the "$C_{3-7}$ cycloalkoxy".

The "$C_{6-10}$ aryloxy" means oxy group substituted with the above "$C_{6-10}$ aryl". The "$C_{6-10}$ aryloxy" includes, for example, phenyloxy and naphthyloxy, and preferably phenyloxy.

The "5- to 12-membered heteroaryloxy" means oxy group substituted with the above "5- to 12-membered heteroaryl". The "5- to 12-membered heteroaryloxy" includes, for example, pyridyloxy, imidazolyloxy and furyloxy, and preferably pyridyloxy.

The "$C_{1-4}$ alkylamino" means amino group substituted with one or two of the above "$C_{1-4}$ alkyl". The "$C_{1-4}$ alkylamino" includes, for example, methylamino, ethylamino, propylamino, isopropylamino, butylamino, isobutylamino, dimethylamino, diethylamino, and ethylmethylamino, and preferably methylamino and dimethylamino.

The "$C_{3-7}$ cycloalkylamino" means amino group substituted with one or two of the above "$C_{3-7}$ cycloalkyl". The "$C_{3-7}$ cycloalkylamino" includes, for example, cyclopropylamino, cyclobutylamino, cyclopentylamino, cyclohexylamino and dicyclopropylamino, and preferably cyclohexylamino.

The "$C_{1-4}$ alkylsulfonyl" means sulfonyl group substituted with the above "$C_{1-4}$ alkyl". The "$C_{1-4}$ alkylsulfonyl" includes, for example, methylsulfonyl, ethylsulfonyl, propylsulfonyl, isopropylsulfonyl and butylsulfonyl, and preferably methylsulfonyl.

The "$C_{1-4}$ alkylthio" means thio group substituted with the above "$C_{1-4}$ alkyl". The "$C_{1-4}$ alkylthio" includes, for example, methylthio, ethylthio, propylthio, isopropylthio and butylthio, and preferably methylthio.

In order to disclose the present compound of the above formula (I) in more detail, each symbol used in the present invention is further explained below showing preferred examples.

Preferably, $R^{1a}$, $R^{1b}$, $R^{1c}$, and $R^{1d}$ include independently hydrogen, halogen, cyano, $C_{1-4}$ alkyl, $C_{1-4}$ alkoxy, $C_{1-4}$ alkylamino, (wherein each alkyl moiety of the alkyl, the alkoxy and the alkylamino may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, $C_{3-7}$ cycloalkoxy, $C_{3-7}$ cycloalkylamino, (wherein each cycloalkyl moiety of the cycloalkyl, the cycloalkoxy and the cycloalkylamino may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), $C_{6-10}$ aryl, $C_{6-10}$ aryloxy, 5- to 12-membered heteroaryl, and 5- to 12-membered heteroaryloxy, (wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy.

More preferably, $R^{1a}$, $R^{1b}$, $R^{1c}$, and $R^{1d}$ include independently hydrogen, halogen, cyano, $C_{1-4}$ alkyl, $C_{1-4}$ alkoxy, (wherein each alkyl moiety of the alkyl and the alkoxy may be independently substituted with the same or different and 1 to 3 halogens), $C_{6-10}$ aryl, $C_{6-10}$ aryloxy, 5- to 12-membered heteroaryl, and 5- to 12-membered heteroaryloxy, (wherein each aryl moiety of the aryl and the aryloxy and each heteroaryl moiety of the heteroaryl and the heteroaryloxy may be independently substituted with 1 to 3 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, and $C_{1-4}$ alkylsulfonyl optionally-substituted with 1 to 3 substituents selected independently from Substituent-group A), provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy.

Even more preferably, $R^{1a}$ and $R^{1d}$ include hydrogen, and $R^{1b}$ and $R^{1c}$ are independently hydrogen, $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen and optionally-substituted $C_{1-4}$ alkyl, provided that both of $R^{1b}$ and $R^{1c}$ are not hydrogen.

In another embodiment of $R^{1a}$, $R^{1b}$, $R^{1c}$, and $R^{1d}$; $R^{1a}$ and $R^{1d}$ are hydrogen, and $R^{1b}$ and $R^{1c}$ are independently hydrogen, $C_{6-10}$ aryloxy, or 5- to 12-membered heteroaryloxy, wherein the aryl moiety of the aryloxy and the heteroaryl moiety of the heteroaryloxy may be independently substituted with 1 to 3 substituents selected independently from the group consisting of halogen and optionally-substituted $C_{1-4}$ alkyl, provided that both of $R^{1b}$ and $R^{1c}$ are not hydrogen.

In another embodiment of $R^{1a}$, $R^{1b}$, $R^{1c}$, and $R^{1d}$; $R^{1a}$ and $R^{1d}$ are hydrogen, and $R^{1b}$ and $R^{1c}$ are independently hydrogen, $C_{6-10}$ aryl, or 5- to 12-membered heteroaryl, wherein the aryl and the heteroaryl may be independently substituted with 1 to 3 substituents selected independently from the group consisting of halogen and optionally-substituted $C_{1-4}$ alkyl, provided that both of $R^{1b}$ and $R^{1c}$ are not hydrogen.

In another embodiment of $R^{1a}$, $R^{1b}$, $R^{1c}$, and $R^{1d}$;
$R^{1a}$ and $R^{1d}$ are hydrogen,
one of $R^{1b}$ and $R^{1c}$ is $C_{6-10}$ aryloxy or 5- to 12-membered heteroaryloxy, wherein the aryl moiety of the aryloxy and the heteroaryl moiety of the heteroaryloxy may be independently substituted with 1 to 3 substituents selected independently from the group consisting of halogen and optionally-substituted $C_{1-4}$ alkyl, and the other is hydrogen.

In another embodiment of $R^{1a}$, $R^{1b}$, $R^{1c}$, and $R^{1d}$; $R^{1a}$ and $R^{1d}$ are hydrogen, one of $R^{1b}$ and $R^{1c}$ is $C_{6-10}$ aryl or 5- to 12-membered heteroaryl, wherein the aryl and the heteroaryl may be independently substituted with 1 to 3 substituents selected independently from the group consisting of halogen and optionally-substituted $C_{1-4}$ alkyl, and the other is hydrogen.

Preferred examples of $R^{1a}$, $R^{1b}$, $R^{1c}$, and $R^{1d}$ include hydrogen, fluorine, chlorine, methyl, ethyl, isopropyl, isobutyl, cyclopropyl, cyclopentyl, cyclohexyl, methoxy, ethoxy, phenyl, 2-fluorophenyl, 3-fluorophenyl, 4-fluorophenyl, 4-(trifluoromethyl)phenyl, 5-(trifluoromethyl)pyridin-2-yl, phenoxy, 3-fluorophenoxy, 4-fluorophenoxy, 3,4-difluorophenoxy, 3,5-difluorophenoxy, 4-chlorophenoxy, 4-methylphenoxy, 4-(trifluoromethyl)phenoxy, 4-methoxyphenoxy, 4-(trifluoromethoxy)phenoxy, 4-cyanophenoxy, 4-(methylsulfonyl)phenoxy, (5-methylpyridin-2-yl)oxy, (5-(trifluoromethyl)pyridin-2-yl)oxy, and (5-fluoropyridin-2-yl)oxy.

More preferred examples of $R^{1a}$, $R^{1b}$, $R^{1c}$, and $R^{1d}$ include hydrogen, fluorine, chlorine, methyl, ethyl, isopropyl, isobutyl, cyclopropyl, cyclopentyl, cyclohexyl, methoxy, ethoxy, phenyl, 4-fluorophenyl, 4-(trifluoromethyl)phenyl, 5-(trifluoromethyl)pyridin-2-yl, phenoxy, 3-fluorophenoxy, 4-fluorophenoxy, 3,4-difluorophenoxy, 3,5-difluorophenoxy, 4-chlorophenoxy, 4-methylphenoxy, 4-(trifluoromethyl) phenoxy, 4-methoxyphenoxy, 4-(trifluoromethoxy) phenoxy, 4-cyanophenoxy, 4-(methylsulfonyl) phenoxy, (5-methylpyridin-2-yl)oxy, (5-(trifluoromethyl) pyridin-2-yl)oxy, and (5-fluoropyridin-2-yl)oxy.

Even more preferred examples of $R^{1a}$, $R^{1b}$, $R^{1c}$, and $R^{1d}$ include hydrogen, fluorine, 4-(trifluoromethyl)phenyl, 5-(trifluoromethyl)pyridin-2-yl, 3-fluorophenoxy, 4-fluorophenoxy, 4-chlorophenoxy, 4-methylphenoxy, 4-(trifluoromethyl)phenoxy, 4-(trifluoromethoxy)phenoxy, (5-methylpyridin-2-yl)oxy, and (5-(trifluoromethyl)pyridin-2-yl)oxy.

Other embodiments of $R^{1a}$, $R^{1b}$, $R^{1c}$, and $R^{1d}$ include hydrogen, fluorine, chlorine, methyl, ethyl, isopropyl, isobutyl, cyclopropyl, cyclopentyl, cyclohexyl, methoxy, ethoxy, phenyl, 2-fluorophenyl, 3-fluorophenyl, 4-fluorophenyl, 4-(trifluoromethyl)phenyl, 5-(trifluoromethyl)pyridin-2-yl, phenoxy, 3-fluorophenoxy, 4-fluorophenoxy, 3,4-difluorophenoxy, 3,5-difluorophenoxy, 4-chlorophenoxy, 4-methylphenoxy, 4-(trifluoromethyl)phenoxy, 4-methoxyphenoxy, 4-(trifluoromethoxy)phenoxy, 4-cyanophenoxy, 4-(methylsulfonyl)phenoxy, (5-methylpyridin-2-yl)oxy, (5-(trifluoromethyl)pyridin-2-yl)oxy, (5-fluoropyridin-2-yl)oxy, 2-methoxy-4-(trifluoromethyl)phenyl, 2-fluoro-4-(trifluoromethyl)phenyl, 2-chloro-4-(trifluoromethyl)phenyl, 4-(trifluoromethoxy)phenyl, (5-chloropyridin-2-yl)oxy, 2,4-dichlorophenyl, 2-chloro-4-fluorophenyl, 4-chloro-2-fluorophenoxy, and 2,4-dichlorophenoxy.

Other embodiments of $R^{1a}$, $R^{1b}$, $R^{1c}$, and $R^{1d}$ include hydrogen, fluorine, 4-(trifluoromethyl)phenyl, 5-(trifluoromethyl)pyridin-2-yl, 3-fluorophenoxy, 4-fluorophenoxy, 4-chlorophenoxy, 4-methylphenoxy, 4-(trifluoromethyl)phenoxy, 4-(trifluoromethoxy)phenoxy, (5-methylpyridin-2-yl)oxy, (5-(trifluoromethyl)pyridin-2-yl)oxy, 2-methoxy-4-(trifluoromethyl)phenyl, 4-(trifluoromethoxy)phenyl, and (5-chloropyridin-2-yl)oxy.

Preferably, $R^2$ and $R^3$ include hydrogen and $C_{1-6}$ alkyl which may be substituted with 1 to 5 substituents selected independently from the group consisting of cyano, halogen, hydroxyl, and $C_{1-4}$ alkoxy optionally-substituted with 1 to 3 substituents selected independently from Substituent-group A, and more preferably hydrogen and $C_{1-6}$ alkyl optionally-substituted with 1 to 5 halogens.

Preferred examples of $R^2$ and $R^3$ include hydrogen, methyl, ethyl, isopropyl, isobutyl, trifluoromethyl, cyclopropyl, cyclopentyl, and cyclohexyl, and more preferably hydrogen, methyl, and ethyl.

And, $R^2$ and $R^3$ may be combined together with the carbon atom to which they are attached to form the following group of formula (II) with —$OR^4$.

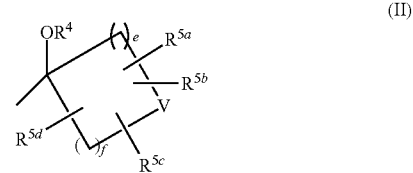

(II)

In the above formula (II), preferably e and f are independently 1 or 2.

Preferably, $R^{5a}$, $R^{5b}$, $R^{5c}$, and $R^{5d}$ are independently hydrogen or halogen.

And, $R^2$ and $R^7$ may be combined together with the carbon atom to which they are attached to form the following group of formula (IV) with $R^3$, —$OR^4$ and $R^8$.

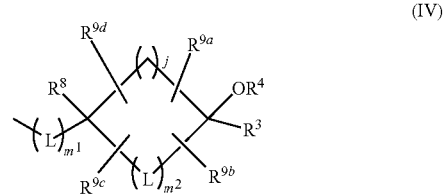

(IV)

In the above formula (IV), preferably $m^1$ is 0, and preferably $m^2$ is 1 or 2.

Preferably, j is 1, 2 or 3.

Preferably, $R^{9a}$, $R^{9b}$, $R^{9c}$, and $R^{9d}$ are independently hydrogen or halogen.

Preferably, $R^4$ is hydrogen.

Preferably, $R^4$ is hydrogen, $C_{1-4}$ alkyl which may be substituted with the same or different and 1 to 3 halogens, or $C_{3-7}$ cycloalkyl which may be substituted with 1 to 3 substituents selected independently from the group consisting of halogen, hydroxyl, and $C_{1-4}$ alkoxy optionally-substituted with 1 to 3 substituents selected independently from Substituent-group A, and more preferably hydrogen.

Preferred examples of $R^4$ include hydrogen, methyl, ethyl, propyl, isopropyl, cyclopropyl, cyclobutyl, cyclopentyl, and cyclohexyl, and more preferably hydrogen, isopropyl, and cyclopentyl, and even more preferably hydrogen.

And, $R^3$ and —$OR^4$ may be combined together with the carbon atom to which they are attached to form the following group of formula (III) with $R^2$.

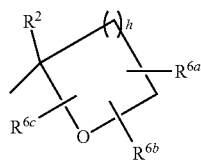

(III)

In the above formula (III), preferably h is 1, 2 or 3, and more preferably 2 or 3.

Preferably, $R^{6a}$, $R^{6b}$ and $R^{6c}$ are independently hydrogen, halogen, or $C_{1-4}$ alkyl optionally-substituted with the same or different and 1 to 3 halogens, and more preferably hydrogen.

Preferred examples of $R^{6a}$, $R^{6b}$ and $R^{6c}$ include hydrogen, fluorine, hydroxyl, methyl, trifluoromethyl, methoxy, ethoxy, and trifluoromethoxy, and more preferably hydrogen, fluorine, and methyl, and even more preferably hydrogen.

Preferably, m is 1 or 2, and more preferably 1.

L is $CR^7R^8$ provided that when m is 2 or 3, each $CR^7R^8$ are independently the same or different.

Preferably, $R^7$ and $R^8$ include hydrogen and $C_{1-4}$ alkyl which may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, and more preferably hydrogen.

Preferred examples of $R^7$ and $R^8$ include hydrogen, methyl, and ethyl, and more preferably hydrogen.

Preferably, Substituent-group A includes fluorine, chlorine, hydroxyl, $C_{1-2}$ alkoxy, and $C_{5-6}$ cycloalkoxy, and more preferably fluorine, hydroxyl, and $C_{1-2}$ alkoxy.

Preferably, Substituent-group B includes fluorine, chlorine, hydroxyl, $C_{1-2}$ alkyl, $C_{1-2}$ alkoxy, and $C_{5-6}$ cycloalkoxy, and more preferably fluorine, hydroxyl, $C_{1-2}$ alkyl, and $C_{1-2}$ alkoxy.

An embodiment of the compound of formula (I) includes the following compound or a pharmaceutically acceptable salt thereof:

$R^{1a}$, $R^{1b}$, $R^{1c}$, and $R^{1d}$ are independently, hydrogen, $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen and $C_{1-4}$ alkyl optionally-substituted with 1 to 3 substituents selected independently from Substituent-group A, provided that at least one of $R^{1a}$, $R^{1b}$, $R^{1c}$ and $R^{1d}$ is the above $C_{6-10}$ aryl, $C_{6-10}$ aryloxy, 5- to 12-membered heteroaryl or 5- to 12-membered heteroaryloxy, $R^2$ and $R^3$ are independently hydrogen or $C_{1-6}$ alkyl which may be independently substituted with 1 to 5 substituents selected independently from the group consisting of cyano, halogen, hydroxyl, and $C_{1-4}$ alkoxy optionally-substituted with 1 to 3 substituents selected independently from Substituent-group A, provided that both of $R^2$ and $R^3$ are not hydrogen, or $R^2$ and $R^3$ may be combined together with the carbon atom to which they are attached to form the following group of formula (IIa) with —$OR^4$

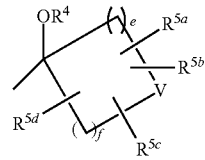

(IIa)

in formula (IIa), e and f are independently 1 or 2, $R^4$ is hydrogen, $C_{1-6}$ alkyl which may be substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $C_{3-7}$ cycloalkyl which may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, V is single bond or oxygen atom, $R^{5a}$, $R^{5b}$, $R^{5c}$, and $R^{5d}$ are independently hydrogen or halogen, or in $R^2$, $R^3$, —$OR^4$ and $CR^7R^8$ in L, $R^2$ and $R^7$ may be combined together with the carbon atom to which they are attached to form the following group of formula (IVa) with $R^3$, —$OR^4$ and $R^8$

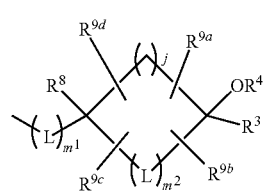

(IVa)

in formula (IVa), $m^1$ is 0, $m^2$ is 1 or 2, j is 1, 2 or 3, $R^3$ is hydrogen or $C_{1-6}$ alkyl optionally-substituted with 1 to 3 halogens, $R^4$ is hydrogen or $C_{3-7}$ cycloalkyl optionally-substituted with 1 to 3 halogens, $R^8$ is hydrogen, hydroxyl, $C_{1-4}$ alkyl, $C_{1-4}$ alkoxy (wherein each alkyl moiety of the alkyl and the alkoxy may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B), $C_{3-7}$ cycloalkyl, or $C_{3-7}$ cycloalkoxy, (wherein each cycloalkyl moiety of the cycloalkyl and the cycloalkoxy may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B), L is $CR^7R^8$, provided that when m is 2, each $CR^7R^8$ are independently the same or different, $R^{9a}$, $R^{9b}$, $R^{9c}$, and $R^{9d}$ are independently hydrogen or halogen, $R^4$ is hydrogen, $C_{1-4}$ alkyl optionally-substituted with the same or different and 1 to 3 halogens, or $C_{3-7}$ cycloalkyl which may be substituted with 1 to 3 substituents selected independently from the group consisting of halogen, hydroxyl, and $C_{1-4}$ alkoxy optionally-substituted with 1 to 3 substituents selected independently from Substituent-group A, or $R^3$ and —$OR^4$ may be combined together with the carbon atom to which they are attached to form the following group of formula (IIIa) with $R^2$

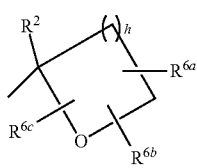

(IIIa)

in formula (IIIa), h is 1, 2 or 3, $R^2$ is hydrogen, $C_{1-6}$ alkyl which may be independently substituted with 1 to 5 substituents selected independently from the group consisting of cyano, halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, or $C_{3-10}$ cycloalkyl, $R^{6a}$, $R^{6b}$, and $R^{6c}$ are independently hydrogen, halogen, or $C_{1-4}$ alkyl optionally-substituted with the same or different and 1 to 3 halogens, m is 1 or 2, L is $CR^7R^8$, provided that when m is 2, each $CR^7R^8$ are independently the same or different, $R^7$ and $R^8$ are independently hydrogen or $C_{1-4}$ alkyl which may be independently substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B.

Another embodiment of the compound of formula (I) includes the following compound or a pharmaceutically acceptable salt thereof:

$R^{1a}$ and $R^{1d}$ are hydrogen, at least one of $R^{1b}$ and $R^{1c}$ is $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen and $C_{1-4}$ alkyl optionally-substituted with 1 to 3 substituents selected independently from Substituent-group A, $R^2$ and $R^3$ are independently $C_{1-6}$ alkyl optionally-substituted with the same or different and 1 to 5 halogens, or $R^2$ and $R^3$ may be combined together with the carbon atom to which they are attached to form the following group of formula (IIb) with —$OR^4$

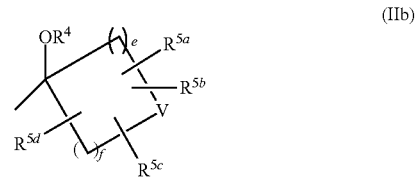

(IIb)

in formula (IIb), e and f are independently 1 or 2, $R^4$ is hydrogen, $C_{1-6}$ alkyl which may be substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $C_{3-7}$ cycloalkyl which may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, V is single bond or oxygen atom, $R^{5a}$, $R^{5b}$, $R^{5c}$, and $R^{5d}$ are independently hydrogen or halogen, or in $R^2$, $R^3$, —$OR^4$ and $CR^7R^8$ in L, $R^2$ and $R^7$ may be combined together with the carbon atom to which they are attached to form the following group of formula (IVa) with $R^3$, —$OR^4$ and $R^8$

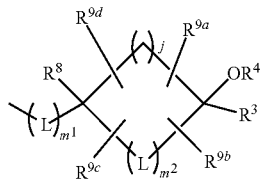

(IVa)

in formula (IVa),
$m^1$ is 0,
$m^2$ is 1 or 2,
j is 1 or 2,
$R^3$ is hydrogen or $C_{1-4}$ alkyl,
$R^4$ is hydrogen,
$R^8$ is hydrogen or $C_{1-4}$ alkyl,
L is $CR^7R^8$, provided that when m is 2, each $CR^7R^8$ are independently the same or different,
$R^{9a}$, $R^{9b}$, $R^{9c}$, and $R^{9d}$ are independently hydrogen or halogen,
$R^4$ is hydrogen, $C_{1-4}$ alkyl optionally-substituted with the same or different and 1 to 3 halogens, or $C_{3-7}$ cycloalkyl optionally-substituted with the same or different and 1 to 3 halogens, or
$R^3$ and —$OR^4$ may be combined together with the carbon atom to which they are attached to form the following group of formula (IIIa) with $R^2$

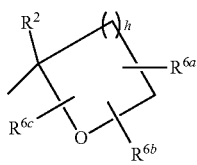

(IIIa)

in formula (IIIa),
h is 1, 2 or 3,
$R^2$ is hydrogen or $C_{1-4}$ alkyl optionally-substituted with the same or different and 1 to 3 halogens,
$R^{6a}$, $R^{6b}$, and $R^{6c}$ are independently hydrogen, halogen, or $C_{1-4}$ alkyl optionally-substituted with the same or different and 1 to 3 halogens,
m is 1 or 2,
L is $CR^7R^8$, provided that when m is 2, each $CR^7R^8$ are independently the same or different,
$R^7$ and $R^8$ are independently hydrogen or $C_{1-4}$ alkyl optionally-substituted with the same or different and 1 to 3 halogens.

Another embodiment of the compound of formula (I) includes the following compound or a pharmaceutically acceptable salt thereof:
$R^{1a}$ and $R^{1d}$ are hydrogen,
one of $R^{1b}$ and $R^{1c}$ is, phenyl, 2-fluorophenyl, 3-fluorophenyl, 4-fluorophenyl, 4-(trifluoromethyl)phenyl, 5-(trifluoromethyl)pyridin-2-yl, phenoxy, 3-fluorophenoxy, 3,4-difluorophenoxy, 3,5-difluorophenoxy, 4-chlorophenoxy, 4-(trifluoromethyl)phenoxy, 4-(trifluoromethoxy)phenoxy, 4-cyanophenoxy, 4-(methylsulfonyl)phenoxy, (5-methyl-pyridin-2-yl)oxy, (5-(trifluoromethyl)pyridin-2-yl)oxy, (5-fluoropyridin-2-yl)oxy, 2-methoxy-4-(trifluoromethyl) phenyl, 2-fluoro-4-(trifluoromethyl)phenyl, 2-chloro-4-(trifluoromethyl)phenyl, 4-(trifluoromethoxy)phenyl, (5-chloropyridin-2-yl)oxy, 2,4-dichlorophenyl, 2-chloro-4-fluorophenoxy, 4-chloro-2-fluorophenoxy, or 2,4-dichlorophenoxy, and the other is hydrogen,
both of $R^2$ and $R^3$ are methyl, or
$R^2$ and $R^3$ may be combined together with the carbon atom to which they are attached to form the following group of formula (IIc) with —$OR^4$

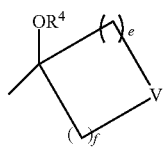

(IIc)

in formula (IIc),
e and f are independently 1 or 2,
$R^4$ is hydrogen,
V is single bond or oxygen atom, or
$R^2$ and $R^7$ may be combined together with the carbon atom to which they are attached to form the following group of formula (IVc) with $R^3$, —$OR^4$ and $R^8$

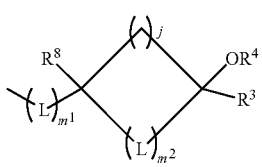

(IVc)

in formula (IVc),
$R^3$, $R^4$, and $R^8$ are hydrogen,
$m^1$ is 0,
$m^2$ is 1 or 2,
j is 1 or 2,
L is $CR^7R^8$, and
both of $R^7$ and $R^8$ are hydrogen,
$R^4$ is hydrogen, isopropyl or cyclopentyl, or
$R^3$ and —$OR^4$ may be combined together with the carbon atom to which they are attached to form the following group of formula (IIIb) with $R^2$

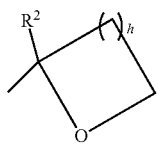

(IIIb)

in formula (IIIa),
$R^2$ is hydrogen, and
h is 2,
m is 1,
L is $CR^7R^8$, and
both of $R^7$ and $R^8$ are independently hydrogen or methyl.

Processes to prepare the compounds of the present invention are mentioned below. The compound (I) of the present invention can be prepared, for example, according to Processes 1 to 5 shown below.

Process 1:
Compound (I) wherein $R^{1b}$ is $OR^a$, i.e., Compound (S-5) or a pharmaceutically acceptable salt thereof can be prepared, for example, according to the following process.

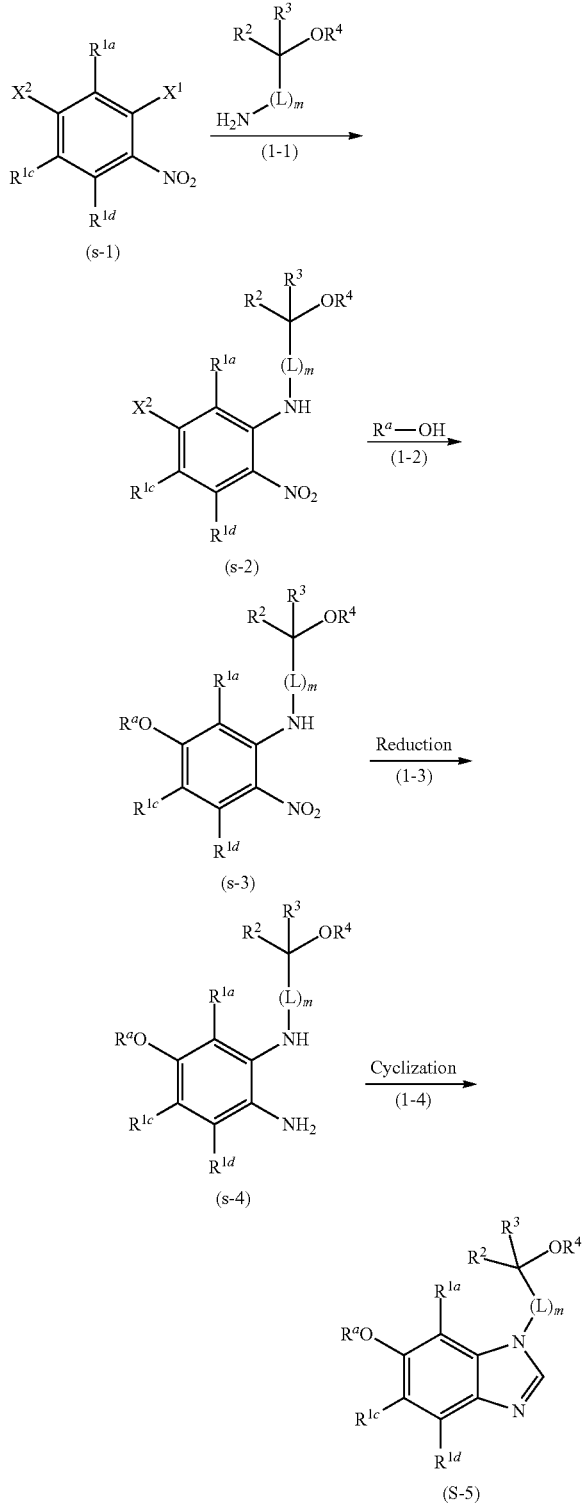

In the above scheme, $R^{1a}$, $R^{1c}$, $R^{1d}$, $R^2$, $R^3$, $R^4$, L, and m are as defined in Term 1; $R^aO$— means $R^{1b}$ which is selected from $C_{1-4}$ alkoxy optionally-substituted with 1 to 3 substituents selected independently from Substituent-group A, $C_{3-7}$ cycloalkoxy optionally-substituted with 1 to 3 substituents selected independently from Substituent-group B, $C_{6-10}$ aryloxy optionally-substituted with 1 to 3 substituents selected independently from Substituent-group B, or 5- to 12-membered heteroaryloxy optionally-substituted with 1 to 3 substituents selected independently from Substituent-group B; and $X^1$ and $X^2$ are independently a leaving group such as halogen, trifluoromethanesulfonyloxy, and methanesulfonyloxy.

Step (1-1):
This step is a process to prepare Nitroaniline compound (s-2) by reacting Nitrobenzene compound (s-1) and an amine compound. The base used herein includes an inorganic base such as sodium hydroxide, potassium hydroxide, potassium carbonate, and cesium carbonate, and an organic base such as triethylamine, diisopropylethylamine, and DABCO (1,4-diazabicyclo[2,2,2]octane). When the amine compound is used in large excess, it is not necessary to use such base. The solvent used herein includes ethers such as THF, dimethoxyethane, and 1,4-dioxane; DMF; NMP; acetonitrile; and the like. The reaction time is generally about 10 minutes to about 10 hours, and the reaction temperature is 0° C. to boiling point of a solvent used herein.

Step (1-2):
This step is a process to prepare Compound (s-3) by reacting Nitroaniline compound (s-2) and a compound having hydroxyl. The base used herein includes sodium hydroxide, potassium hydroxide, potassium carbonate, cesium carbonate, sodium hydride, and the like. The solvent used herein includes ethers such as THF, 1,2-dimethoxyethane, and 1,4-dioxane; DMF; NMP; acetonitrile; and the like. The reaction time is generally about 10 minutes to about 10 hours, and the reaction temperature is 0° C. to boiling point of a solvent used herein.

Step (1-3):
This step is a process to prepare Amino compound (s-4) by reducing Nitro compound (s-3). The reaction condition of the present step includes a general condition to reduce nitro group, for example, catalytic reduction under hydrogenation with palladium-carbon or the like, metallic reduction with zinc, iron or the like, and hydride reduction with lithium aluminium hydride or the like. The solvent used herein may be chosen from generally-used solvents depending on each reduction condition, and includes methanol, ethanol, THF, ethyl acetate, or the like for catalytic reduction; THF, acetic acid, methanol, ethanol, or the like for metallic reduction; and diethyl ether, THF, or the like for hydride reduction. The reaction time is generally about 10 minutes to about 24 hours, and the reaction temperature is 0° C. to boiling point of a solvent used herein.

Step (1-4):
This step is a process to prepare Compound (S-5) by reacting Phenylenediamine compound (s-4) and formic acid or a formic acid equivalent to be cyclized. The formic acid equivalent includes orthoformates such as methyl orthoformate and ethyl orthoformate. In the present step, a catalyst may be used, which includes an organic acid such as formic acid and acetic acid, and Lewis acid such as ytterbium triflate. The solvent used herein includes alcohols such as methanol and ethanol. It is also possible to use formic acid, orthoformate and the like as a solvent, which are mentioned above as a reactant. The reaction time is generally about 10 minutes to about 24 hours, and the reaction temperature is room temperature to boiling point of a solvent used herein.

Compound (I) wherein any one or more of $R^{1a}$, $R^{1b}$, $R^{1c}$ and $R^{1d}$ is $OR^a$ or a pharmaceutically acceptable salt thereof can be also prepared in a similar manner as the above process.

Process 2:

Compound (I) wherein $R^4$ is $R^{4a}$ (alkyl or cycloalkyl), i.e., Compound (S-7) or a pharmaceutically acceptable salt thereof can be prepared, for example, according to the following process.

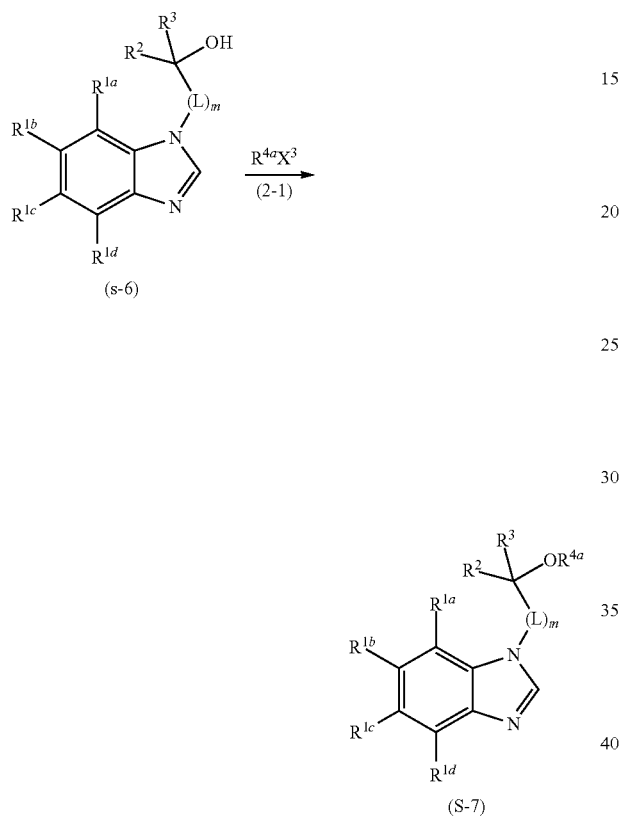

In the above scheme, $R^{1a}$, $R^{1b}$, $R^{1c}$, $R^{1d}$, $R^2$, $R^3$, L, and m are as defined in Term 1; $X^3$ is the same definition as the above $X^1$; and $R^{4a}$ is the same as $R^4$, provided that hydrogen is excluded.

Step (2-1):

This step is a process to prepare Ether compound (S-7) by reacting Alcohol compound (s-6) which is Compound (s-5) wherein $R^4$ is hydrogen, and, for example, a compound of $R^{4a}X^3$ in the presence of a base. The base used herein includes sodium hydride, potassium hydride, lithium hydride, butyllithium, potassium butoxide, and the like. The solvent used herein includes ethers such as diethyl ether and THF; DMF; NMP; dimethyl sulfoxide; and the like. The reaction time is generally about 10 minutes to about 24 hours, and the reaction temperature is 0° C. to boiling point of a solvent used herein.

Process 3:

Compound (I) wherein $R^{1b}$ is $R^b$ (aryl or heteroaryl), i.e., Compound (S-10) or a pharmaceutically acceptable salt thereof can be prepared, for example, according to the following process.

In the above scheme, $R^{1a}$, $R^{1c}$, $R^{1d}$, $R^2$, $R^3$, $R^4$, L, and m are as defined in Term 1; $X^2$ is as defined above; and $R^b$ is $C_{6-10}$ aryl or 5- to 12-membered heteroaryl, wherein the aryl and the heteroaryl may be independently substituted with 1 to 5 substituents selected independently from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A.

Step (3-1):

This step is a process to prepare Amino compound (s-8) by selectively reducing the nitro group in Nitrobenzene compound (s-2). The reaction condition of the present step includes catalytic reduction under hydrogenation with sulfur-poisoning platinum-carbon or the like; metallic reduction with zinc, iron, tin or the like; and hydride reduction with lithium aluminium hydride or the like. The solvent used herein may be chosen from generally-used solvents depending on each reduction condition, and includes methanol, ethanol, THF, ethyl acetate, or the like for catalytic reduction; THF, acetic acid, methanol, ethanol, or the like for metallic reduction; and diethyl ether, THF, or the like for hydride reduction. The reaction time is generally about 10 minutes to about 24 hours, and the reaction temperature is 0° C. to boiling point of a solvent used herein.

Step (3-2):

This step is a process to prepare Compound (s-9) by treating Amino compound (s-8) in a similar manner of Step (1-4).

Step (3-3):

This step is a process to prepare Compound (S-10) by reacting Compound (s-9) and a boronic acid compound having $R^b$ group or its ester compound in the presence of a base and a catalyst. Specifically, this step is a process by means of Suzuki coupling reaction. The base used herein includes sodium carbonate, potassium carbonate, cesium carbonate, tripotassium phosphate, and the like. The catalyst used herein includes palladium acetate, tetrakis(triphenylphosphine)palladium, tris(dibenzylideneacetone)dipalladium, and the like.

The solvent used herein includes 1,4-dioxane, toluene, 1,2-dimethoxyethane, and the like. The reaction time is generally about 30 minutes to about 24 hours, and the reaction temperature is room temperature to boiling point of a solvent used herein.

Compound (I) wherein any one or more of $R^{1a}$, $R^{1b}$, $R^{1c}$ and $R^{1d}$ is $R^b$ or a pharmaceutically acceptable salt thereof can be also prepared in a similar manner as the above process.

Process 4:

Compound (I) wherein $R^{1b}$ is $R^b$, i.e., Compound (S-10) or a pharmaceutically acceptable salt thereof can be also prepared, for example, according to the following process.

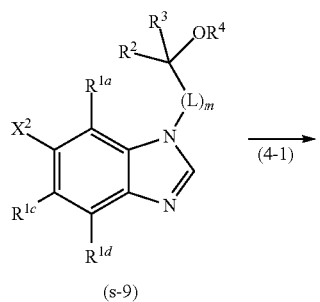

(s-9)

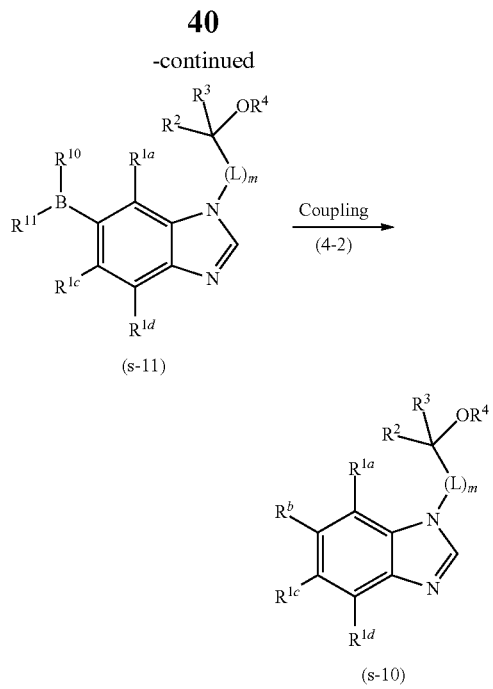

In the above scheme, $R^{1a}$, $R^{1c}$, $R^{1d}$, $R^2$, $R^3$, $R^4$, L, and m are as defined in Term 1; $R^b$ and $X^2$ are as defined above; and $R^{10}$ and $R^{11}$ are independently optionally-substituted $C_{1-4}$ alkyl, optionally-substituted $C_{1-4}$ alkoxy, optionally-substituted $C_{1-4}$ dialkylamino, optionally-substituted $C_{6-10}$ aryl, optionally-substituted $C_{6-10}$ aryloxy, optionally-substituted 5- to 12-membered heteroaryl, optionally-substituted 5- to 12-membered heteroaryloxy, or hydroxyl. Preferably, $R^{10}R^{11}B-$ includes the following structures, but not limited thereto.

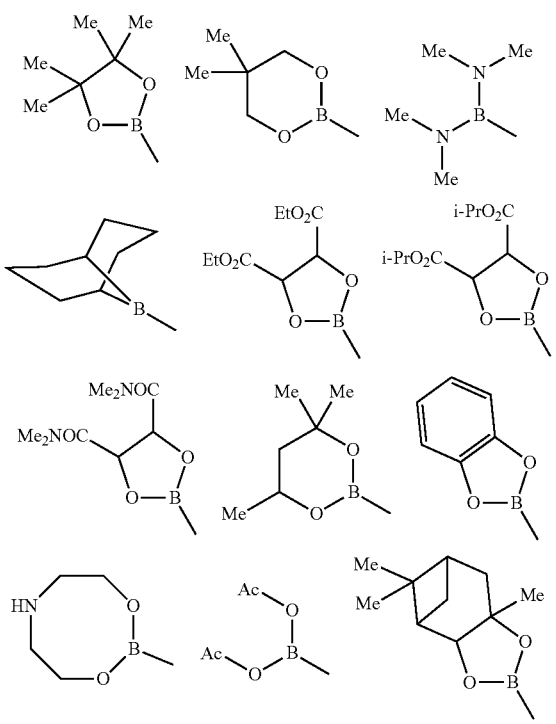

41
-continued

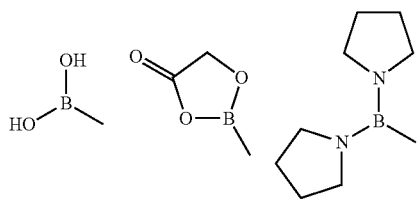

Step (4-1):

This step is a process to prepare Boronate ester compound (s-11) by reacting Compound (s-9) and a diboron compound such as bis(pinacolato)diboron in the presence of a catalyst and a base. The catalyst used herein includes dichloro[1,1'-bis(diphenylphosphino)ferrocene]palladium, tetrakis(triphenylphosphine)palladium, tris(dibenzylideneacetone)dipalladium, bis(triphenylphosphine)palladium dichloride, and the like. The base used herein includes potassium acetate, tripotassium phosphate, potassium carbonate, and the like. The solvent used herein includes 1,4-dioxane, toluene, 1,2-dimethoxyethane, and the like. The reaction time is generally about 1 hour to about 48 hours, and the reaction temperature is room temperature to boiling point of a solvent used herein.

Step (4-2):

This step is a process to prepare Compound (S-10) by reacting Boronate ester compound (s-11) and a halide compound having $R^b$ group or a triflate compound having $R^b$ group (such as $R^b$—X (X: halogen atom) or $CF_3SO_2O$—$R^b$) in the presence of a catalyst and a base. Specifically, this step is a process by means of Suzuki coupling reaction. The base used herein includes sodium carbonate, potassium carbonate, cesium carbonate, tripotassium phosphate, and the like. The catalyst used herein includes palladium acetate, tetrakis(triphenylphosphine)palladium, tris(dibenzylideneacetone) dipalladium, and the like. The solvent used herein includes 1,4-dioxane, toluene, 1,2-dimethoxyethane, and the like. The reaction time is generally about 30 minutes to about 48 hours, and the reaction temperature is room temperature to boiling point of a solvent used herein.

Compound (I) wherein any one or more of $R^{1a}$, $R^{1b}$, $R^{1c}$ and $R^{1d}$ is $R^b$ or a pharmaceutically acceptable salt thereof can be also prepared in a similar manner as the above process.

Process 5:

Compound (I) wherein $R^{1b}$ is $OR^a$, i.e., Compound (S-5) or a pharmaceutically acceptable salt thereof can be also prepared, for example, according to the following process.

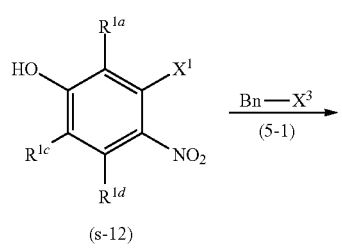

42
-continued

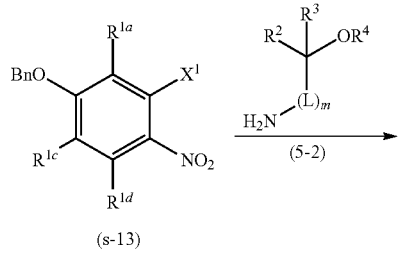

(s-13)

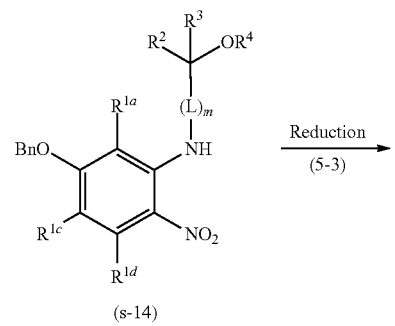

(s-14)

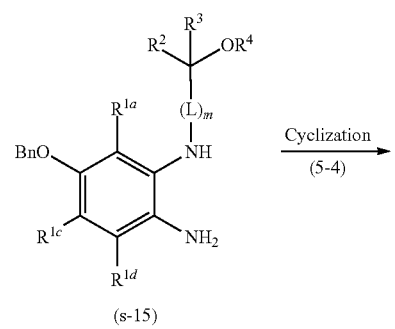

(s-15)

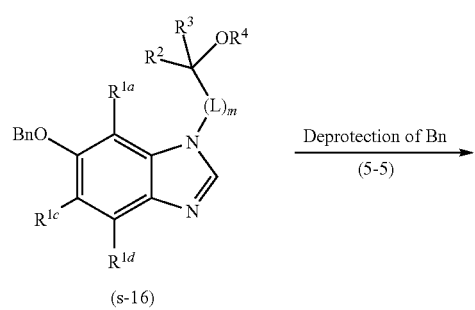

(s-16)

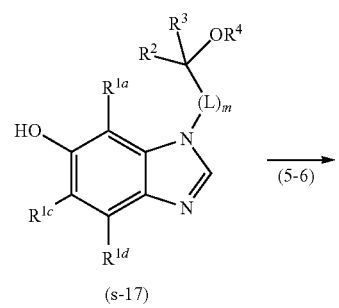

(s-17)

-continued

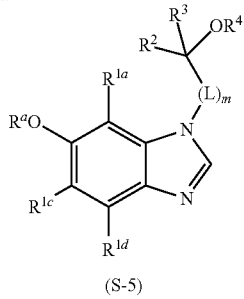

(S-5)

In the above scheme, $R^{1a}$, $R^{1c}$, $R^{1d}$, $R^2$, $R^3$, $R^4$, L, and m are as defined in Term 1; and $R^a$, $X^1$ and $X^3$ are as defined above. Bn means benzyl group. Instead of benzyl group, similar protective group to benzyl group may be also used, for example, substituted benzyl group which is disclosed in Protective Groups in Organic Synthesis.

Step (5-1):

This step is a process to prepare Compound (s-13), for example, by reacting Compound (s-12) with Bn-$X^3$ in the presence of a base. The base used herein includes sodium carbonate, potassium carbonate, cesium carbonate, sodium hydride, and the like. Bn-$X^3$ may include benzyl chloride, benzyl bromide and the like. As appropriate, sodium iodide, potassium iodide, tetrabutylammonium iodide, tetrabutylammonium hydrogen sulfate, or the like may be added thereto. The solvent used herein includes acetone, acetonitrile, THF, diethyl ether, 1,4-dioxane, 1,2-dimethoxyethane, DMF, NMP, and the like. The reaction time is generally about 30 minutes to about 24 hours, and the reaction temperature is 0° C. to boiling point of a solvent used herein. In addition, Compound (s-13) can be also prepared from Compound (s-12) according to the method (condition) disclosed in Protective Groups in Organic Synthesis and such.

Step (5-2):

This step is a process to prepare Compound (s-14) from Compound (s-13) in a similar manner of Step (1-1).

Step (5-3):

This step is a process to prepare Compound (s-15) from Compound (s-14) in a similar manner of Step (3-1) (i.e., a manner to selectively reduce a nitro group).

Step (5-4):

This step is a process to prepare Compound (s-16) from Compound (s-15) in a similar manner of Step (1-4).

Step (5-5):

This step is a process to prepare Compound (s-17), for example, by hydrogenating Compound (s-16) to deprotect it to the hydroxyl group. The catalyst used herein is a heterogenous catalyst such as palladium-carbon. The condition of hydrogenation means "under hydrogen atmosphere" or "in the presence of formic acid, ammonium formate, or the like". The solvent used herein includes methanol, ethanol, THF, ethyl acetate, and the like. The reaction time is generally about 30 minutes to about 24 hours, and the reaction temperature is 0° C. to boiling point of a solvent used herein. In addition, Compound (s-17) can be also prepared from Compound (s-16) according to the method (condition) disclosed in Protective Groups in Organic Synthesis and such.

Step (5-6):

This step is a process to prepare Compound (S-5) from Compound (s-17), which includes the following two reaction conditions, but not limited thereto.

1) As a reaction condition using a base, it includes a process to prepare Compound (S-5) from Compound (s-17) and $R^a$—$X^4$ wherein $R^a$ in $R^{1b}$ is $C_{1-4}$ alkyl optionally-substituted with 1 to 3 substituents selected independently from Substituent-group A, $C_{3-7}$ cycloalkyl optionally-substituted with 1 to 3 substituents selected independently from Substituent-group B, $C_{6-10}$ aryl optionally-substituted with 1 to 3 substituents selected independently from Substituent-group B, or 5- to 12-membered heteroaryl optionally-substituted with 1 to 3 substituents selected independently from Substituent-group B, and $X^4$ is the same as the above $X^1$, according to a similar reaction to Step (1-2).

2) As a reaction condition using a catalyst and a base, it includes a process of using a boronic acid compound having $R^a$ or a halogen compound having $R^a$. The catalyst used herein includes copper (II) acetate, copper (I) iodide, copper (II) oxide, and the like. The base used herein includes potassium carbonate, cesium carbonate, potassium hydroxide, triethylamine, and the like. The solvent used herein includes chloroform, 1,4-dioxane, DMF, dimethyl sulfoxide, NMP (N-methyl-2-pyrrolidinone), and the like. The reaction time is generally about 30 minutes to about 24 hours, and the reaction temperature is room temperature to boiling point of a solvent used herein.

Compound (I) wherein any one or more of $R^{1a}$, $R^{1b}$, $R^{1c}$ and $R^{1d}$ is $OR^a$ or a pharmaceutically acceptable salt thereof can be also prepared in a similar manner as the above process.

The above reduction of nitro group [Step (1-3), Step (3-1), Step (5-3)] and the subsequent cyclization [Step (1-4), Step (3-2), Step (5-4)] can be sequentially done, for example, by adding formic acid or a formic acid equivalent such as orthoformate in the reduction step (s-3) or (s-14), thus the cyclized compounds (S-5), (s-9), or (s-16) can be prepared in one step. The reaction time is 10 minutes to 12 hours, and the reaction temperature is room temperature to boiling point of a solvent used herein.

The room temperature in the above processes means specifically 10° C. to 30° C.

The starting materials and intermediates in the above processes are known compounds or can be prepared with known compounds according to a known method. In case that any functional group other than a target reaction site can be reacted or can be unsuitable in the above processes, the functional group other than the target reaction site can be protected for the reaction, and the protective group can be cleaved to give a desired compound after the reaction is completed. The protective group used herein includes, for example, a conventional protective group disclosed in the aforementioned Protective Groups in Organic Synthesis and such. Specifically, the protective group for amino group includes, for example, ethoxycarbonyl, tert-butoxycarbonyl, acetyl, benzyl, and the like; and the protective group for hydroxyl includes, for example, tri-lower alkylsilyl, acetyl, benzyl, and the like.

The introduction and cleavage of protective groups can be done by a conventional method in organic chemistry (for example, see, the aforementioned Protective Groups in Organic Synthesis), or a similar method.

By appropriately changing functional group(s) in an intermediate or final product in the above processes, it is also possible to prepare a different compound defined in the present invention. The conversion of functional group(s) can be done according to a conventional method (e.g. Comprehensive Organic Transformations, R. C. Larock (1989)).

The intermediates and desired compounds in the above processes can be isolated/purified by a purification generally-used in synthetic organic chemistry, for example, neutralization, filtration, extraction, washing, drying, concentration, recrystallization, various chromatography, etc. Some intermediates can be used in next step without any purification.

The optical isomers of the present invention can be isolated by using a known division method at an appropriate step, for example, separation with an optically-active column, and fractionated crystallization. And, it is workable to use an optically-active starting material.

The compounds of the present invention may be sometimes an optical isomer, a stereoisomer, a tautomer such as a keto-enol compound, and/or a geometric isomer, hence which include all possible isomers including the above isomers, and a mixture thereof.

The compounds of the present invention may also include the compound of formula (I), a prodrug thereof, and a pharmaceutically acceptable salt thereof, besides the above isomers. And, the compounds of the present invention or a pharmaceutically acceptable salt thereof may be in a form of an adduct with water or each solvent, hence which also include such adducts. In addition, the compounds of the present invention may also include various embodiments of the crystals and the compounds in which a part or all of atoms composing the compounds are replaced with another isotope (for example, replacing hydrogen with deuterium, and replacing $^{12}C$ with $^{14}C$).

The term "prodrug of the compound of formula (I)" used herein means a compound which can be converted to the compound of formula (I) by reacting with an enzyme, gastric acid, etc. under intravitally physiological condition, i.e., a compound which can be enzymatically oxidized, reduced, hydrolyzed, or taken somehow to be converted to the compound of formula (I), and a compound which can be hydrolyzed with gastric acid or the like to be converted to the compound of formula (I).

The "pharmaceutically acceptable salt" used herein includes, for example, a base addition salt or an acid addition salt. The base addition salt includes, for example, an alkali metal salt such as sodium salt and potassium salt; an alkaline earth metal salt such as calcium salt and magnesium salt; a water-soluble amine addition salt such as ammonium salt and N-methylglucamine (meglumine); and a lower alkanol ammonium salt of an organic amine. The acid addition salt includes, for example, hydrochloride, hydrobromide, hydroiodide, nitrate, sulfate, bisulfate, phosphate, acetate, lactate, citrate, tartrate, bitartrate, succinate, maleate, fumarate, gluconate, saccharate, benzoate, methanesulfonate, ethanesulfonate, benzene sulfonate, p-toluenesulfonate, and pamoate[1,1'-methylene-bis-(2-hydroxy-3-naphthoate)].

Salts of the present compound can be prepared, for example, in the following manners. For example, when the present compound is obtained in a salt form, the salt thereof can be prepared by directly purifying it. When the present compound is obtained in a free form, the salt thereof can be prepared by dissolving or suspending it in an appropriate organic solvent, adding a possible acid or base thereto, and then treating the obtained mixture in a general manner.

The compound of formula (I) prepared by the above processes may be isolated/purified in a conventional manner such as extraction, column chromatography, recrystallization, and reprecipitation. The extraction solvent used herein includes, for example, diethyl ether, ethyl acetate, chloroform, dichloromethane, toluene, and the like. The purification by column chromatography can be done with an acid-, basic-, or variously-chemical-treating silica gel, alumina, or the like. The elute solvent used herein includes, for example, hexane/ethyl acetate, hexane/chloroform, ethyl acetate/methanol, chloroform/methanol, acetonitrile/water, methanol/water, and the like.

The novel compounds of the present invention or a pharmaceutically acceptable salt thereof having a benzimidazole ring have a property inhibiting Nav 1.7 and thereby can be used as a medicament for treating or preventing a pain involving peripheral nerve such as C-fibres and Aδ-fibres, spontaneous pain such as numbness, burning pain, dull pain, pricking pain and shooting pain, neuropathic pain accompanied by hyperalgesia such as mechanical stimulation and cold stimulation or allodynia, nociceptive pain, inflammatory pain, small-fiber neuropathy, erythromelalgia, paroxysmal extreme pain disorder, etc. The neuropathic pain includes, for example, diabetic neuropathy, postherpetic neuralgia, chemotherapy-induced neuropathy, cancer pain, sensory nerve damage caused by viral infection in human immune deficiency syndrome, trigeminal neuralgia, complex regional pain syndrome, reflex sympathetic dystrophy, neuralgia after low back surgery, phantom limb pain, pain after spinal cord injury, persistent postoperative pain, inflammatory demyelinating polyradiculopathy, alcoholic neuropathy, entrapment peripheral neuropathy, iatrogenic neuropathy, sudden sensorineural disorder, malnutrition-induced neuropathy, radiation-induced neuropathy, radiculopathy, toxic peripheral neuropathy, traumatic peripheral neuropathy, brachial plexus avulsion injury, glossopharyngeal neuralgia, autoimmune neuropathy, and chronic cauda equina syndrome. The nociceptive pain or inflammatory pain includes low back pain, abdominal pain, chronic rheumatoid arthritis, a pain caused by osteoarthritis, myalgia, acute postoperative pain, fracture pain, pain after burn injury, and the like. In addition, the present compounds or a pharmaceutically acceptable salt thereof can be also used as a medicament for treating or preventing dysuria. The dysuria includes frequent urination, bladder pain caused by prostatic hyperplasia, and the like. Furthermore, the present compounds or a pharmaceutically acceptable salt thereof can be also used as a medicament for treating or preventing ataxia developed by suppressing abnormal nervous firing in the cerebellum in multiple sclerosis. In addition, the present compounds or a pharmaceutically acceptable salt thereof can be a drug having no side effect in heart or central nerve which is a problem in existing medication, since they have a selective inhibitory activity to Nav 1.7.

The present compounds may be administered orally, parenterally or rectally, and the daily dose can vary depending on the compound, the mode of administration, patient's condition/age, etc. For oral administration, for example, the present compounds may be administered generally in a dosage of about 0.01 to 1000 mg, preferably about 0.1 to 500 mg a day per kilogram of body weight of human or mammal and once to several times. For parenteral administration such as intravenous injection, for example, the present compounds may be administered generally in a dosage of about 0.01 to 300 mg, preferably about 1 to 100 mg per kilogram of body weight of human or mammal.

The present compounds can be orally or parenterally administered directly or as a suitable formulation comprising it. The formulation thereof may be, for example, tablet, capsule, powder, granule, liquid, suspension, injection, patch, gel patch, and the like, but not limited thereto. The formulation can be prepared with pharmaceutically acceptable additive agents in known means. The additive agents can be chosen for any purpose, including an excipient, a disintegrant, a binder, a fluidizer, a lubricant, a coating agent, a solubilizer, a solubilizing agent, a thickener, dispersant, a stabilizing agent, a sweetening agent, a flavor, and the like. Specifically, they include, for example, lactose, mannitol, microcrystalline cellulose, low-substituted hydroxypropylcellulose, cornstarch, partially-pregelatinized starch, carmellose calcium, croscarmellose sodium, hydroxypropylcellulose, hydroxypropyl methylcellulose, polyvinyl alcohol, magnesium stearate, sodium stearyl fumarate, polyethylene glycol, propylene glycol, titanium oxide, talc, and the like.

The present compounds and a pharmaceutically acceptable salt thereof may be used in combination with, for example, a non-steroidal anti-inflammatory agent such as celecoxib, Voltaren, ibuprofen, loxoprofen, acetaminophen, diclofenac and dexamethasone, and an opioid analgesic such as tramadol, morphine and oxycodone, in order to strengthen the action thereof. In addition, the present compounds and a pharmaceutically acceptable salt thereof may be also used in combination with an antiepileptic agent (such as pregabalin and carbamazepine), an aldose reductase inhibitor (such as epalrestat), a prostaglandin derivative drug (such as limaprost alfadex), an antidepressive agent (such as amitriptyline and duloxetine), an anticonvulsant agent, an anxiolytic agent, a dopamine receptor agonist, an antiparkinsonian agent, a hormone preparation, a migraine medication, an adrenergic β receptor antagonist, a drug for treating dementia, a drug for treating mood disorder, or the like. Preferred drugs used in combination with the present compound and a pharmaceutically acceptable salt thereof include an antiepileptic agent such as pregabalin and carbamazepine, an antidepressive agent such as amitriptyline and duloxetine, a narcotic analgesic such as morphine, oxycodone and tramadol, an anti-inflammatory agent such as acetaminophen, diclofenac and dexamethasone, an aldose reductase inhibitor such as epalrestat, and a prostaglandin derivative such as limaprost alfadex. In order to reduce the side effects thereof, the present compounds and a pharmaceutically acceptable salt thereof may be used in combination with an antiemetic drug and a sleep-inducing drug. The administration interval of the present compound and its concomitant drug is not limited, i.e., the concomitant drug may be administered at the same time as the present compound or at a suitable interval. Or, the present compound and its concomitant drug can be formulated into a combination drug. The dose of the combination drug can be suitably determined based on the standard of the clinically-used dose thereof. The combination ratio of the present compound and its concomitant drug can be suitably determined based on its subject patient, administration route, disease, pathology, concomitant drug, etc. For example, when the subject patient is a human being, the concomitant drug may be used in 0.01 to 1000 part by weight per part of the present compound.

EXAMPLES

The present invention is explained in more detail in the following by referring to Examples and Pharmacological tests; however, the technical scope of the present invention is not limited to such Examples and the like. The silica gel chromatography or amino silica gel column chromatography used in the working examples was a product made by YAMAZEN CORPORATION. Each compound was identified with a proton nuclear magnetic resonance spectrum ($^1$H-NMR), high-performance liquid chromatograph-mass spectrometer (LCMS), etc. $^1$H-NMR was measured with JNM-LA300 (JEOL) or JNM-AL400 (JEOL).

The condition of powder X-ray diffractometry was as follows.
Measuring set: X'pert-MPD (Spectris Co., Ltd.)
X-ray: Cu Kα$_1$/45 kV/40 mA
Entrance slit: 15 mm (Auto)/Divergence-preventing slit: 15 mm (Auto)
Sample plate: non-reflecting Si plate
Step size: 0.017°
Scanning range: 4-40° (2θ)
Integration time: 100 seconds/step
High-performance liquid chromatography-mass spectrometer: The measuring condition of LCMS is shown below, and the detected value of mass spectrography [MS (m/z)] is shown as M+H.
MS detector: ACQITY SQD
HPLC: ACQITY UPLC
Column: ACQITY BEH C18 1.7 μm, 2.1×50 mm
Flow rate: 0.75 mL/min
Wave length: 254 nm
Mobile phase: A: 0.05% aqueous formic acid
B: acetonitrile
Time Program:

| | Step time (min) | |
|---|---|---|
| 1 | 0.0-1.3 | A:B = 90:10 => 1:99 |
| 2 | 1.3-1.5 | A:B = 1:99 |
| 3 | 1.5-2.0 | A:B = 90:10 |

Unless otherwise specified, the starting material compounds, reaction reagents and solvents used herein were commercially available products or were prepared according to known methods.

In the following Examples and Pharmacological tests, abbreviations shown below may be sometimes used to simplify the description of the present specification. Me: methyl, Ac: acetyl, Ph: phenyl, THF: tetrahydrofuran, DMF: N,N-dimethylformaldehyde, NMP: N-methyl-2-pyrrolidinone, DMAP: N,N-dimethyl-4-aminopyridine, HEPES: 2-[4-(2-hydroxyethyl)-1-piperazinyl]ethanesulfonic acid, EGTA: O,O'-bis(2-aminoethyl)ethylene glycol-N,N,N',N'-tetraacetate, AD-mix-β: a mixture reagent of hydroquinidine-1,4-phthalazinediyl diether/potassium carbonate/potassium ferricyanide/potassium osmate dihydrate=2/624/624/1 (molar ratio), Pd/C: palladium/carbon, Pt—S/C: sulfur-poisoned platinum/carbon, J: coupling constant, s: singlet, d: doublet, t: triplet, q: quartet, dd: double doublet, td: 3 doublets, tt: 3 triplet, m: multiplet, br: broad.

Example 1: Preparation of 1-[6-(4-fluorophenoxy)-1H-benzimidazol-1-yl]-2-methylpropan-2-ol (Compound 1)

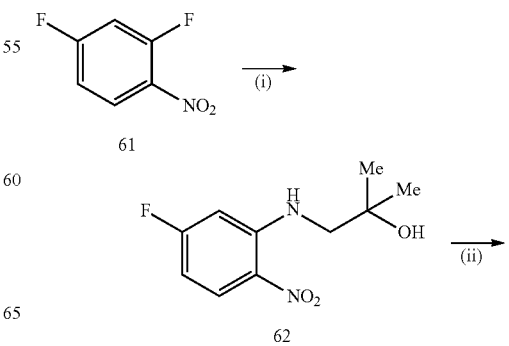

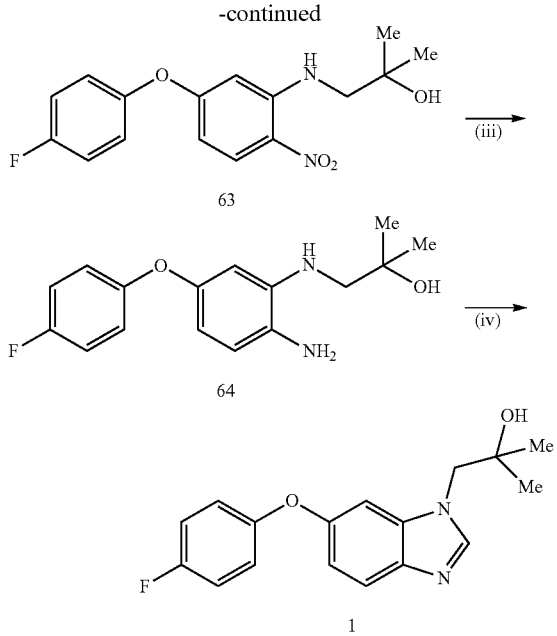

Step (i): Preparation of 1-[(5-fluoro-2-nitrophenyl)amino]-2-methylpropan-2-ol (Compound 62)

A mixture of Compound 61 (1.59 g), 1-amino-2-methylpropan-2-ol (0.98 g), diisopropylethylamine (5.22 mL), and DMF (50 mL) was stirred at 60° C. for 2 hours. To the reaction mixture were added water and a mixture of ethyl acetate/hexane (=1/1), and the objective product was extracted in the organic layer. The organic layer was dried over anhydrous sodium sulfate and then concentrated under reduced pressure to give Compound 62 as a crude product.

Step (ii): Preparation of 1-[(5-(4-fluorophenoxy)-2-nitrophenyl]amino)-2-methylpropan-2-ol (Compound 63)

A mixture of the crude product of Compound 62 prepared in Step (i), 4-fluorophenol (1.68 g), cesium carbonate (6.52 g), and NMP (25 mL) was stirred at 100° C. for 2 hours. To the reaction mixture was added water and a mixture of ethyl acetate/hexane (=1/1), and the objective product was extracted in the organic layer. The organic layer was dried over anhydrous sodium sulfate and concentrated under reduced pressure, and then the residue was purified by silica gel column chromatography (eluate: hexane/ethyl acetate=3/1) to give Compound 63 (3.10 g).

Step (iii): Preparation of 1-{[2-amino-5-(4-fluorophenoxy)phenyl]amino)-2-methylpropan-2-ol (Compound 64)

A mixture of Compound 63 (3.10 g), ammonium formate (2.95 g), 10% Pd/C (0.30 g), and methanol (47 mL) was stirred at 50° C. for 2 hours. The reaction mixture was filtered through Celite, and the filtrate was concentrated under reduced pressure. To the residue were added saturated aqueous sodium hydrogen carbonate and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=99/1) to give Compound 64 (2.70 g).

Step (iv): Preparation of 1-[6-(4-fluorophenoxy)-1H-benzimidazol-1-yl]-2-methylpropan-2-ol (Compound 1)

A mixture of Compound 64 (0.60 g), trimethyl orthoformate (1.73 mL), and p-toluenesulfonic acid monohydrate (0.079 g) was stirred at 60° C. for 1 hour. To the reaction mixture were added saturated aqueous sodium hydrogen carbonate and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=95/5) to give Compound 1 (0.41 g).

$^1$H-NMR (DMSO-d6) δ: 1.06 (6H, s), 4.08 (2H, s), 4.72 (1H, s), 6.87 (1H, m), 6.96-6.99 (2H, m), 7.17 (2H, m), 7.39 (1H, m), 7.62 (1H, m), 8.09 (1H, s).

XRD; 2θ=12.1, 13.6, 15.0, 15.2, 16.8, 18.5, 19.1, 19.6, 19.9, 20.1, 20.7, 21.8, 23.5, 24.0, 24.5, 25.2, 26.0, 26.7, 30.4, 34.8

Example 2: Preparation of 6-(4-fluorophenoxy)-1-(tetrahydrofuran-2-ylmethyl)-1H-benzimidazole (Compound 2)

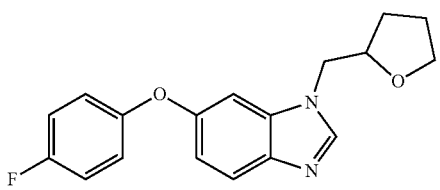

Compound 2 (0.26 g) was prepared according to the process of Example 1 by using the starting material, (tetrahydrofuran-2-yl)methanol (0.607 g) instead of 1-amino-2-methylpropan-2-ol.

$^1$H-NMR (DMSO-d6) δ: 1.49 (1H, m), 1.75 (2H, m), 1.94 (1H, m), 3.63 (2H, m), 4.07-4.34 (3H, m), 6.87-6.90 (1H, m), 6.97-7.02 (2H, m), 7.19 (2H, m), 7.35 (1H, m), 7.62 (1H, m), 8.14 (1H, s).

Example 3: Preparation of 6-(4-fluorophenoxy)-1-[2-(propan-2-yloxy)ethyl]-1H-benzimidazole (Compound 3)

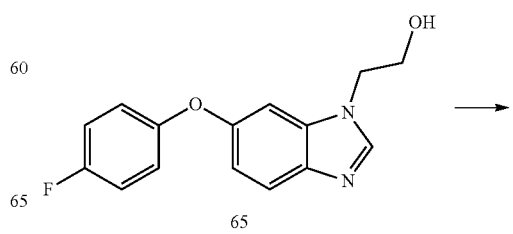

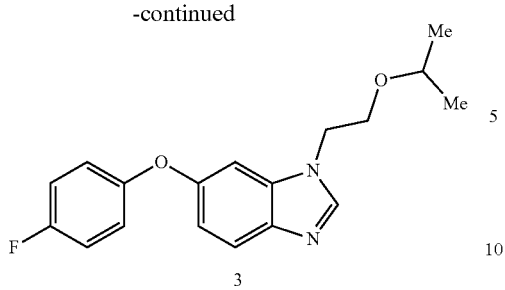

3

A mixture of Compound 65 (0.050 g) prepared according to Example 1 with an appropriate starting material, sodium hydride (0.011 g), and DMF (1.0 mL) was stirred at 0° C. for 30 minutes. To the reaction solution was added 2-bromopropane (0.045 g), and the mixture was stirred at room temperature further for 2 hours. To the reaction mixture were added saturated aqueous ammonium chloride, and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=99/1) to give Compound 3 (9 mg).

$^1$H-NMR (DMSO-d6) δ: 0.94 (6H, d, J=6.1 Hz), 3.44 (1H, m), 3.64 (2H, t, J=5.0 Hz), 4.30 (2H, t, J=5.0 Hz), 6.87-7.02 (3H, m), 7.18 (2H, m), 7.32 (1H, m), 7.62 (1H, m), 8.13 (1H, s).

Example 4: Preparation of 1-[2-(cyclopentyloxy)ethyl]-6-(4-fluorophenoxy)-1H-benzimidazole (Compound 4)

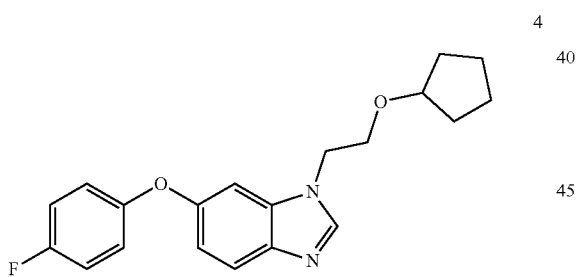

4

Compound 4 (0.007 g) was prepared according to the process of Example 3 by using bromocyclopentane (0.049 g) instead of 2-bromopropane.
LCMS: T=0.828, m/z=341

Example 5: Preparation of 1-[6-(4-fluorophenyl)-1H-benzimidazol-1-yl]-2-methylpropan-2-ol (Compound 5)

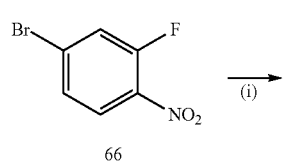

66

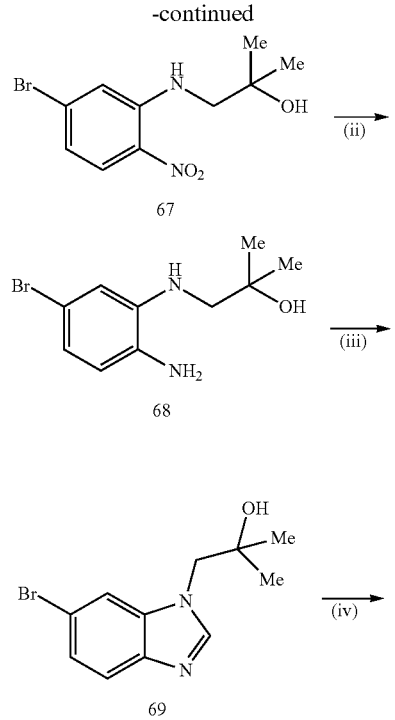

67

68

69

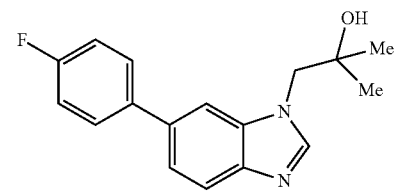

5

Step (i): Preparation of 1-[(5-bromo-2-nitrophenyl)amino]-2-methylpropan-2-ol (Compound 67)

Compound 67 (1.20 g) was prepared according to the process of Step (i) in Example 1 by using Compound 66 (1.1 g) instead of Compound 61.

Step (ii): Preparation of 1-[(2-amino-5-bromophenyl)amino]-2-methylpropan-2-ol (Compound 68)

Compound 68 (0.811 g) was prepared according to the process of Step (iii) in Example 1 by using Compound 67 (1.20 g) instead of Compound 63, and 3% Pt—S/C (0.24 g) instead of 10% Pd/C as a catalyst.

Step (iii): Preparation of 1-(6-bromo-1H-benzimidazol-1-yl)-2-methylpropan-2-ol (Compound 69)

Compound 69 (0.210 g) was prepared according to the process of Step (iv) in Example 1 by using Compound 68 (0.259 g) instead of Compound 64, and acetic acid (0.060 g) instead of p-toluenesulfonic acid monohydrate.

Step (iv): Preparation of 1-[6-(4-fluorophenyl)-1H-benzimidazol-1-yl]-2-methylpropan-2-ol (Compound 5)

A mixture of Compound 69 (0.050 g), 4-fluorophenylboronic acid (0.052 g), tetrakis(triphenylphosphine)palladium (0.043 g), and 1,4-dioxane (1.0 mL) was stirred at 80° C. for 1 hour. To the reaction mixture were added water and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=99/1) to give Compound 5 (30 mg).

$^1$H-NMR (DMSO-d6) δ: 1.11 (6H, s), 4.20 (2H, s), 4.79 (1H, s), 7.29 (2H, m), 7.45 (1H, m), 7.66-7.76 (3H, m), 7.94 (1H, s), 8.13 (1H, s).

Examples 6-10

Examples 6 to 10 shown in the following table were prepared according to the process of Example 5 by using each appropriate starting material.

TABLE 1

| Example | Chemical Structure | Spectrum data |
| --- | --- | --- |
| 6 | 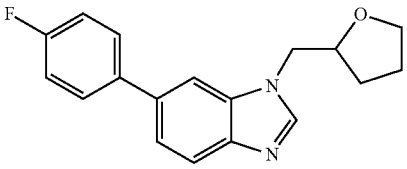 [SMILES: Fc1ccc(-c2ccc3ncn(CC4CCCO4)c3c2)cc1] | LCMS: T = 0.666, m/z = 297 |
| 7 | 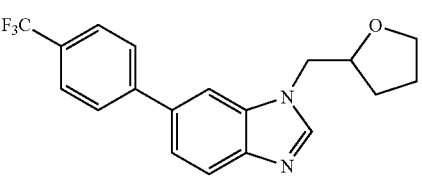 [SMILES: FC(F)(F)c1ccc(-c2ccc3ncn(CC4CCCO4)c3c2)cc1] | LCMS: T = 0.831, m/z = 347 |
| 8 | 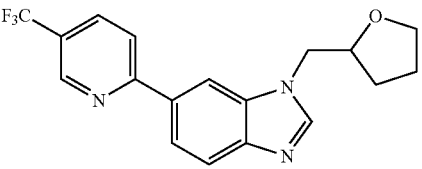 [SMILES: FC(F)(F)c1ccc(-c2ccc3ncn(CC4CCCO4)c3c2)nc1] | $^1$H-NMR (DMSO-d6) δ: 1.53-1.82 (3H, m), 1.95-2.00 (1H, m), 3.58-3.79 (2H, m), 4.18-4.51 (3H, m), 7.76 (1H, m), 8.06 (1H, m), 8.29 (3H, m), 8.48 (1H, s), 9.03 (1H, s). |
| 9 | 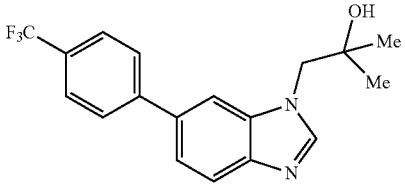 | $^1$H-NMR (DMSO-d6) δ: 1.12 (6H, s), 4.23 (2H, s), 4.81 (1H, s), 7.55 (1H, m), 7.73 (1H, m), 7.82 (2H, m), 7.94 (2H, m), 8.07 (1H, s), 8.18 (1H, s). |
| 10 | 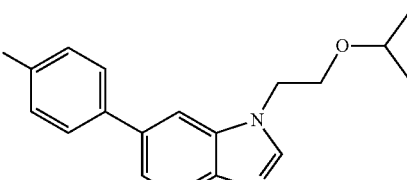 | LCMS: T = 1.055, m/z = 375 |

Example 11: Preparation of 2-methyl-1-{6-[5-(trifluoromethyl)pyridin-2-yl]-1H-benzimidazol-1-yl}propan-2-ol (Compound 11)

Example 12: Preparation of 1-[2-(cyclopentyloxy)ethyl]-6-[5-(trifluoromethyl)pyridin-2-yl]-1H-benzimidazole (Compound 12)

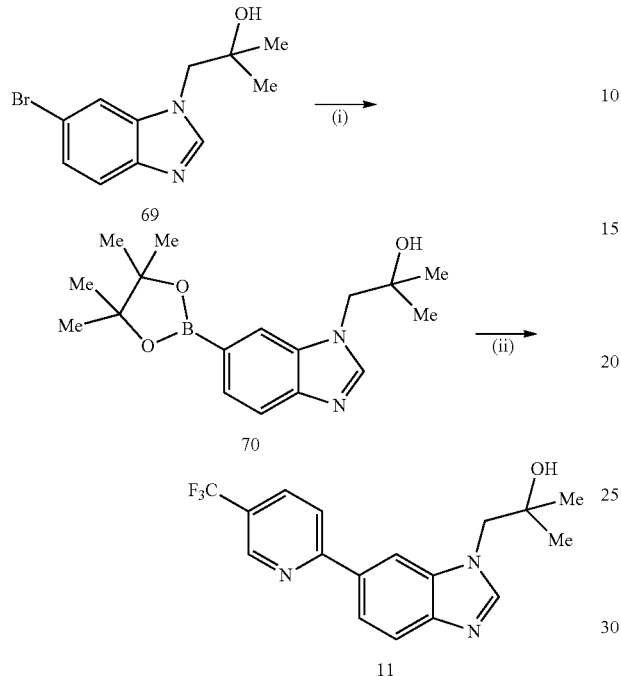

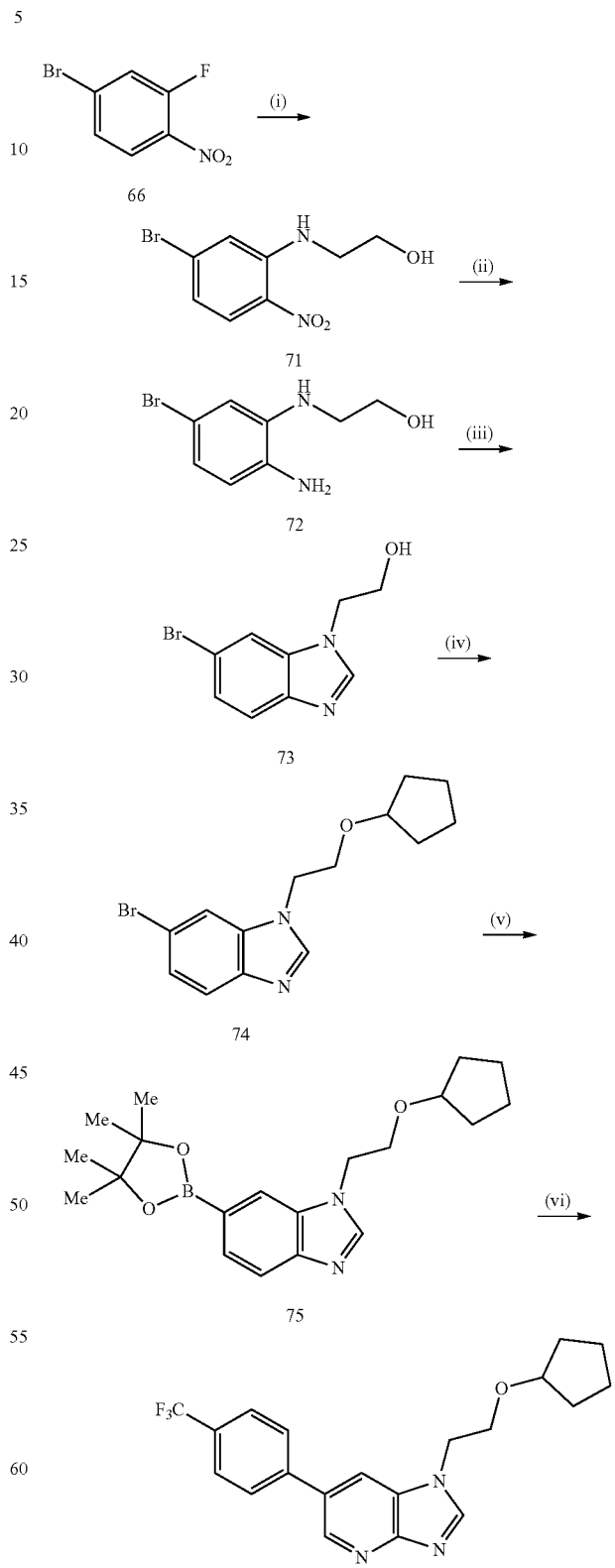

Step (i): Preparation of 2-methyl-1-[6-(4,4,5,5-tetramethyl-1,3,2-dioxaboran-2-yl)-1H-benzimidazol-1-yl]propan-2-ol (Compound 70)

A mixture of Compound 69 (0.10 g), bis(pinacolato)diboron (0.142 g), dichloro[1,1'-bis(diphenylphosphino)ferrocene]palladium (0.054 g), potassium acetate (0.146 g), and 1,4-dioxane (2.0 mL) was stirred at 90° C. for 2 hours. To the reaction mixture were added water and ethyl acetate, and the objective product was extracted in the organic layer. The organic layer was dried over anhydrous sodium sulfate and concentrated under reduced pressure, and then the residue was purified by silica gel column chromatography (eluate: hexane/ethyl acetate=8/1) to give Compound 70 (90 mg).

Step (ii): Preparation of 2-methyl-1-{6-[5-(trifluoromethyl)pyridin-2-yl]-1H-benzimidazol-1-yl}propan-2-ol (Compound 11)

A mixture of Compound 70 (90 mg), 2-bromo-5-trifluoromethylpyridine (0.126 g), 3 mol/L aqueous sodium carbonate (0.372 mL), tetrakis(triphenylphosphine)palladium (86 mg), and 1,4-dioxane (2 mL) was stirred at 80° C. for 1 hour. To the reaction mixture were added water and ethyl acetate, and the objective product was extracted in the organic layer. The organic layer was dried over anhydrous sodium sulfate and concentrated under reduced pressure, and then the residue was purified by silica gel column chromatography (eluate: a mixed solvent of chloroform and methanol) to give Compound 11 (40 mg).

$^1$H-NMR (DMSO-d6) δ: 1.13 (6H, s), 4.25 (2H, s), 4.83 (1H, s), 7.74 (1H, m), 8.04 (1H, m), 8.24 (3H, m), 8.49 (1H, s), 9.02 (1H, s).

Step (i): Preparation of 2-[(5-bromo-2-nitrophenyl)amino]ethan-1-ol (Compound 71)

Compound 71 (0.698 g) was prepared according to the process of Step (i) in Example 5 by using 2-aminoethanol (0.458 g) instead of 1-amino-2-methylpropan-2-ol.

Step (ii): Preparation of 2-[(2-amino-5-bromophenyl)amino]ethan-1-ol (Compound 72)

Compound 72 (0.561 g) was prepared according to the process of Step (ii) in Example 5 by using Compound 71 (0.698 g) instead of Compound 67.

Step (iii): Preparation of 2-(6-bromo-1H-benzimidazol-1-yl)ethan-1-ol (Compound 73)

Compound 73 (0.19 g) was prepared according to the process of Step (iii) in Example 5 by using Compound 72 (0.231 g) instead of Compound 68.

Step (iv): Preparation of 6-bromo-1-[2-(cyclopentyloxy)ethyl]-1H-benzimidazole (Compound 74)

Compound 74 (0.025 g) was prepared according to the process of Example 3 by using Compound 73 (0.19 g) instead of Compound 65.

Step (v): Preparation of 1-[2-(cyclopentyloxy)ethyl]-6-(4,4,5,5-tetramethyl-1,3,2-dioxaboran-2-yl)-1H-benzimidazole (Compound 75)

Compound 75 was prepared according to the process of Step (i) in Example 11 by using Compound 74 (0.015 g) instead of Compound 69. The crude product was used in the next step without purification.

Step (vi): Preparation of 1-[2-(cyclopentyloxy)ethyl]-6-[5-(trifluoromethyl)pyridin-2-yl]-1H-benzimidazole (Compound 12)

Compound 12 (0.018 g) was prepared according to the process of Step (ii) in Example 11 by using Compound 75 instead of Compound 70.
LCMS: T=0.974, m/z=376

Example 13: Preparation of 2-methyl-1-(6-phenoxy-1H-benzimidazol-1-yl)propan-2-ol (Compound 13)

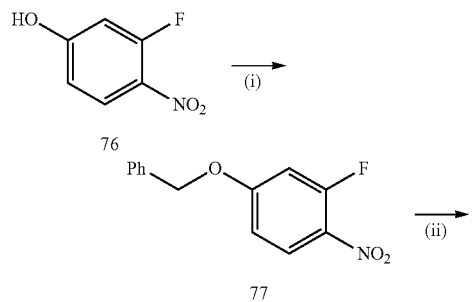

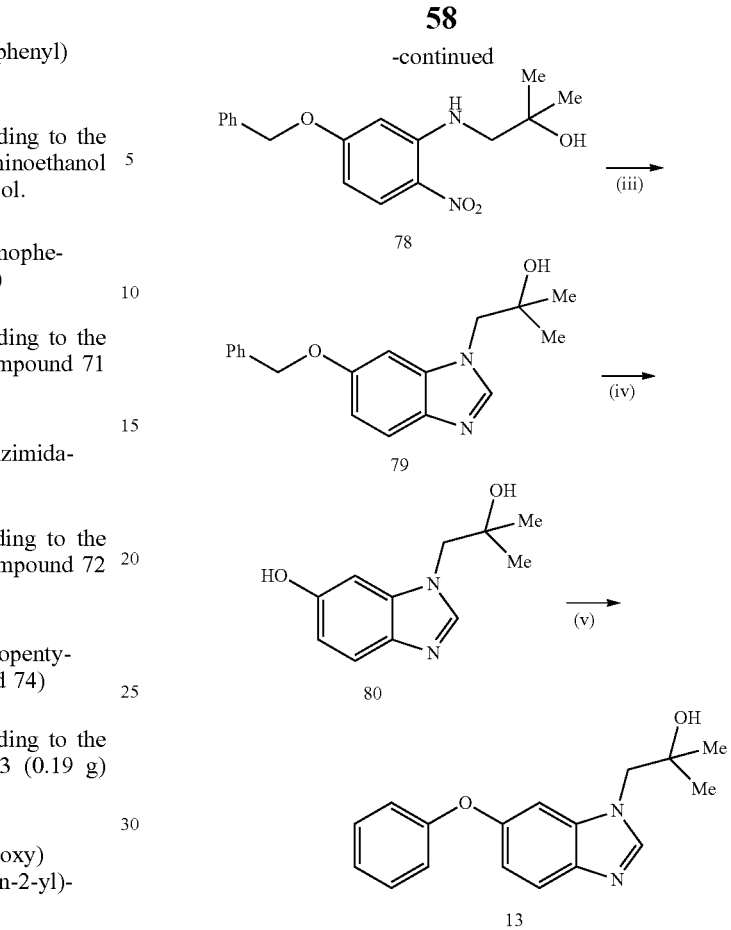

Step (i): Preparation of 4-(benzyloxy)-2-fluoro-1-nirobenzene (Compound 77)

Under a nitrogen atmosphere, potassium carbonate (27.1 g) was added to a solution of Compound 76 (20.5 g) in DMF (326 mL) at room temperature, and then the mixture was stirred. The reaction mixture was heated to 97° C., and benzyl bromide (27.9 g) was added dropwise thereto over 20 minutes. The reaction mixture was stirred further for 1 hour. To the reaction mixture were added ethyl acetate and water, and the objective product was extracted in the organic layer. The organic layer was washed twice with water, and then concentrated under reduced pressure. To the obtained residue was added toluene (162 mL), and the mixture was concentrated under reduced pressure. (The above extraction procedure was repeated twice.) The obtained residue was slurry-washed with a mixture of ethyl acetate/hexane (=1/4) to give Compound 77 (28.0 g).

Step (ii): Preparation of 1-{[5-(benzyloxy)-2-nitrophenyl]amino}-2-methylpropan-2-ol (Compound 78)

Under a nitrogen atmosphere, diisopropylethylamine (32 g) was added to a solution of Compound 77 (24.5 g) in NMP (248 mL) at room temperature. The reaction mixture was heated to 88° C., and 1-amino-2-methylpropan-2-ol (11.48 g) was added dropwise thereto over 12 minutes. The reaction mixture was stirred further for 1 hour. To the reaction mixture were added ethyl acetate and water, and the objective product was extracted in the organic layer. The aqueous layer was extracted with ethyl acetate, and the combined organic layer was washed with water. The organic layer was concentrated under reduced pressure. To the obtained residue was added toluene (248 mL), and the mixture was concentrated under reduced pressure. (The above extraction procedure was repeated twice.) To the obtained residue was added water (248 mL) dropwise. The precipitated crystal was collected on a filter, and dried to give Compound 78 (32.8 g).

Step (iii): Preparation of 1-[6-(benzyloxy)-1H-benzimidazol-1-yl]-2-methylpropan-2-ol (Compound 79)

To a solution of Compound 78 (0.5 g) in methanol (7.9 mL) were added trimethyl orthoformate (4.37 mL), formic acid (0.6 mL), and zinc (0.52 g), and the mixture was stirred heating at 70° C. for 1 hour. The reaction mixture was filtered through Celite, and the filtrate was concentrated under reduced pressure. To the residue were added a water solution of Rochelle salt (30 mL) and ethyl acetate (30 mL), and the objective product was extracted in the organic layer. The organic layer was washed with brine, dried over anhydrous sodium sulfate, and then concentrated under reduced pressure to give Compound 79 (0.45 g).

Step (iv): Preparation of 1-(2-hydroxy-2-methylpropyl)-1H-benzimidazol-6-ol (Compound 80)

To a solution of Compound 79 (0.5 g) in methanol (5.6 mL) at room temperature was added 10% palladium-carbon (50% water-content, 0.1 g), and the mixture was stirred under a hydrogen atmosphere for 4 hours. The reaction mixture was filtered through Celite, and the filtrate was concentrated under reduced pressure. To the obtained residue was added ethyl acetate/hexane, and the mixture was slurry-washed at room temperature. The obtained crystal was collected on a filter, and dried to give Compound 80 (0.32 g).

Step (v): Preparation of 2-methyl-1-(6-phenoxy-1H-benzimidazol-1-yl)propan-2-ol (Compound 13)

A reaction mixture of Compound 80 (0.10 g), phenylboronic acid (0.118 g), copper acetate (0.132 g), triethylamine (0.198 mL), and chloroform (2.5 mL) was stirred at 35° C. for 2 hours. To the reaction mixture were added saturated aqueous ammonium chloride, and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=98/2) to give Compound 13 (0.013 g).

$^1$H-NMR (DMSO-d6) δ: 1.06 (6H, s), 4.08 (2H, s), 4.73 (1H, s), 6.87-6.94 (3H, m), 7.05 (1H, m), 7.33 (2H, m), 7.42 (1H, m), 7.62 (1H, m), 8.09 (1H, s).

Examples 14-27

Examples 14 to 27 shown in the following table were prepared according to the process of Example 13 by using each appropriate starting material.

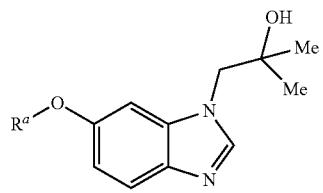

TABLE 2

| Example | R$^a$— | Spectrum data |
|---|---|---|
| 14 | 4-Me-C$_6$H$_4$- | $^1$H-NMR (DMSO-d6) δ: 1.06 (6H, s), 2.25 (3H, s), 4.07 (2H, s), 4.72 (1H, s), 6.84 (3H, m), 7.13 (2H, m), 7.36 (1H, m), 7.60 (1H, m), 8.07 (1H, s). |
| 15 | 4-F$_3$C-C$_6$H$_4$- | $^1$H-NMR (DMSO-d6) δ: 1.14 (6H, s), 4.11 (2H, s), 4.73 (1H, s), 6.95-7.08 (3H, m), 7.53 (1H, m), 7.68 (3H, m), 8.13 (1H, s). |
| 16 | 3-F-C$_6$H$_4$- | $^1$H-NMR (CDCl$_3$) δ: 1.27 (6H, s), 4.12 (2H, s), 6.66 (1H, dt, J = 10.4, 2.4 Hz), 6.72-6.79 (2H, m), 7.03 (1H, dd, J = 8.9, 2.1 Hz), 7.13 (1H, d, J = 1.8 Hz), 7.21-7.27 (1H, m), 7.76 (1H, d, J = 8.5 Hz), 8.34 (1H, s). |
| 17 | 3,5-F$_2$-C$_6$H$_3$- | $^1$H-NMR (CDCl$_3$) δ: 1.28 (6H, s), 4.16 (2H, s), 6.42-6.54 (3H, m), 7.06 (1H, dd, J = 8.5, 2.4 Hz), 7.17 (1H, d, J = 1.8 Hz), 7.82 (1H, d, J = 9.2 Hz), 8.48 (1H, s). |
| 18 | 3,4-F$_2$-C$_6$H$_3$- | $^1$H-NMR (CDCl$_3$) δ: 1.27 (6H, s), 4.13 (2H, s), 6.66-6.71 (1H, m), 6.77-6.82 (1H, m), 7.00 (1H, dd, J = 8.9, 2.1 Hz), 7.06-7.13 (2H, m), 7.77 (1H, d, J = 8.5 Hz), 8.39 (1H, s). |
| 19 | 4-MeS(O)$_2$-C$_6$H$_4$- | $^1$H-NMR (CDCl$_3$) δ: 1.27 (6H, s), 3.03 (3H, s), 4.12 (2H, s), 7.01-7.06 (3H, m), 7.17-7.26 (1H, m), 7.79 (1H, d, J = 8.5 Hz), 7.85 (2H, d, J = 8.5 Hz), 8.28 (1H, s). |
| 20 | 4-Cl-C$_6$H$_4$- | $^1$H-NMR (DMSO-d6) δ: 1.07 (6H, s), 4.09 (2H, s), 4.73 (1H, s), 6.89-6.96 (3H, m), 7.37 (2H, m), 7.44 (1H, m), 7.64 (1H, m), 8.11 (1H, s). |
| 21 | 4-MeO-C$_6$H$_4$- | $^1$H-NMR (CDCl$_3$) δ: 1.20 (6H, s), 3.73 (3H, s), 3.96 (2H, s), 6.78-6.82 (2H, m), 6.85-6.90 (3H, m), 6.92 (1H, d, J = 1.8 Hz), 7.56 (1H, d, J = 9.2 Hz) 7.93 (1H, s). |
| 22 | 4-F$_3$CO-C$_6$H$_4$- | $^1$H-NMR (CDCl$_3$) δ: 1.26 (6H, s) 4.08 (2H, s), 6.93-7.00 (3H, m), 7.09-7.16 (3H, m), 7.73 (1H, d, J = 8.5 Hz), 8.17 (1H, s). |

TABLE 2-continued

| Example | Rᵃ— | Spectrum data |
|---|---|---|
| 23 | (4-NC-C₆H₄-) | ¹H-NMR (CDCl₃) δ: 1.28 (6H, s), 4.13 (2H, s), 6.96-6.99 (2H, m), 7.03 (1H, dd, J = 8.9, 2.1 Hz), 7.18 (1H, d, J = 1.8 Hz), 7.55-7.59 (2H, m), 7.81 (1H, d, J = 8.5 Hz), 8.33 (1H, s). |
| 24 | (5-Me-pyridin-2-yl with 2-Me) | ¹H-NMR (DMSO-d6) δ: 1.06 (6H, s), 2.42 (3H, s), 4.08 (2H, s), 4.72 (1H, s), 6.90 (1H, m), 7.23 (2H, m), 7.42 (1H, m), 7.63 (1H, m), 8.09 (1H, s), 8.20 (1H, m). |
| 25 | (2-CF₃-pyridin-5-yl) | ¹H-NMR (DMSO-d6) δ: 1.07 (6H, s), 4.11 (2H, s), 4.73 (1H, s), 7.04 (1H, m), 7.44 (1H, m), 7.60 (1H, m), 7.71 (1H, m), 7.85 (1H, m), 8.15 (1H, s), 8.52 (1H, m). |
| 26 | (5-Me-pyridin-2-yl) | ¹H-NMR (DMSO-d6) δ: 1.07 (6H, s), 2.22 (3H, s), 4.09 (2H, s), 4.72 (1H, s), 6.85-6.91 (2H, m), 7.44 (1H, m), 7.59-7.65 (2H, m), 7.94 (1H, m), 8.09 (1H, s). |
| 27 | (6-Cl-pyridin-3-yl) | ¹H-NMR (CDCl₃) δ: 1.25 (6H, s), 1.74 (1H, s), 4.04 (2H, s), 6.96-6.97 (1H, m), 7.11-7.12 (1H, m), 7.22-7.22 (2H, m), 7.73-7.75 (1H, m), 7.96-7.97 (1H, m), 8.11-8.11 (1H, m). |

Example 28: Preparation of 2-methyl-1-(6-{[5-(trifluoromethyl)pyridin-2-yl]oxy}-1H-benzimidazol-1-yl)propan-2-ol (Compound 28)

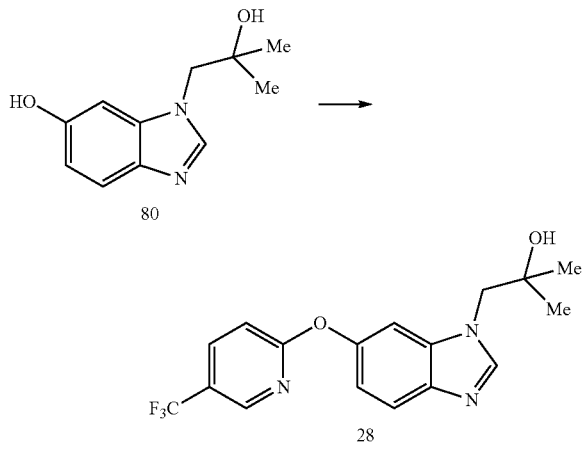 [SMILES: CC(C)(O)Cn1cnc2ccc(O)cc21 ; CC(C)(O)Cn1cnc2ccc(Oc3ccc(C(F)(F)F)cn3)cc21]

A reaction mixture of Compound 80 (1.34 g), 2-fluoro-5-(trifluoromethyl)pyridine (1.40 g), cesium carbonate (3.18 g), and acetonitrile (22 mL) was stirred at 60° C. for 4 hours. To the reaction mixture were added water and ethyl acetate, and the objective product was extracted in the organic layer. The organic layer was dried over anhydrous sodium sulfate and concentrated under reduced pressure, and then the residue was purified by silica gel column chromatography (eluate: chloroform/methanol=95/5) to give Compound 28 (1.78 g).

¹H-NMR (DMSO-d6) δ: 1.07 (6H, s), 4.11 (2H, s), 4.73 (1H, s), 7.00 (1H, m), 7.18 (1H, m), 7.56 (1H, m), 7.66 (1H, m), 8.13 (1H, s), 8.20 (1H, m), 8.54 (1H, m).

XRD; 2θ=9.1, 12.9, 13.7, 17.5, 18.0, 18.1, 20.5, 20.8, 21.2, 21.8, 22.3, 23.2, 23.8, 24.6, 24.9, 26.9, 27.3, 28.2, 30.2, 32.5.

Examples 29-42

Examples 29 to 42 shown in the following table were prepared according to the process of Example 28 by using each appropriate starting material.

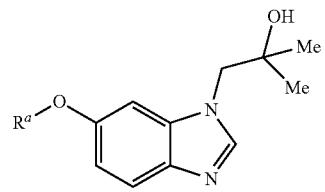

TABLE 3

| Example | Rᵃ— | Spectrum data |
|---|---|---|
| 29 | (5-F-pyridin-2-yl) | ¹H-NMR (CDCl₃) δ: 1.22 (6H, s), 4.00 (2H, s), 6.82 (1H, dd, J = 9.2, 3.7 Hz), 6.94 (1H, dd, J = 8.9, 2.1 Hz), 7.17 (1H, d, J = 2.4 Hz), 7.33-7.38 (1H, m), 7.65 (1H, d, J = 9.2 Hz), 7.89 (1H, s), 7.92 (1H, d, J = 3.1 Hz). |
| 30 | (3-CF₃-pyridin-2-yl) | ¹H-NMR (CDCl₃) δ: 1.28 (6H, s), 1.65 (1H, s), 4.08 (2H, s), 7.04-7.08 (2H, m), 7.29 (1H, d, J = 1.8 Hz), 7.79 (1H, d, J = 8.5 Hz), 7.97-7.99 (2H, m), 8.24 (1H, dd, J = 4.9, 1.8 Hz). |
| 31 | (4-CF₃-pyridin-2-yl) | ¹H-NMR (CDCl₃) δ: 1.28 (6H, s), 1.75 (1H, s), 4.07 (2H, s), 7.04 (1H, dd, J = 8.9, 2.1 Hz), 7.13 (1H, s), 7.17 (1H, d, J = 5.5 Hz), 7.26 (1H, d, J = 2.1 Hz), 7.79 (1H, d, J = 8.9 Hz), 7.97 (1H, s), 8.29 (1H, d, J = 5.5 Hz). |
| 32 | (6-CF₃-pyridin-2-yl) | ¹H-NMR (CDCl₃) δ: 1.28 (6H, s), 1.69 (1H, s), 4.07 (2H, s), 7.03-7.05 (2H, m), 7.35-7.36 (2H, m), 7.75-7.82 (2H, m), 7.98 (1H, s). |
| 33 | (5-CHF₂-pyridin-2-yl) | ¹H-NMR (CDCl₃) δ: 1.28 (6H, s), 1.95 (1H, s), 4.07 (2H, s), 6.63 (1H, t, J = 55.8 Hz), 6.97-7.04 (2H, m), 7.26 (1H, d, J = 1.8 Hz), 7.77 (1H, d, J = 8.5 Hz), 7.82 (1H, d, J = 9.2 Hz), 7.95 (1H, s), 8.24 (1H, s). |
| 34 | (5-Cl-pyridin-2-yl) | ¹H-NMR (CDCl₃) δ: 1.28 (6H, s), 1.81 (1H, s), 4.06 (2H, s), 6.86 (1H, d, J = 8.5 Hz), 7.02 (1H, dd, J = 9.2, 1.8 Hz), 7.23 (1H, d, J = 1.8 Hz), 7.60-7.63 (1H, m), 7.76 (1H, d, J = 8.5 Hz), 7.95 (1H, s), 8.08 (1H, d, J = 2.4 Hz). |
| 35 | (6-CF₃-pyridazin-3-yl) | ¹H-NMR (CDCl₃) δ: 1.28 (6H, s), 1.63 (1H, s), 4.08 (2H, s), 7.10 (1H, dd, J = 8.5, 2.1 Hz), 7.30 (1H, d, J = 9.8 Hz), 7.39 (1H, d, J = 2.1 Hz), 7.78 (1H, d, J = 9.8 Hz), 7.82 (1H, d, J = 8.5 Hz), 7.98 (1H, s). |

TABLE 4

| Example | R<sup>a</sup>— | Spectrum data |
|---|---|---|
| 36 | [pyrimidine with F₃C and N] | ¹H-NMR (CDCl₃) δ: 1.29 (6H, s), 1.66 (1H, s), 4.08 (2H, s), 7.06 (1H, dd, J = 8.9, 2.1 Hz), 7.30 (1H, d, J = 2.1 Hz), 7.82 (1H, d, J = 8.9 Hz), 7.99 (1H, s), 8.40 (1H, s), 8.49 (1H, s). |
| 37 | [pyridazine with Cl] | ¹H-NMR (CDCl₃) δ: 1.26 (6H, s), 2.05 (1H, s), 4.03 (2H, s), 7.06 (1H, dd, J = 8.5, 2.4 Hz), 7.15 (1H, d, J = 9.2 Hz), 7.35 (1H, d, J = 2.4 Hz), 7.47 (1H, d, J = 9.2 Hz), 7.76 (1H, d, J = 8.5 Hz), 7.93 (1H, s). |
| 38 | [pyridine with F and Cl] | ¹H-NMR (CDCl₃) δ: 1.28 (6H, s), 1.82 (1H, s), 4.07 (2H, s), 7.03-7.06 (1H, m), 7.27-7.27 (1H, m), 7.49-7.51 (1H, m), 7.75-7.77 (1H, m), 7.83-7.83 (1H, m), 7.95 (1H, s). |
| 39 | [pyridine with F and F₃C] | ¹H-NMR (CDCl₃) δ: 1.29 (6H, s), 1.68 (1H, s), 4.08 (2H, s), 7.07 (1H, dd, J = 8.9, 2.1 Hz), 7.31 (1H, d, J = 2.4 Hz), 7.68 (1H, dd, J = 9.5, 2.1 Hz), 7.80 (1H, d, J = 8.9 Hz), 7.98 (1H, s), 8.13 (1H, d, J = 2.4 Hz). |
| 40 | [pyridine with NC] | ¹H-NMR (CDCl₃) δ: 1.28 (6H, s), 1.81 (1H, s), 4.07 (2H, s), 7.00-7.03 (2H, m), 7.26 (1H, d, J = 2.3 Hz), 7.79 (1H, d, J = 8.7 Hz), 7.90 (1H, dd, J = 8.7, 2.3 Hz), 7.97 (1H, s), 8.42-8.43 (1H, m). |
| 41 | [pyrimidine with F₃C] | ¹H-NMR (CDCl₃) δ: 1.29 (6H, s), 1.71 (1H, s), 4.08 (2H, s), 7.08 (1H, dd, J = 8.5, 2.4 Hz), 7.31 (1H, d, J = 2.4 Hz), 7.81 (1H, d, J = 8.5 Hz), 7.99 (1H, s), 8.77 (2H, s). |
| 42 | [pyridine with Cl] | ¹H-NMR (CDCl₃) δ: 1.28 (6H, s), 1.70 (1H, s), 4.08 (2H, s), 6.77-6.78 (2H, m), 6.98-7.00 (1H, m), 7.19 (1H, d, J = 1.8 Hz), 7.80 (1H, d, J = 8.5 Hz), 8.01 (1H, s), 8.19 (1H, d, J = 5.5 Hz). |

Example 43: Preparation of 2-methyl-1-(5-{[6-(trifluoromethyl)pyridin-2-yl]oxy}-1H-benzimidazol-1-yl)propan-2-ol (Compound 43)

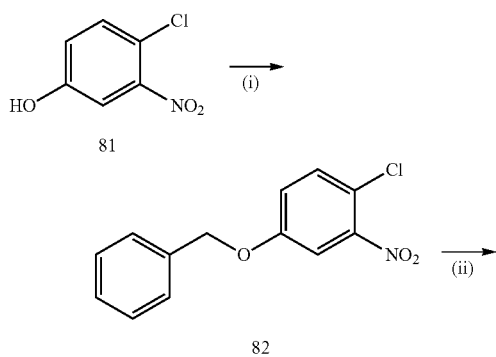

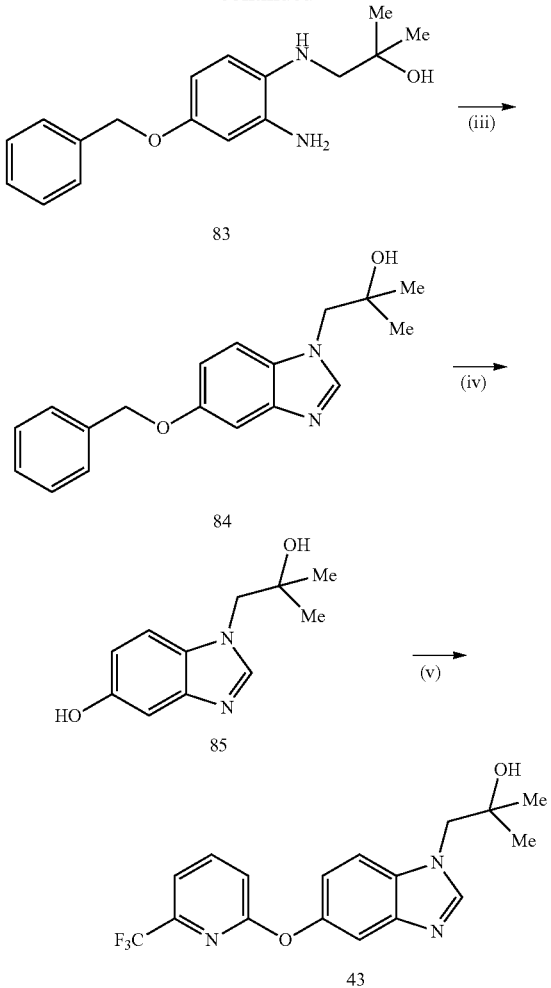

Step (i): Preparation of 4-(benzyloxy)-1-chloro-2-nirobenzene (Compound 82)

Under a nitrogen atmosphere, potassium carbonate (5.97 g) and benzyl bromide (5.91 g) were added to a solution of Compound 81 (5 g) in DMF (56 mL) at room temperature, and then the mixture was stirred for 3 hours. To the reaction mixture were added ethyl acetate and water, and the objective product was extracted in the organic layer. The organic layer was washed with brine, and dried over anhydrous sodium sulfate. After the organic layer was concentrated under reduced pressure, the residue was purified by silica gel column chromatography (eluate: hexane/ethyl acetate=90/10) to give Compound 82 (7.52 g).

Step (ii): Preparation of 1-{[4-(benzyloxy)-2-nitrophenyl]amino}-2-methylpropan-2-ol (Compound 83)

Under a nitrogen atmosphere, diisopropylethylamine (5.53 g) and 1-amino-2-methylpropan-2-ol (3.05 g) were added to a solution of Compound 82 (7.52 g) in NMP (30 mL) at room temperature, and the mixture was stirred at 100° C. for 1 hour, and then at 150° C. for 1 hour. The reaction mixture stood to cool at room temperature, and diisopropylethylamine (5.53 g) and potassium fluoride (1.99 g) were added thereto at room temperature. The mixture was stirred at 150° C. for 1 hour, and then at 200° C. for 40 hours. To the reaction mixture were added ethyl acetate and water, and the objective product was extracted in the organic layer. The organic layer was washed with brine, and dried over anhydrous sodium sulfate. After the organic layer was concentrated under reduced pressure, the residue was purified by silica gel column chromatography (eluate: hexane/ethyl acetate=60/40) to give Compound 83 (5.3 g).

Step (iii): Preparation of 1-[5-(benzyloxy)-1H-benzimidazol-1-yl]-2-methylpropan-2-ol (Compound 84)

To a solution of Compound 83 (5.3 g) in methanol (85 mL) were added trimethyl orthoformate (44.4 g), formic acid (7.71 g) and zinc (5.48 g), and the mixture was stirred at room temperature for 2 hours. The reaction mixture was filtered through Celite, and the filtrate was concentrated under reduced pressure. The residue was purified by silica gel column chromatography (eluate: chloroform/methanol=95/5) to give Compound 84 (2.68 g).

Step (iv): Preparation of 1-(2-hydroxy-2-methylpropyl)-1H-benzimidazol-5-ol (Compound 85)

To a solution of Compound 84 (2.68 g) in methanol (45 mL) was added 10% palladium-carbon (50% water-content, 0.53 g), and the mixture was stirred under a hydrogen atmosphere for 4 hours. The reaction mixture was filtered through Celite, and the filtrate was concentrated under reduced pressure. To the obtained residue was added ethyl acetate, and the mixture was slurry-washed at room temperature. The obtained crystal was collected on a filter, and dried to give Compound 85 (1.58 g).

Step (v): Preparation of 2-methyl-1-(5-{[6-(trifluoromethyl)pyridin-2-yl]oxy}-1H-benzimidazol-1-yl)propan-2-ol (Compound 43)

Under a nitrogen atmosphere, 2-fluoro-6-(trifluoromethyl)pyridine (0.048 g) and cesium carbonate (0.118 g) were added to a solution of Compound 85 (0.05 g) in NMP (1 mL) at room temperature, and the mixture was stirred at 100° C. for 3 hours. The reaction mixture was directly purified by silica gel column chromatography (eluate: chloroform/methanol=95/5) to give Compound 43 (0.064 g).

$^1$H-NMR (CDCl$_3$) δ: 1.31 (6H, s), 1.83 (1H, br s), 4.14 (2H, s), 6.98 (1H, d, J=8.7 Hz), 7.13 (1H, dd, J=8.7, 2.3 Hz), 7.35 (1H, d, J=7.3 Hz), 7.45 (1H, d, J=8.7 Hz), 7.56 (1H, d, J=1.8 Hz), 7.78 (1H, t, J=8.0 Hz), 8.07 (1H, s).

Examples 44-54

Examples 44 to 54 shown in the following table were prepared according to the process of Example 43 by using each appropriate starting material.

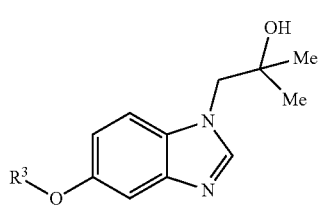

TABLE 5

| Example | R³— | Spectrum data |
|---|---|---|
| 44 | 5-(trifluoromethyl)pyridin-2-yl | $^1$H-NMR (CDCl$_3$) δ: 1.31 (6H, s), 1.81 (1H, br s), 4.14 (2H, s), 7.00 (1H, d, J = 8.7 Hz), 7.10 (1H, dd, J = 8.9, 2.1 Hz), 7.48 (1H, d, J = 8.7 Hz), 7.56 (1H, d, J = 2.3 Hz), 7.87 (1H, dd, J = 8.7, 2.7 Hz), 8.08 (1H, s), 8.40-8.42 (1H, m). |
| 45 | 4-(trifluoromethyl)pyridin-2-yl | $^1$H-NMR (CDCl$_3$) δ: 1.31 (6H, s), 1.86 (1H, br s), 4.13 (2H, s), 7.10 (1H, dd, J = 8.7, 2.3 Hz), 7.14 (1H, s), 7.16 (1H, d, J = 5.0 Hz), 7.47 (1H, d, J = 8.7 Hz), 7.55 (1H, d, J = 2.3 Hz), 8.02 (1H, s), 8.29 (1H, d, J = 5.0 Hz). |
| 46 | 3-(trifluoromethyl)pyridin-2-yl | $^1$H-NMR (CDCl$_3$) δ: 1.30 (6H, s), 1.81 (1H, br s), 4.12 (2H, s), 7.05 (1H, dd, J = 7.3, 5.0 Hz), 7.12 (1H, dd, J = 8.7, 2.3 Hz), 7.46 (1H, d, J = 8.7 Hz), 7.57 (1H, d, J = 2.3 Hz), 7.98 (1H, dd, J = 8.0, 1.6 Hz), 8.02 (1H, s), 8.25 (1H, dd, J = 5.0, 1.4 Hz). |
| 47 | pyridin-2-yl | $^1$H-NMR (CDCl$_3$) δ: 1.30 (6H, s), 1.86 (1H, br s), 4.11 (2H, s), 6.87-6.90 (1H, m), 6.95 (1H, ddd, J = 7.3, 5.0, 0.9 Hz), 7.10 (1H, dd, J = 8.7, 2.3 Hz), 7.44 (1H, d, J = 8.7 Hz), 7.53 (1H, d, J = 2.3 Hz), 7.65 (1H, ddd, J = 8.8, 6.7, 1.5 Hz), 8.00 (1H, s), 8.16 (1H, dt, J = 5.0, 1.1 Hz). |
| 48 | 5-fluoropyridin-2-yl | $^1$H-NMR (CDCl$_3$) δ: 1.30 (6H, s), 1.80 (1H, br s), 1.80 (0H, s), 4.12 (2H, s), 6.88 (1H, dd, J = 9.1, 3.7 Hz), 7.09 (1H, dd, J = 8.7, 2.3 Hz), 7.38-7.46 (2H, m), 7.51 (1H, d, J = 2.3 Hz), 7.99 (1H, d, J = 2.7 Hz), 8.03 (1H, s). |
| 49 | 5-chloropyridin-2-yl | $^1$H-NMR (CDCl$_3$) δ: 1.30 (6H, s), 1.72 (1H, br s), 4.15 (2H, s), 6.87 (1H, d, J = 9.1 Hz), 7.11 (1H, dd, J = 8.7, 2.3 Hz), 7.47 (1H, d, J = 8.7 Hz), 7.55 (1H, d, J = 1.8 Hz), 7.62 (1H, dd, J = 8.7, 2.7 Hz), 8.08-8.09 (1H, m), 8.17 (1H, br s). |
| 50 | 6-(trifluoromethyl)pyridazin-3-yl | $^1$H-NMR (CDCl$_3$) δ: 1.27 (6H, s), 1.88 (1H, br s), 4.12 (2H, s), 7.15 (1H, dd, J = 8.7, 2.3 Hz), 7.32 (1H, d, J = 9.1 Hz), 7.48 (1H, d, J = 8.7 Hz), 7.59 (1H, d, J = 2.3 Hz), 7.79 (1H, d, J = 9.1 Hz), 7.96 (1H, s). |
| 51 | 5-(trifluoromethyl)pyrazin-2-yl | $^1$H-NMR (CDCl$_3$) δ: 1.31 (6H, s), 1.76 (1H, br s), 4.15 (2H, s), 7.11 (1H, dd, J = 9.1, 2.3 Hz), 7.51 (1H, d, J = 8.7 Hz), 7.60 (1H, d, J = 2.3 Hz), 8.12 (1H, s), 8.40 (1H, d, J = 0.9 Hz), 8.50 (1H, d, J = 0.9 Hz). |
| 52 | 5-(trifluoromethyl)pyrimidin-2-yl | $^1$H-NMR (CDCl$_3$) δ: 1.31 (6H, s), 1.77 (1H, br s), 4.15 (2H, s), 7.14 (1H, dd, J = 8.7, 2.3 Hz), 7.51 (1H, d, J = 9.1 Hz), 7.61 (1H, d, J = 1.8 Hz), 8.11 (1H, s), 8.77 (2H, d, J = 0.9 Hz). |

TABLE 5-continued

| Example | R³— | Spectrum data |
|---|---|---|
| 53 | F₃C-pyridine-F (methyl) | ¹H-NMR (CDCl₃) δ: 1.31 (6H, s), 1.70 (1H, br s), 4.16 (2H, s), 7.14 (1H, dd, J = 8.9, 2.1 Hz), 7.50 (1H, d, J = 9.2 Hz), 7.62 (1H, d, J = 2.4 Hz), 7.67 (1H, dd, J = 9.5, 2.1 Hz), 8.14 (1H, s), 8.15 (1H, s). |
| 54 | Cl-pyridine-F (methyl) | ¹H-NMR (CDCl₃) δ: 1.31 (6H, s), 1.70 (1H, br s), 4.15 (2H, s), 7.13 (1H, dd, J = 8.7, 2.3 Hz), 7.46-7.52 (2H, m), 7.58 (1H, d, J = 2.3 Hz), 7.84 (1H, d, J = 2.3 Hz), 8.16 (1H, s). |

Examples 55-58

Examples 55 to 58 shown in the following table were prepared according to the process of Example 59 by using each appropriate starting material.

Example 59: Preparation of 2-methyl-4-(6-{[5-(trifluoromethyl)pyridin-2-yl]oxy}-1H-benzimidazol-1-yl)butan-2-ol (Compound 59)

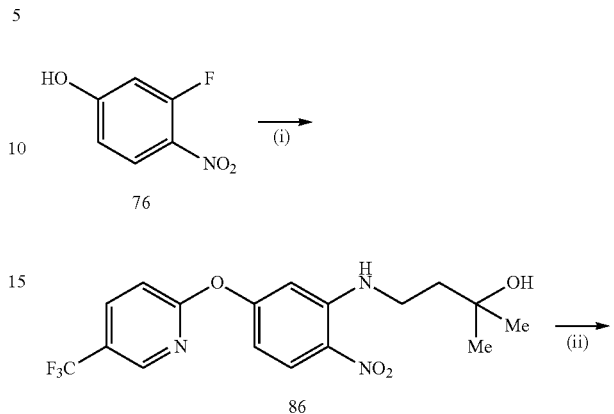

TABLE 6

| Example | Chemical Structure | Spectrum data |
|---|---|---|
| 55 | (structure: F₃C-pyridine-O-benzimidazole-CH₂-tetrahydropyran-OH) | ¹H-NMR (CDCl₃) δ: 1.48 (2H, d, J = 11.6 Hz), 1.75-1.83 (2H, m), 2.69 (1H, br s), 3.72 (2H, td, J = 11.6, 1.8 Hz), 3.80 (2H, td, J = 5.8, 3.7 Hz), 4.09 (2H, s), 6.98-7.02 (2H, m), 7.27 (1H, d, J = 1.8 Hz), 7.69 (1H, d, J = 8.5 Hz), 7.89 (1H, dd, J = 8.5, 2.4 Hz), 7.89 (1H, s), 8.38 (1H, s). |
| 56 | (structure: F₃C-pyridine-O-benzimidazole-CH₂-oxetane-OH) | ¹H-NMR (CDCl₃) δ: 4.39 (1H, br s), 4.51 (2H, s), 4.56 (2H, d, J = 7.9 Hz), 4.63 (2H, d, J = 7.9 Hz), 7.00 (2H, td, J = 8.2, 5.9 Hz), 7.36 (1H, d, J = 2.4 Hz), 7.66 (1H, d, J = 8.5 Hz), 7.89 (1H, dd, J = 8.5, 2.4 Hz), 7.94 (1H, s), 8.38 (1H, s). |
| 57 | (structure: F₃C-pyridine-O-benzimidazole-CH₂-cyclopropyl-OH with methyl) | ¹H-NMR (CDCl₃) δ: 0.83 (2H, dd, J = 6.6, 5.7 Hz), 1.04 (2H, t, J = 6.2 Hz), 1.59 (3H, br s), 4.20 (2H, s), 6.87 (1H, dd, J = 8.7, 2.3 Hz), 7.00 (1H, d, J = 8.7 Hz), 7.21 (1H, d, J = 1.8 Hz), 7.44 (1H, d, J = 9.1 Hz), 7.86-7.89 (2H, m), 8.39 (1H, t, J = 0.9 Hz). |
| 58 | (structure: F₃C-pyridine-O-benzimidazole-CH₂-cyclobutyl-OH) | ¹H-NMR (CDCl₃) δ: 1.63-1.73 (1H, m), 1.84-1.92 (1H, m), 2.06 (2H, q, J = 10.6 Hz), 2.17 (2H, q, J = 7.1 Hz), 4.22 (2H, s), 6.99-7.03 (2H, m), 7.31 (1H, s), 7.75 (1H, d, J = 8.5 Hz), 7.88 (1H, dd, J = 8.5, 1.8 Hz), 8.02 (1H, s), 8.40 (1H, s). |

-continued

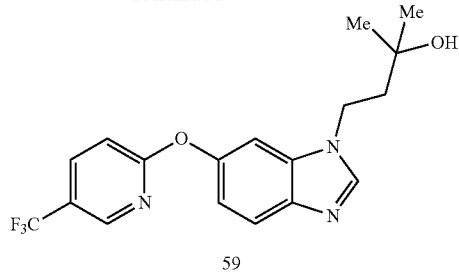

59

Step (i): Preparation of 2-methyl-4-[(2-nitro-5-{[5-(trifluoromethyl)pyridin-2-yl]oxy}phenyl)amino]butan-2-ol (Compound 86)

To a solution of Compound 76 (0.35 g) in NMP (7.5 mL) at room temperature was added diisopropylethylamine (1.01 g). To the mixture was added 4-amino-2-methylbutan-2-ol hydrochloride (0.37 g), and the reaction solution was heated to 110° C., and stirred for 3.5 hours. The reaction solution was cooled to room temperature. To reaction solution were added cesium carbonate (0.95 g) and 2-fluoro-5-(trifluoromethyl)pyridine (0.42 g), and the reaction solution was heated to 110° C., and stirred for 4 hours. The reaction solution was cooled to room temperature, ethyl acetate and water were added thereto, and the objective product was extracted in the organic layer. The aqueous layer was extracted with ethyl acetate, and the combined organic layer was washed with water. The organic layer was concentrated under reduced pressure, and the residue was purified by silica gel column chromatography (eluate: hexane/ethyl acetate=65/35) to give Compound 86 (0.6 g).

Step (ii): Preparation of 2-methyl-4-(6-{[5-(trifluoromethyl)pyridin-2-yl]oxy}-1H-benzimidazol-1-yl)butan-2-ol (Compound 59)

To a solution of Compound 86 (0.6 g) in methanol (7.8 mL) were added trimethyl orthoformate (4.26 mL), formic acid (0.6 mL) and zinc (0.51 g), and the mixture was stirred heating at 70° C. for 2 hours. The reaction mixture was filtered through Celite, and the filtrate was concentrated under reduced pressure. The obtained residue was purified by amino silica gel column chromatography (eluate: chloroform/methanol=93/7) to give Compound 59 (0.23 g).

$^1$H-NMR (CDCl3) δ: 1.31 (6H, s), 2.01-2.05 (2H, m), 4.30-4.34 (2H, m), 7.02 (1H, d, J=8.7 Hz), 7.06 (1H, dd, J=8.7, 2.3 Hz), 7.23 (1H, d, J=2.3 Hz), 7.82 (1H, d, J=8.7 Hz), 7.89 (1H, dd, J=8.7, 2.7 Hz), 8.04 (1H, s), 8.42-8.42 (1H, m).

Example 60: Preparation of 2-methyl-1-(6-{[5-(2,2,2-trifluoroethyl)pyridin-2-yl]oxy}-1H-benzimidazol-1-yl)propan-2-ol (Compound 60)

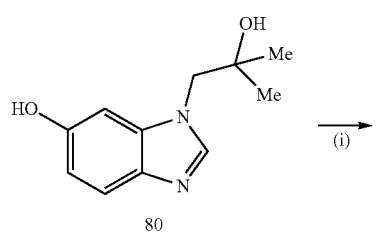

80

-continued

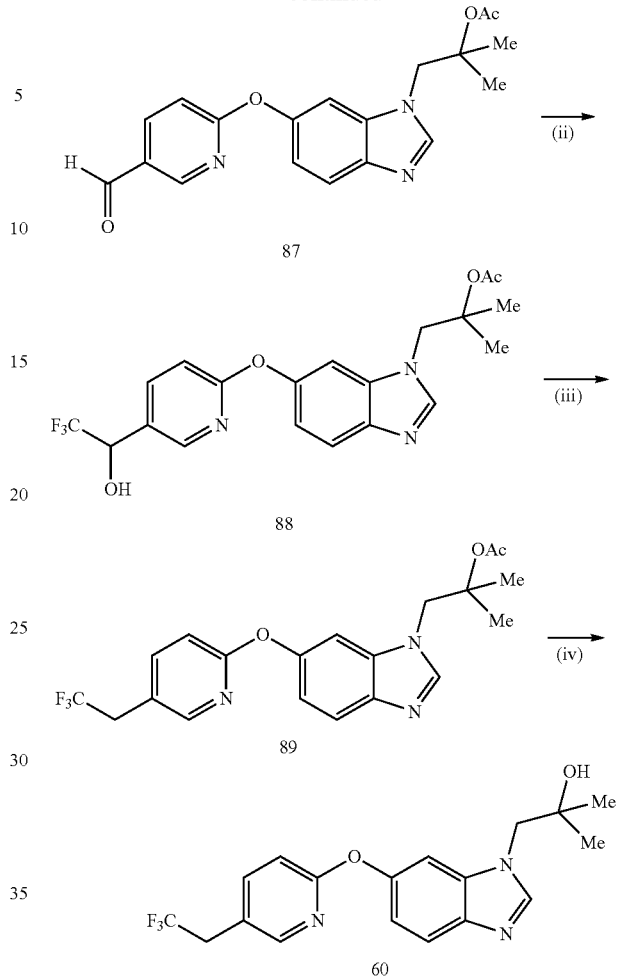

Step (i): Preparation of 1-{6-[(5-formylpyridin-2-yl)oxy]-1H-benzimidazol-1-yl}-2-methylpropan-2-yl Acetate (Compound 87)

To a solution of Compound 80 (0.103 g) in DMF (1 mL) were added 6-chloronicotinaldehyde (85 mg) and cesium carbonate (326 mg), and the mixture was heated at 110° C. for 1 hour. The reaction mixture was filtrated, and DMAP (92 mg) and acetic anhydride (0.142 mL) was added to the filtrate. The mixture was stirred at room temperature for 3 days. To the reaction mixture were added water and ethyl acetate:hexane=2:1 (v/v), and the objective product was extracted in the organic layer (the above extraction procedure was repeated three times). The organic layer was concentrated under reduced pressure, and then the residue was purified by silica gel column chromatography (eluate: chloroform/methanol=95/5) to give Compound 87 (130 mg).

Step (ii): Preparation of 2-methyl-1-(6-{[5-(2,2,2-trifluoro-1-hydroxyethyl)pyridin-2-yl]oxy}-1H-benzimidazol-1-yl)propan-2-yl Acetate (Compound 88)

To a solution of Compound 87 (0.13 g) and trimethyl (trifluoromethyl)silane (0.163 mL) in DMF (3.7 mL) were added potassium carbonate (0.025 g) and cesium fluoride (0.056 g), and the mixture was stirred at room temperature for 2 hours. To the reaction mixture was added another trimethyl (trifluoromethyl)silane (0.075 mL), and the reaction mixture was stirred at room temperature further for 1 hour. To the reaction mixture were added water and ethyl acetate:hexane=2:1 (v/v), and the objective product was extracted in the organic layer (the above extraction procedure was repeated three times). The organic layer was concentrated under reduced pressure, and then the residue was purified by silica gel column chromatography (eluate: chloroform/methanol=95/5) to give Compound 88 (0.106 g).

Step (iii): Preparation of 2-methyl-1-(6-{[5-(2,2,2-trifluoroethyl)pyridin-2-yl]oxy}-1H-benzimidazol-1-yl)propan-2-yl Acetate (Compound 89)

A solution of Compound 88 (0.1 g) and thiocarbonyldiimidazole (0.051 g) in dry THF (2 mL) was heated under reflux for 2 hours. After allowing the reaction mixture to stand to cool at room temperature, the reaction mixture was concentrated under reduced pressure. To the residue were added ethyl acetate and water, and the objective product was extracted in the organic layer. The organic layer was washed with brine, dried over anhydrous sodium sulfate, and then concentrated under reduced pressure. The obtained residue was dissolved in dry toluene (2 mL) under a nitrogen atmosphere, and then azobisisobutyronitrile (0.008 g) and tri-n-butyltin hydride (0.137 g) were added thereto. The mixture was stirred at 90° C. for 1 hour. The reaction mixture was concentrated under reduced pressure, and then the residue was purified by silica gel column chromatography (eluate: chloroform/methanol=95/5) to give Compound 89 (0.076 mg).

Step (iv): Preparation of 2-methyl-1-(6-{[5-(2,2,2-trifluoroethyl)pyridin-2-yl]oxy}-1H-benzimidazol-1-yl)propan-2-ol (Compound 60)

To a solution of Compound 89 (0.076 mg) in methanol (2 mL) was added potassium carbonate (100 mg), and the mixture was stirred at room temperature for 2 hours. The reaction mixture was filtered, and the filtrate was concentrated under reduced pressure. The residue was purified by silica gel column chromatography (eluate: chloroform/methanol=95/5) to give Compound 60 (0.055 g).
$^1$H-NMR (CDCl$_3$) 1.22 (6H, s), 3.21-3.29 (2H, m), 4.01 (2H, s), 6.84 (6H, s), 6.94-6.99 (1H, m), 7.21 (2H, s), 7.56 (1H, d, J=8.2 Hz), 7.69 (1H, dd, J=8.7, 2.3 Hz), 7.88 (1H, s), 7.98 (1H, s).

Examples 90-115

Examples 90 to 115 shown in the following table were prepared according to the process of Example 1 by using each appropriate starting material.

TABLE 7

| Example | Chemical Structure | Spectrum data |
| --- | --- | --- |
| 90 | 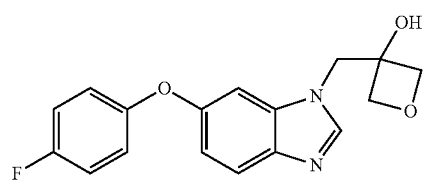 [SMILES: OC1(Cn2cnc3ccc(Oc4ccc(F)cc4)cc32)COC1] | $^1$H-NMR (CDCl$_3$) δ: 4.54 (2H, s), 4.58 (4H, dd, J = 55.5, 7.9 Hz), 6.93-7.05 (5H, m), 7.14 (1H, d, J = 2.4 Hz), 7.64 (1H, d, J = 9.2 Hz), 8.27 (1H, d, J = 4.3 Hz). |
| 91 | 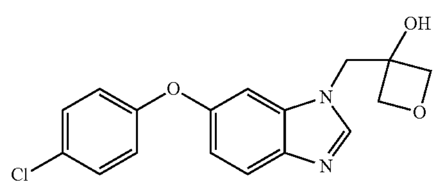 [SMILES: OC1(Cn2cnc3ccc(Oc4ccc(Cl)cc4)cc32)COC1] | $^1$H-NMR (CDCl$_3$) δ: 4.55 (2H, s), 4.58 (4H, dd, J = 53.1, 7.9 Hz), 6.89-6.91 (2H, m), 6.99 (1H, dd, J = 9.2, 2.4 Hz), 7.19 (1H, d, J = 1.8 Hz), 7.26-7.28 (2H, m), 7.65 (1H, d, J = 8.5 Hz), 8.26 (1H, s). |
| 92 | 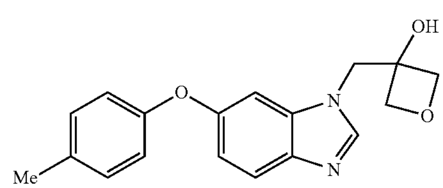 [SMILES: Cc1ccc(Oc2ccc3ncn(CC4(O)COC4)c3c2)cc1] | $^1$H-NMR (CDCl$_3$) δ: 2.32 (3H, s), 4.52 (2H, s), 4.58 (4H, dd, J = 55.5, 7.9 Hz), 6.87-6.89 (2H, m), 6.98 (1H, dd, J = 8.9, 2.1 Hz), 7.12-7.13 (3H, m), 7.60 (1H, d, J = 8.5 Hz), 8.21 (1H, s). |
| 93 | 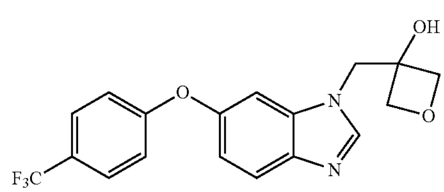 [SMILES: OC1(Cn2cnc3ccc(Oc4ccc(C(F)(F)F)nc4)cc32)COC1] | $^1$H-NMR (CDCl$_3$) δ: 4.50 (2H, s), 4.59 (4H, dd, J = 27.4, 8.2 Hz), 6.95-7.00 (3H, m), 7.24-7.25 (1H, m), 7.53 (2H, d, J = 9.1 Hz), 7.64 (1H, d, J = 8.7 Hz), 7.96 (1H, s). |

TABLE 7-continued

| Example | Chemical Structure | Spectrum data |
| --- | --- | --- |
| 94 | [structure: 4-(trifluoromethoxy)phenoxy-benzimidazole with oxetane-methyl-OH substituent] | $^1$H-NMR (CDCl$_3$) δ: 4.57 (2H, s), 4.59 (4H, dd, J = 52.5, 7.9 Hz), 6.94-7.02 (3H, m), 7.16 (2H, m), 7.23 (1H, d, J = 1.8 Hz), 7.68 (1H, d, J = 8.5 Hz), 8.31 (1H, s). XRD; 2θ = 7.7, 11.5, 15.4, 17.4, 17.8, 19.3, 21.2, 21.9, 22.5, 23.1, 23.5, 25.6, 26.1, 27.0, 31.0, 32.3, 33.2, 35.0, 36.0, 39.0 |
| 95 | [structure: 3-fluorophenoxy-benzimidazole with oxetane-methyl-OH substituent] | $^1$H-NMR (CDCl$_3$) δ: 4.58 (2H, s), 4.59 (4H, dd, J = 54.3, 7.3 Hz), 6.66 (1H, dd, J = 10.4, 2.4 Hz), 6.75-6.79 (2H, m), 7.03 (1H, d, J = 9.2 Hz), 7.25-7.27 (2H, m), 7.68 (1H, d, J = 8.5 Hz), 8.32 (1H, s). |
| 96 | [structure: 6-(trifluoromethyl)pyridin-3-yloxy-benzimidazole with oxetane-methyl-OH substituent] | $^1$H-NMR (CDCl$_3$) δ: 4.58 (4H, dd, J = 58.0, 7.9 Hz), 4.65 (2H, s), 7.11 (1H, dd, J = 8.5, 2.4 Hz), 7.34 (1H, dd, J = 8.9, 2.7 Hz), 7.36 (1H, d, J = 2.4 Hz), 7.63 (1H, d, J = 8.5 Hz), 7.83 (1H, d, J = 9.2 Hz), 8.44 (1H, d, J = 3.1 Hz), 8.60 (1H, s). |
| 97 | [structure: 4-(trifluoromethoxy)phenoxy-benzimidazole with 3-hydroxy-3-methylbutyl substituent] | $^1$H-NMR (CDCl$_3$) δ: 1.29 (6H, s), 1.99-2.01 (2H, m), 4.28 (2H, t, J = 7.6 Hz), 6.94-6.96 (3H, m), 7.08 (1H, s), 7.15 (2H, m), 7.74 (1H, d, J = 8.5 Hz), 7.97 (1H, s). |
| 98 | [structure: 3-fluorophenoxy-benzimidazole with 3-hydroxy-3-methylbutyl substituent] | $^1$H-NMR (CDCl$_3$) δ: 1.30 (6H, s), 2.02 (2H, d, J = 13.4 Hz), 4.27-4.30 (2H, br m), 6.66-6.72 (3H, m), 6.99 (1H, d, J = 6.1 Hz), 7.10 (1H, s), 7.24 (1H, s), 7.74 (1H, d, J = 7.9 Hz), 7.95 (1H, s). |
| 99 | [structure: 4-methylphenoxy-benzimidazole with 3-hydroxy-3-methylbutyl substituent] | $^1$H-NMR (CDCl$_3$) δ: 1.29 (6H, s), 2.00 (2H, t, J = 7.9 Hz), 2.31 (3H, s), 4.28 (2H, dd, J = 8.9, 7.0 Hz), 6.89 (2H, m), 6.99 (1H, d, J = 8.5 Hz), 7.05 (1H, d, J = 1.8 Hz), 7.11 (2H, m), 7.72 (1H, d, J = 8.5 Hz), 8.12 (1H, s). |
| 100 | [structure: 4-fluorophenoxy-benzimidazole with 3-hydroxy-3-methylbutyl substituent] | $^1$H-NMR (CDCl$_3$) δ: 1.29 (6H, s), 2.00 (2H, t, J = 7.9 Hz), 4.28 (2H, m), 6.93-7.03 (6H, m), 7.73 (1H, d, J = 8.5 Hz), 8.07 (1H, s). |

TABLE 7-continued

| Example | Chemical Structure | Spectrum data |
|---|---|---|
| 101 | 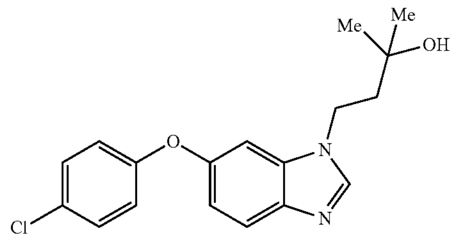 [SMILES: CC(C)(O)CCn1cnc2ccc(Oc3ccc(Cl)cc3)cc21] | $^{1}$H-NMR (CDCl$_3$) δ: 1.30 (6H, s), 1.99-2.03 (2H, m), 4.28-4.32 (2H, m), 6.90-6.91 (2H, m), 6.98 (1H, dd, J = 8.5, 2.4 Hz), 7.07 (1H, d, J = 2.4 Hz), 7.26-7.27 (2H, m), 7.75 (1H, d, J = 9.2 Hz), 8.12 (1H, br s).<br>XRD; 2θ = 7.7, 15.3, 16.2, 16.4, 17.0, 18.9, 20.2, 20.3, 20.9, 21.2, 23.7, 24.4, 25.4, 27.5, 28.3, 28.6, 29.0, 31.0, 32.0, 34.5 |
| 102 | 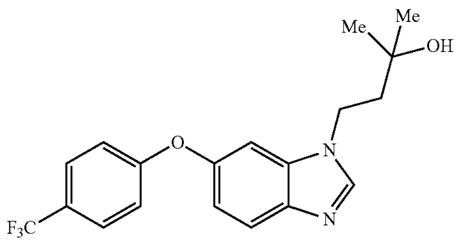 [SMILES: CC(C)(O)CCn1cnc2ccc(Oc3ccc(C(F)(F)F)cc3)cc21] | $^{1}$H-NMR (CDCl$_3$) δ: 1.26 (6H, s), 1.97-2.01 (2H, m), 4.28-4.32 (2H, m), 6.96-7.01 (3H, m), 7.10 (1H, d, J = 2.4 Hz), 7.51 (2H, m), 7.77 (1H, d, J = 9.2 Hz), 8.27-8.28 (1H, br m). |
| 103 | 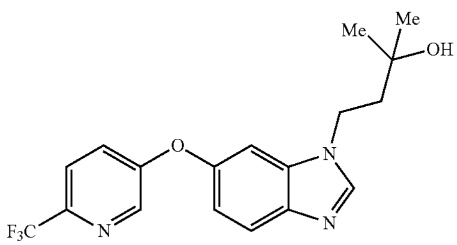 | $^{1}$H-NMR (CDCl$_3$) δ: 1.31 (6H, s), 2.02-2.08 (2H, m), 4.37 (2H, t, J = 7.9 Hz), 7.07 (1H, dd, J = 8.9, 2.1 Hz), 7.19 (1H, d, J = 1.8 Hz), 7.30 (1H, dd, J = 8.9, 2.7 Hz), 7.61 (1H, d, J = 9.2 Hz), 7.86 (1H, d, J = 8.5 Hz), 8.40 (1H, s), 8.46 (1H, d, J = 2.4 Hz). |
| 104 | 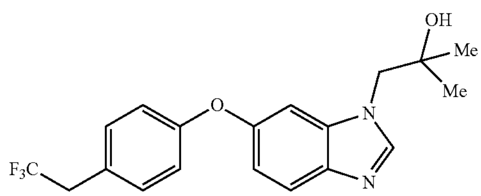 [SMILES: CC(C)(O)Cn1cnc2ccc(Oc3ccc(CC(F)(F)F)cc3)cc21] | $^{1}$H-NMR (CDCl$_3$) δ: 1.27 (6H, s), 3.27-3.35 (2H, m), 4.03 (2H, s), 6.90-6.97 (3H, m), 7.09 (1H, d, J = 2.4 Hz), 7.20 (2H, m), 7.67 (1H, d, J = 8.5 Hz), 7.92 (1H, s). |
| 105 | 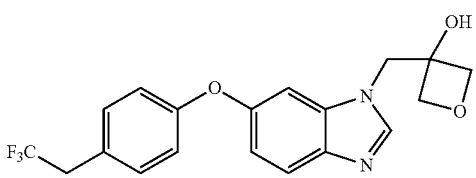 [SMILES: OC1(Cn2cnc3ccc(Oc4ccc(CC(F)(F)F)cc4)cc32)COC1] | $^{1}$H-NMR (CDCl$_3$) δ: 3.31 (2H, q, J = 10.8 Hz), 4.48 (2H, s), 4.59 (4H, dd, J = 27.2, 7.6 Hz), 6.91-6.97 (3H, m), 7.19-7.22 (3H, m), 7.60 (1H, d, J = 8.5 Hz), 7.93 (1H, s). |
| 106 | 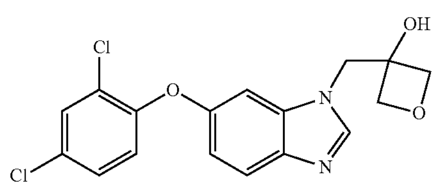 [SMILES: OC1(Cn2cnc3ccc(Oc4ccc(Cl)cc4Cl)cc32)COC1] | $^{1}$H-NMR (DMSO-d6) δ: 4.43 (4H, dd, J = 37.5, 7.0 Hz), 4.51 (2H, s), 6.17 (1H, s), 6.91-6.94 (2H, m), 7.36 (1H, dd, J = 8.5, 2.4 Hz), 7.40 (1H, d, J = 1.8 Hz), 7.64 (1H, d, J = 9.2 Hz), 7.75 (1H, d, J = 2.4 Hz), 8.26 (1H, s). |
| 107 | 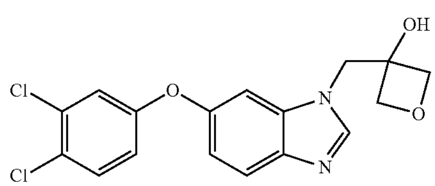 [SMILES: OC1(Cn2cnc3ccc(Oc4ccc(Cl)c(Cl)c4)cc32)COC1] | $^{1}$H-NMR (CDCl$_3$) δ: 4.08 (1H, s), 4.50 (2H, s), 4.60 (4H, dd, J = 31.0, 7.8 Hz), 6.82 (1H, m), 6.93 (1H, m), 7.02 (1H, dd, 2.4, 2.4 Hz), 7.20 (1H, dd, J = 2.1, 2.1 Hz), 7.34 (1H, dd, J = 8.9, 2.1 Hz), 7.61 (1H, dd, J = 8.9, 2.1 Hz), 7.94 (1H, d, J = 2.4 Hz). |

TABLE 7-continued

| Example | Chemical Structure | Spectrum data |
|---|---|---|
| 108 | (structure) | LCMS: T = 0.782, m/z = 399, 401 |
| 109 | (structure) | ¹H-NMR (CDCl₃) δ: 4.48 (2H, s), 4.58 (4H, dd, J = 23.5, 7.6 Hz), 6.89-6.94 (2H, m), 7.03-7.06 (1H, m), 7.12 (1H, d, J = 2.4 Hz), 7.20 (1H, dd, J = 10.4, 2.4 Hz), 7.58 (1H, d, J = 9.2 Hz), 7.91 (1H, s). |
| 110 | (structure) | ¹H-NMR (CDCl₃) δ: 4.48 (2H, s), 4.57 (4H, dd, J = 11.3, 7.6 Hz), 6.91 (3H, m), 7.07 (1H, d, J = 2.4 Hz), 7.20-7.23 (1H, m), 7.66 (1H, d, J = 8.5 Hz), 7.95 (1H, s). |
| 111 | (structure) | ¹H-NMR (CDCl₃) δ: 4.19 (1H, br s), 4.51 (2H, s), 4.61 (4H, dd, J = 33.0, 7.9 Hz), 6.81 (2H, ,), 6.94 (1H, dd, J = 8.5, 2.4 Hz), 7.03 (1H, dd, J = 1.8, 1.8 Hz), 7.22 (1H, d, J = 2.4 Hz), 7.61 (1H, d, J = 8.5 Hz), 7.95 (1H, s). |
| 112 | (structure) | ¹H-NMR (CDCl₃) δ: 4.51 (2H, s), 4.57-4.59 (4H, m), 6.81 (1H, d, J = 2.4 Hz), 6.96-7.02 (2H, m), 7.20 (1H, d, J = 1.8 Hz), 7.37 (1H, d, J = 8.5 Hz), 7.73 (1H, d, J = 8.5 Hz), 8.00 (1H, s). |
| 113 | (structure) | ¹H-NMR (DMSO-d6) δ: 1.33 (3H, s), 2.63-2.59 (2H, m), 2.54-2.50 (2H, m), 5.28 (1H, s), 7.00 (1H, dd, J = 8.8, 2.4 Hz), 7.08 (2H, m), 7.54 (1H, d, J = 1.6 Hz), 7.69 (2H, m), 7.71 (1H, d, J = 8.8 Hz), 8.39 (1H, s). |
| 114 | (structure) | ¹H-NMR (DMSO-d6) δ: 4.38 (2H, d, J = 6.8 Hz), 4.48 (2H, d, J = 6.8 Hz), 4.51 (2H, s), 6.17 (1H, m), 6.97-7.00 (1H, m), 7.23 (1H, d, J = 8.8, 2.4 Hz), 7.46 (1H, d, J = 2.4 Hz), 7.54 (1H, d, J = 2.4 Hz), 7.66 (1H, d, J = 8.8 Hz), 8.14 (1H, d, J = 8.8 Hz), 8.26 (1H, s), 9.39 (1H, s). |

TABLE 7-continued

| Example | Chemical Structure | Spectrum data |
|---|---|---|
| 115 | 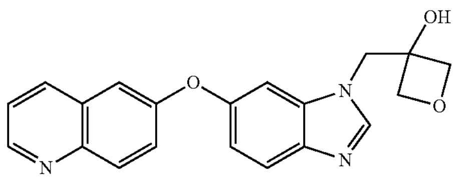 [SMILES: OC1(Cn2cnc3ccc(Oc4ccc5ncccc5c4)cc32)COC1] | $^1$H-NMR (DMSO-d6) δ: 4.38 (2H, d, J = 6.8 Hz), 4.48 (2H, d, J = 6.8 Hz), 4.52 (2H, s), 6.18 (1H, m), 7.03 (1H, dd, J = 8.4, 2.4 Hz), 7.30 (1H, d, J = 2.4 Hz), 7.46 (1H, dd, J = 8.0, 4.4 Hz), 7.53-7.57 (2H, m), 7.68-7.70 (1H, m), 8.01-8.04 (1H, m), 8.20-8.22 (1H, m), 8.28 (1H, s), 8.78 (1H, dd, J = 2.0, 4.4 Hz). |

Examples 116-121

Examples 116 to 121 shown in the following table were prepared according to the process of Example 59 by using each appropriate starting material.

TABLE 8

| Example | Chemical Structure | Spectrum data |
|---|---|---|
| 116 | 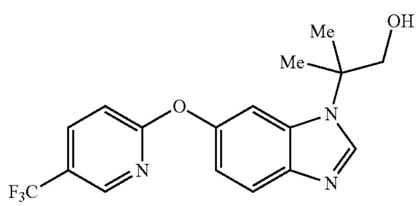 [SMILES: CC(C)(CO)n1cnc2ccc(Oc3ccc(C(F)(F)F)cn3)cc21] | $^1$H-NMR (CDCl$_3$) δ: 1.73 (6H, s), 3.94 (2H, s), 7.00 (2H, m), 7.39 (1H, d, J = 2.4 Hz), 7.70 (1H, d, J = 8.5 Hz), 7.88 (1H, dd, J = 8.9, 2.1 Hz), 7.97 (1H, s), 8.40 (1H, s). |
| 117 | 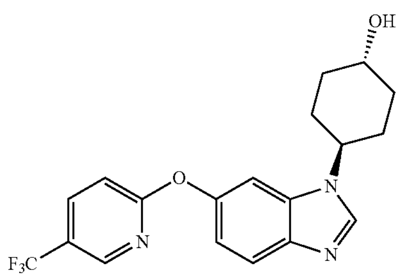 [SMILES: O[C@H]1CC[C@H](n2cnc3ccc(Oc4ccc(C(F)(F)F)cn4)cc32)CC1] | $^1$H-NMR (CDCl$_3$) δ: 1.43-1.54 (2H, m), 1.78-1.92 (2H, m), 2.11-2.22 (4H, m), 3.75 (1H, tt, J = 10.7, 4.4 Hz), 4.11 (1H, tt, J = 12.2, 3.8 Hz), 6.97 (1H, d, J = 8.5 Hz), 7.01 (1H, dd, J = 8.5, 2.4 Hz), 7.17 (1H, d, J = 2.4 Hz), 7.77 (1H, d, J = 8.5 Hz), 7.85 (1H, dd, J = 8.9, 2.7 Hz), 7.99 (1H, s), 8.37 (1H, d, J = 1.8 Hz). |
| 118 | 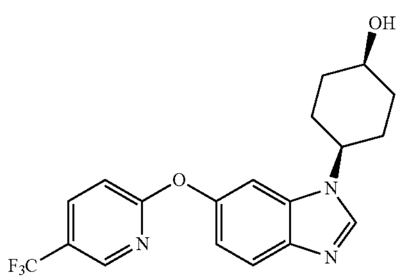 [SMILES: O[C@H]1CC[C@@H](n2cnc3ccc(Oc4ccc(C(F)(F)F)cn4)cc32)CC1] | $^1$H-NMR (CDCl$_3$) δ: 1.46 (1H, d, J = 2.4 Hz), 1.67-1.76 (2H, m), 1.95-2.03 (4H, m), 2.27-2.36 (2H, m), 4.12-4.19 (2H, m), 7.02 (2H, m), 7.22-7.24 (1H, m), 7.82 (1H, d, J = 9.2 Hz), 7.88 (1H, dd, J = 8.5, 2.4 Hz), 8.04 (1H, s), 8.42 (1H, s). |
| 119 | 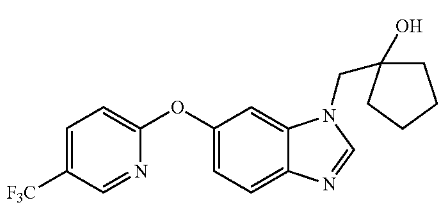 [SMILES: OC1(Cn2cnc3ccc(Oc4ccc(C(F)(F)F)cn4)cc32)CCCC1] | $^1$H-NMR (CDCl$_3$) δ: 1.60-1.87 (8H, m), 4.21 (2H, s), 7.00 (1H, d, J = 8.5 Hz), 7.03 (1H, dd, J = 8.5, 2.4 Hz), 7.29 (1H, d, J = 2.4 Hz), 7.78 (1H, d, J = 9.2 Hz), 7.88 (1H, dd, J = 8.5, 2.4 Hz), 8.00 (1H, s), 8.40 (1H, s). |

TABLE 8-continued

| Example | Chemical Structure | Spectrum data |
|---|---|---|
| 120 | (5-(trifluoromethoxy)pyridin-2-yl)oxy-benzimidazole with N-CH₂-C(Me)₂-OH substituent | ¹H-NMR (CDCl₃) δ: 1.28 (6H, s), 1.61 (1H, s), 4.07 (2H, s), 6.94 (1H, d, J = 8.5 Hz), 7.04 (1H, dd, J = 8.5, 2.4 Hz), 7.25 (1H, d, J = 2.4 Hz), 7.53-7.57 (1H, m), 7.79 (1H, d, J = 8.5 Hz), 7.96 (1H, s), 8.07 (1H, d, J = 3.1 Hz). |
| 121 | (5-(trifluoromethoxy)pyridin-2-yl)oxy-benzimidazole with N-cyclobutyl-Me-OH substituent | ¹H-NMR (DMSO-d6) δ: 1.33 (3H, s), 2.59-2.64 (2H, m), 2.51-2.54 (2H, m), 5.28 (1H, s), 7.02-7.04 (1H, m), 7.20 (1H, d, J = 8.8 Hz), 7.56-7.57 (1H, m), 7.68 (1H, d, J = 8.8 Hz), 8.21 (1H, dd, J = 2.4, 8.8 Hz), 8.38 (1H, s), 8.54-8.55 (1H, m). |

Examples 122-174

Examples 122 to 174 shown in the following table were prepared according to the process of Example 5 by using each appropriate starting material.

TABLE 9

| Example | Chemical Structure | Spectrum data |
|---|---|---|
| 122 | 6-(trifluoromethyl)pyridin-3-yl-benzimidazole with N-CH₂-C(Me)₂-OH substituent | ¹H-NMR (CDCl₃) δ: 1.32 (6H, s), 4.27 (2H, s), 7.53 (1H, d, J = 8.5 Hz), 7.69 (1H, d, J = 1.2 Hz), 7.76 (1H, d, J = 8.5 Hz), 7.93 (1H, d, J = 8.5 Hz), 8.06 (1H, dd, J = 7.9, 1.8 Hz), 8.45 (1H, d, J = 7.9 Hz), 8.96 (1H, d, J = 2.4 Hz). |
| 123 | 4-(trifluoromethyl)-2-fluorophenyl-benzimidazole with N-CH₂-C(Me)₂-OH substituent | ¹H-NMR (CDCl₃) δ: 1.31 (6H, s), 4.23 (2H, s), 7.45-7.47 (3H, m), 7.60 (1H, dd, J = 7.6, 7.6 Hz), 7.66 (1H, s), 7.88 (1H, d, J = 8.5 Hz), 8.36 (1H, s). |
| 124 | 4-(trifluoromethyl)-2-methoxyphenyl-benzimidazole with N-CH₂-C(Me)₂-OH substituent | ¹H-NMR (CDCl₃) δ: 1.31 (6H, s), 3.84 (3H, s), 4.22 (2H, s), 7.19 (1H, s), 7.30 (1H, d, J = 7.9 Hz), 7.44 (2H, m), 7.62 (1H, s), 7.84 (1H, d, J = 8.5 Hz), 8.38 (1H, s). |
| 125 | 6-methoxypyridin-3-yl-benzimidazole with N-CH₂-C(Me)₂-OH substituent | ¹H-NMR (CDCl₃) δ: 1.31 (6H, s), 3.97 (3H, s), 4.24 (2H, s), 6.82 (1H, d, J = 8.5 Hz), 7.46 (1H, dd, J = 8.2, 1.5 Hz), 7.57 (1H, s), 7.81 (1H, dd, J = 8.5, 2.4 Hz), 7.85 (1H, d, J = 8.5 Hz), 8.38-8.41 (2H, br m). |

TABLE 9-continued

| Example | Chemical Structure | Spectrum data |
|---|---|---|
| 126 | (Me-pyridin-3-yl)-benzimidazole with 2-hydroxy-2-methylpropyl | $^1$H-NMR (CDCl$_3$) δ: 1.32 (6H, s), 2.62 (3H, s), 4.20 (2H, s), 7.26 (1H, d, J = 9.8 Hz), 7.44 (1H, d, J = 8.5 Hz), 7.65 (1H, s), 7.84-7.86 (2H, m), 8.09 (1H, s), 8.74 (1H, s). |
| 127 | (6-morpholinopyridin-3-yl)-benzimidazole with 2-hydroxy-2-methylpropyl | $^1$H-NMR (CDCl$_3$) δ: 1.31 (6H, s), 3.57 (4H, t, J = 4.9 Hz), 3.84 (4H, t, J = 4.9 Hz), 4.24 (2H, s), 6.73 (1H, d, J = 8.5 Hz), 7.46 (1H, dd, J = 8.2, 1.5 Hz), 7.57 (1H, s), 7.79 (1H, dd, J = 8.5, 2.4 Hz), 7.84 (1H, d, J = 8.5 Hz), 8.39 (1H, s), 8.46 (1H, d, J = 2.4 Hz). |
| 128 | (4-fluoro-2-methoxyphenyl)-benzimidazole with 2-hydroxy-2-methylpropyl | $^1$H-NMR (CDCl$_3$) δ: 1.30 (6H, s), 1.73 (1H, br s), 3.78 (3H, s), 4.13 (2H, s), 6.69-6.76 (2H, m), 7.28 (1H, dd, J = 7.5, 7.5 Hz), 7.35 (1H, dd, J = 8.7, 1.4 Hz), 7.54 (1H, s), 7.78 (1H, d, J = 8.7 Hz), 7.96 (1H, s). |
| 129 | (4-chloro-2-methylphenyl)-benzimidazole with 2-hydroxy-2-methylpropyl | $^1$H-NMR (CDCl$_3$) δ: 1.30 (6H, s), 1.75 (1H, s), 2.22 (3H, s), 4.11 (2H, s), 7.14-7.20 (3H, m), 7.25 (1H, s), 7.32 (1H, d, J = 1.4 Hz), 7.78 (1H, d, J = 8.2 Hz), 7.99 (1H, s). |
| 130 | (4-chloro-2-fluorophenyl)-benzimidazole with 2-hydroxy-2-methylpropyl | $^1$H-NMR (CDCl$_3$) δ: 1.30 (6H, s), 1.86 (1H, s), 4.14 (2H, s), 7.17-7.23 (2H, m), 7.35-7.43 (2H, m), 7.59-7.59 (1H, br m), 7.81 (1H, d, J = 8.2 Hz), 7.99 (1H, s). |
| 131 | (4-chloro-2-trifluoromethylphenyl)-benzimidazole with 2-hydroxy-2-methylpropyl | $^1$H-NMR (CDCl$_3$) δ: 1.27 (6H, s), 1.70 (1H, s), 4.10 (2H, s), 7.16 (1H, d, J = 8.2 Hz), 7.31 (1H, d, J = 8.2 Hz), 7.36 (1H, s), 7.51 (1H, d, J = 8.2 Hz), 7.72 (1H, s), 7.77 (1H, d, J = 8.2 Hz), 8.01 (1H, s). |
| 133 | (2,4-dichlorophenyl)-benzimidazole with 2-hydroxy-2-methylpropyl | $^1$H-NMR (CDCl$_3$) δ: 1.30 (6H, s), 1.72 (1H, s), 4.13 (2H, s), 7.23-7.33 (3H, m), 7.49 (2H, m), 7.81 (1H, d, J = 7.9 Hz), 8.01 (1H, s). |

TABLE 9-continued

| Example | Chemical Structure | Spectrum data |
|---|---|---|
| 133 | 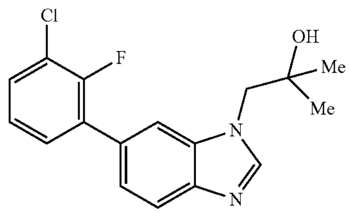 [SMILES: CC(C)(O)Cn1cnc2ccc(-c3cccc(Cl)c3F)cc21] | ¹H-NMR (CDCl₃) δ: 1.31 (6H, s), 1.82 (1H, s), 4.15 (2H, s), 7.14 (1H, m), 7.34-7.40 (3H, m), 7.62 (1H, s), 7.82 (1H, d, J = 8.5 Hz), 8.01 (1H, s). |
| 134 | 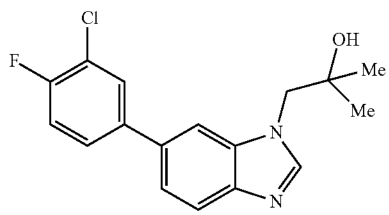 [SMILES: CC(C)(O)Cn1cnc2ccc(-c3ccc(F)c(Cl)c3)cc21] | ¹H-NMR (CDCl₃) δ: 1.32 (6H, s), 1.82 (1H, s), 4.16 (2H, s), 7.19 (1H, dd, J = 8.9, 8.9 Hz), 7.39 (1H, dd, J = 8.5, 1.8 Hz), 7.42-7.47 (1H, m), 7.54 (1H, d, J = 1.8 Hz), 7.62 (1H, dd, J = 6.7, 2.4 Hz), 7.80 (1H, d, J = 8.5 Hz), 7.99 (1H, s). |
| 135 | 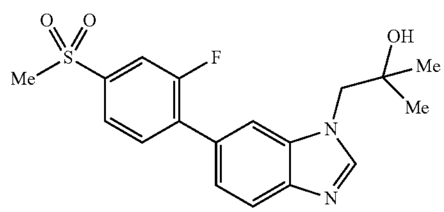 [SMILES: CC(C)(O)Cn1cnc2ccc(-c3ccc(S(C)(=O)=O)cc3F)cc21] | ¹H-NMR (CDCl₃) δ: 1.31 (6H, s), 1.79 (1H, br s), 3.10 (3H, s), 4.16 (2H, s), 7.42 (1H, m), 7.66-7.71 (2H, m), 7.77 (2H, m), 7.85 (1H, d, J = 8.5 Hz), 8.03 (1H, s). |
| 136 | 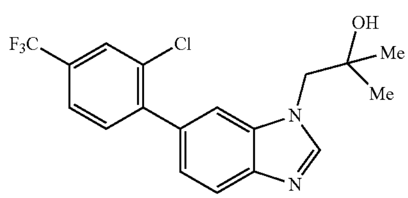 [SMILES: CC(C)(O)Cn1cnc2ccc(-c3ccc(C(F)(F)F)cc3Cl)cc21] | ¹H-NMR (CDCl₃) δ: 1.30 (6H, s), 1.80 (1H, s), 4.12 (2H, s), 7.26-7.30 (1H, m), 7.47-7.58 (3H, m), 7.74 (1H, s), 7.79-7.84 (1H, m), 8.00-8.02 (1H, m). |
| 137 | 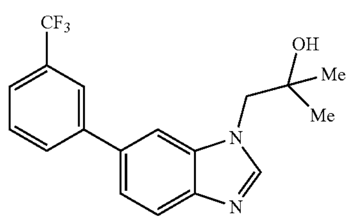 | ¹H-NMR (CDCl₃) δ: 1.32 (6H, s), 1.75 (1H, s), 4.18 (2H, s), 7.46-7.63 (4H, m), 7.78 (1H, d, J = 7.3 Hz), 7.83-7.85 (2H, m), 8.02 (1H, s). |
| 138 | 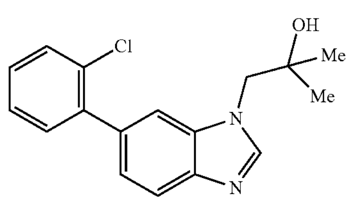 [SMILES: CC(C)(O)Cn1cnc2ccc(-c3ccccc3Cl)cc21] | ¹H-NMR (CDCl₃) δ: 1.30 (6H, s), 1.58 (1H, s), 4.13 (2H, s), 7.26-7.32 (3H, m), 7.36-7.39 (1H, m), 7.45-7.49 (1H, m), 7.51 (1H, s), 7.79 (1H, d, J = 8.5 Hz), 8.00 (1H, s). |
| 139 | 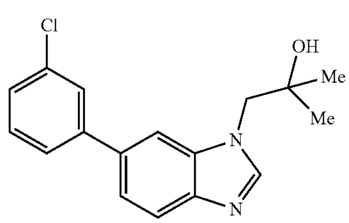 [SMILES: CC(C)(O)Cn1cnc2ccc(-c3cccc(Cl)c3)cc21] | ¹H-NMR (CDCl₃) δ: 1.32 (6H, s), 1.87 (1H, s), 4.16 (2H, s), 7.28-7.32 (1H, m), 7.36 (1H, m), 7.43-7.49 (2H, m), 7.59 (2H, s), 7.80 (1H, d, J = 8.2 Hz), 7.99 (1H, s). |

TABLE 9-continued

| Example | Chemical Structure | Spectrum data |
|---|---|---|
| 140 | 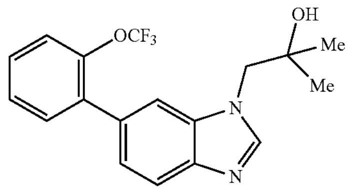 [SMILES: CC(C)(O)Cn1cnc2ccc(-c3ccccc3OC(F)(F)F)cc21] | $^1$H-NMR (CDCl$_3$) δ: 1.30 (6H, s), 1.69 (1H, s), 4.13 (2H, s), 7.31-7.37 (4H, m), 7.45-7.49 (1H, m), 7.53 (1H, d, J = 0.9 Hz), 7.81 (1H, d, J = 8.2 Hz), 8.01 (1H, s). |
| 141 | 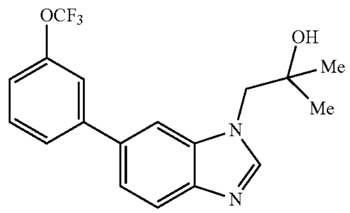 [SMILES: CC(C)(O)Cn1cnc2ccc(-c3cccc(OC(F)(F)F)c3)cc21] | $^1$H-NMR (CDCl$_3$) δ: 1.32 (6H, s), 1.84 (1H, s), 4.17 (2H, s), 7.17-7.20 (1H, m), 7.42-7.47 (3H, m), 7.53 (1H, dd, J = 7.9, 1.2 Hz), 7.59 (1H, d, J = 1.2 Hz), 7.82 (1H, d, J = 8.5 Hz), 8.00 (1H, s). |
| 142 | 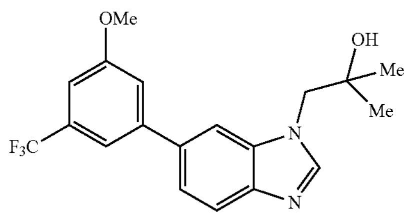 [SMILES: COc1cc(-c2ccc3ncn(CC(C)(C)O)c3c2)cc(C(F)(F)F)c1] | $^1$H-NMR (CDCl$_3$) δ: 1.32 (6H, s), 1.76 (1H, s), 3.90 (3H, s), 4.17 (2H, s), 7.09 (1H, s), 7.29 (1H, s), 7.43 (1H, s), 7.46 (1H, dd, J = 8.2, 1.5 Hz), 7.59 (1H, s), 7.82 (1H, d, J = 8.5 Hz), 8.01 (1H, s). |
| 143 | 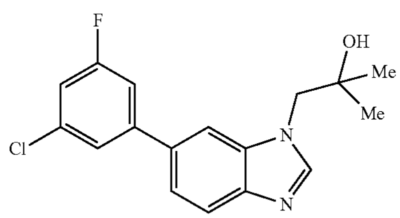 [SMILES: CC(C)(O)Cn1cnc2ccc(-c3cc(F)cc(Cl)c3)cc21] | $^1$H-NMR (CDCl$_3$) δ: 1.32 (6H, s), 1.74 (1H, s), 4.17 (2H, s), 7.05 (1H, ddd, J = 8.2, 2.1, 2.1 Hz), 7.21 (1H, ddd, J = 9.8, 1.8, 1.8 Hz), 7.39 (1H, dd, J = 1.5, 1.5 Hz), 7.43 (1H, dd, J = 8.5, 1.8 Hz), 7.58 (1H, d, J = 1.8 Hz), 7.82 (1H, d, J = 8.5 Hz), 8.01 (1H, s). |
| 144 | 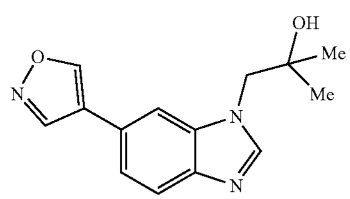 [SMILES: CC(C)(O)Cn1cnc2ccc(-c3cnoc3)cc21] | $^1$H-NMR (DMSO-d6) δ: 1.12 (6H, s), 4.16 (2H, s), 4.80 (1H, s), 7.50 (1H, dd, J = 8.4, 2.0 Hz), 7.66 (1H, d, J = 8.4 Hz), 7.99-8.00 (1H, m), 8.13 (1H, s), 9.16 (1H, s), 9.40 (1H, s). |
| 145 | 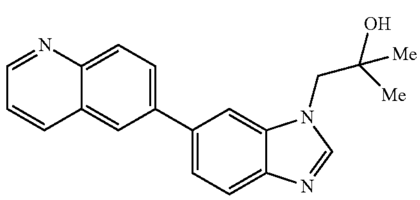 [SMILES: CC(C)(O)Cn1cnc2ccc(-c3ccc4ncccc4c3)cc21] | $^1$H-NMR (DMSO-d6) δ: 1.14 (6H, s), 4.25 (2H, s), 4.82 (1H, s), 7.54-7.57 (1H, m), 7.64-7.67 (1H, m), 7.75 (1H, d, J = 8.0 Hz), 8.10 (1H, d, J = 9.2 Hz), 8.15-8.19 (3H, m), 8.29-8.30 (1H, m), 8.43 (1H, dd, J = 8.8, 1.2 Hz), 8.88-8.89 (1H, m). |
| 146 | 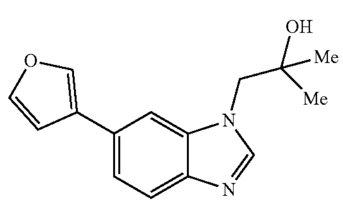 [SMILES: CC(C)(O)Cn1cnc2ccc(-c3ccoc3)cc21] | $^1$H-NMR (DMSO-d6) δ: 1.11 (6H, s), 4.16 (2H, s), 4.77 (1H, s), 6.99-7.00 (1H, m), 7.42-7.44 (1H, m), 7.58-7.61 (1H, m), 7.73-7.74 (1H, m), 7.87 (1H, s), 8.08 (1H, s), 8.14-8.15 (1H, m). |

TABLE 9-continued

| Example | Chemical Structure | Spectrum data |
|---|---|---|
| 147 | 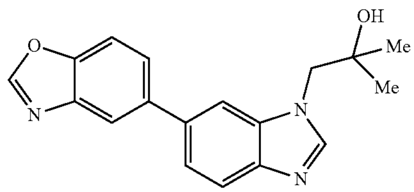 [SMILES: CC(C)(O)Cn1cnc2ccc(-c3ccc4ocnc4c3)cc21] | $^1$H-NMR (DMSO-d6) δ: 1.13 (6H, s), 4.23 (2H, s), 4.80 (1H, s), 7.54 (1H, dd, J = 8.4, 2.0 Hz), 7.69 (1H, d, J = 8.4 Hz), 7.77-7.80 (1H, m), 7.85 (1H, d, J = 8.4 H), 8.05 (1H, d, J = 1.2 Hz), 8.12 (1H, d, J = 1.2 Hz), 8.14 (1H, s), 8.78 (1H, s). |
| 148 | 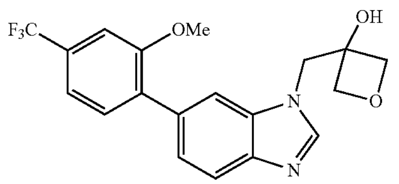 [SMILES: COc1cc(C(F)(F)F)ccc1-c1ccc2ncn(CC3(O)COC3)c2c1] | $^1$H-NMR (DMSO-d6) δ: 3.84 (3H, s), 4.42 (2H, d, J = 6.7 Hz), 4.54 (2H, d, J = 6.7 Hz), 4.59 (2H, s), 6.22 (1H, s), 7.33 (1H, dd, J = 8.2, 1.5 Hz), 7.37-7.41 (2H, m), 7.55 (1H, d, J = 7.9 Hz), 7.66 (1H, d, J = 8.5 Hz), 7.84 (1H, s), 8.28 (1H, s).<br>XRD; 2θ = 6.6, 13.0, 13.2, 13.6, 15.4, 18.0, 18.6, 19.6, 20.0, 21.0, 21.5, 21.8, 23.4, 24.0, 24.9, 25.7, 26.5, 27.5, 27.9, 29.3 |
| 149 | 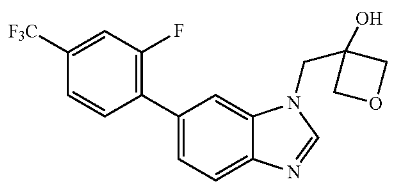 [SMILES: OC1(Cn2cnc3ccc(-c4ccc(C(F)(F)F)cc4F)cc32)COC1] | $^1$H-NMR (CDCl$_3$) δ: 4.61 (2H, s), 4.65 (4H, dd, J = 20.1, 7.9 Hz), 7.33 (1H, m), 7.46 (2H, m), 7.57 (1H, dd, J = 7.9, 7.9 Hz), 7.65 (1H, d, J = 8.5 Hz), 7.72 (1H, s), 7.99 (1H, s). |
| 150 | 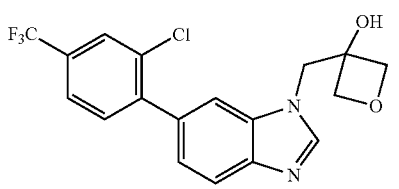 [SMILES: OC1(Cn2cnc3ccc(-c4ccc(C(F)(F)F)cc4Cl)cc32)COC1] | $^1$H-NMR (CDCl$_3$) δ: 4.59 (2H, s), 4.65 (4H, dd, J = 20.8, 7.9 Hz), 7.23 (1H, d, J = 6.7 Hz), 7.48 (1H, d, J = 7.9 Hz), 7.57 (1H, dd, J = 7.9, 1.2 Hz), 7.62 (1H, d, J = 1.2 Hz), 7.66 (1H, d, J = 8.5 Hz), 7.75 (1H, d, J = 1.2 Hz), 8.00 (1H, s). |
| 151 | 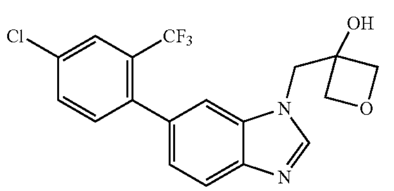 [SMILES: OC1(Cn2cnc3ccc(-c4ccc(Cl)cc4C(F)(F)F)cc32)COC1] | $^1$H-NMR (CDCl$_3$) δ: 4.56-4.63 (6H, m), 7.14 (1H, dd, J = 8.5, 1.2 Hz), 7.30 (1H, d, J = 7.9 Hz), 7.47 (1H, s), 7.52 (1H, dd, J = 8.2, 2.1 Hz), 7.68 (1H, d, J = 8.5 Hz), 7.73 (1H, d, J = 2.4 Hz), 8.01 (1H, s). |
| 152 | 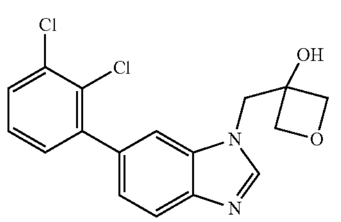 | $^1$H-NMR (CDCl$_3$) δ: 4.57-4.68 (6H, m), 7.19-7.25 (3H, m), 7.44-7.48 (1H, m), 7.57 (1H, s), 7.62 (1H, d, J = 8.2 Hz), 7.97 (1H, s). |
| 153 | 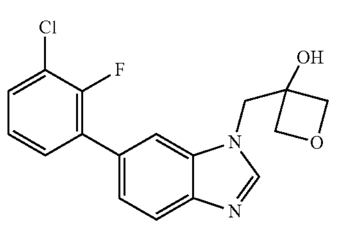 [SMILES: OC1(Cn2cnc3ccc(-c4cccc(Cl)c4F)cc32)COC1] | $^1$H-NMR (CDCl$_3$) δ: 4.57-4.68 (6H, m), 7.18-7.24 (3H, m), 7.45-7.46 (1H, m), 7.57 (1H, s, 7.62 (1H, d, J = 8.2 Hz), 7.97 (1H, s). |

TABLE 9-continued

| Example | Chemical Structure | Spectrum data |
| --- | --- | --- |
| 154 | 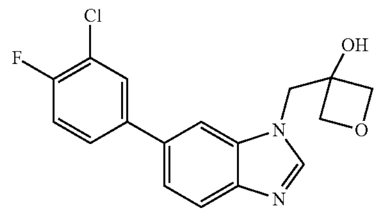 [SMILES: OC1(Cn2cnc3ccc(-c4ccc(F)c(Cl)c4)cc32)COC1] | ¹H-NMR (CDCl₃) δ: 4.49-4.58 (6H, m), 7.10 (1H, dd, J = 8.9, 8.9 Hz), 7.23 (1H, dd, J = 8.3, 1.5 Hz), 7.31-7.35 (1H, m), 7.48-7.55 (3H, m), 7.87 (1H, s). |
| 155 | 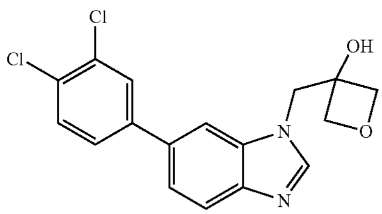 [SMILES: OC1(Cn2cnc3ccc(-c4ccc(Cl)c(Cl)c4)cc32)COC1] | ¹H-NMR (CDCl₃) δ: 4.60-4.67 (6H, m), 7.36 (1H, dd, J = 7.9, 1.8 Hz), 7.42 (1H, dd, J = 8.6, 2.4 Hz), 7.50 (1H, d, J = 7.9 Hz), 7.65-7.68 (3H, m), 7.99 (1H, s). |
| 156 | 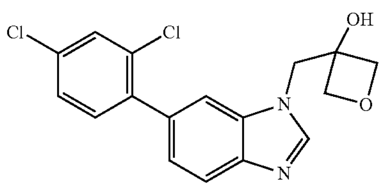 [SMILES: OC1(Cn2cnc3ccc(-c4ccc(Cl)cc4Cl)cc32)COC1] | ¹H-NMR (CDCl₃) δ: 4.58 (2H, s), 4.62-4.67 (4H, m), 7.20 (1H, dd, J = 8.3, 1.5 Hz), 7.28-7.29 (2H, m), 7.49 (1H, d, J = 1.8 Hz), 7.58 (1H, d, J = 1.2 Hz), 7.62 (1H, d, J = 3.6 Hz), 7.97 (1H, s). |
| 157 | 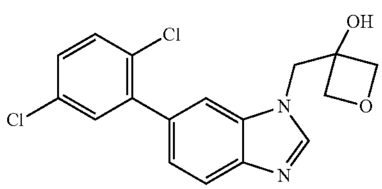 [SMILES: OC1(Cn2cnc3ccc(-c4cc(Cl)ccc4Cl)cc32)COC1] | ¹H-NMR (CDCl₃) δ: 4.59 (2H, s), 4.62-4.66 (4H, m), 7.21-7.28 (2H, m), 7.35 (1H, d, J = 2.4 Hz), 7.40 (1H, d, J = 8.6 Hz), 7.59 (1H, d, J = 1.2 Hz), 7.65 (1H, d, J = 8.6 Hz), 7.99 (1H, s). |
| 158 | 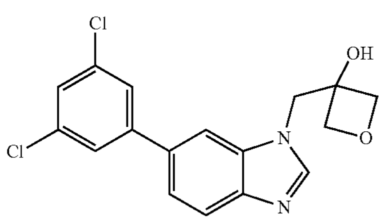 | ¹H-NMR (CDCl₃) δ: 4.56-4.63 (6H, m), 7.27-7.31 (2H, m), 7.41 (2H, m), 7.58-7.61 (2H, m), 7.93 (1H, s). |
| 159 | 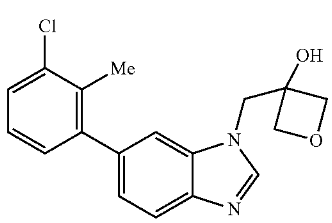 | ¹H-NMR (CDCl₃) δ: 2.25 (3H, s), 4.01 (1H, br s), 4.57-4.67 (6H, m), 7.11-7.18 (3H, m), 7.36 (1H, dd, J = 7.0, 2.7 Hz), 7.43 (1H, d, J = 1.2 Hz), 7.65 (1H, d, J = 8.5 Hz), 7.99 (1H, s). |
| 160 | 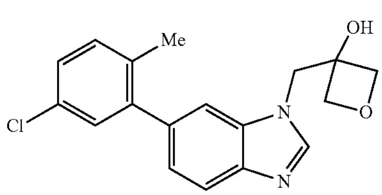 [SMILES: Cc1ccc(Cl)cc1-c1ccc2ncn(CC3(O)COC3)c2c1] | ¹H-NMR (CDCl₃) δ: 2.19 (3H, s), 4.23 (1H, s), 4.58-4.67 (6H, m), 7.13 (1H, dd, J = 8.2, 1.5 Hz), 7.17-7.24 (3H, m), 7.44 (1H, d, J = 1.8 Hz), 7.64 (1H, d, J = 7.9 Hz), 7.99 (1H, s). |

TABLE 9-continued

| Example | Chemical Structure | Spectrum data |
|---|---|---|
| 161 | 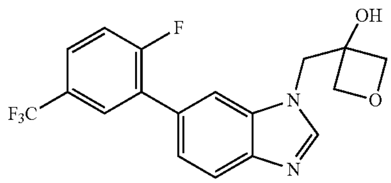 [SMILES: OC1(Cn2cnc3ccc(-c4cc(C(F)(F)F)ccc4F)cc32)COC1] | $^1$H-NMR (CDCl$_3$) δ: 3.80 (1H, s), 4.62-4.67 (6H, m), 7.24-7.30 (1H, m), 7.34 (1H, m), 7.57-7.62 (1H, m), 7.67-7.74 (3H, m), 8.01 (1H, s). |
| 162 | 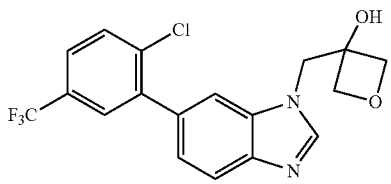 [SMILES: OC1(Cn2cnc3ccc(-c4cc(C(F)(F)F)ccc4Cl)cc32)COC1] | $^1$H-NMR (CDCl$_3$) δ: 4.30 (1H, s), 4.60-4.69 (6H, m), 7.21-7.24 (1H, m), 7.52-7.66 (5H, m), 8.00 (1H, s). |
| 163 | 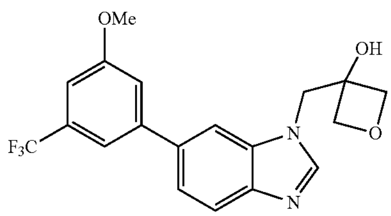 [SMILES: COc1cc(-c2ccc3ncn(CC4(O)COC4)c3c2)cc(C(F)(F)F)c1] | $^1$H-NMR (CDCl$_3$) δ: 3.90-3.91 (4H, m), 4.61-4.68 (6H, m), 7.10 (1H, s), 7.28 (1H, s), 7.39-7.43 (2H, m), 7.67-7.69 (2H, m), 8.00 (1H, s). |
| 164 | 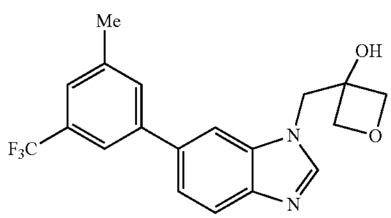 [SMILES: Cc1cc(-c2ccc3ncn(CC4(O)COC4)c3c2)cc(C(F)(F)F)c1] | $^1$H-NMR (CDCl$_3$) δ: 4.19 (1H, s), 4.62-4.69 (6H, m), 7.37-7.41 (2H, m), 7.56-7.68 (4H, m), 7.98 (1H, s). |
| 165 | 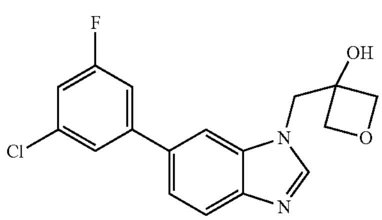 [SMILES: OC1(Cn2cnc3ccc(-c4cc(F)cc(Cl)c4)cc32)COC1] | $^1$H-NMR (CDCl$_3$) δ: 3.79 (1H, s), 4.60-4.66 (6H, m), 7.06 (1H, m), 7.20 (1H, m), 7.36-7.39 (2H, m), 7.67-7.71 (2H, m), 8.01 (1H, s). |
| 166 | 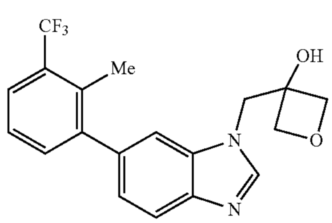 [SMILES: Cc1c(-c2ccc3ncn(CC4(O)COC4)c3c2)cccc1C(F)(F)F] | $^1$H-NMR (CDCl$_3$) δ: 2.30 (3H, d, J = 1.8 Hz), 4.24 (1H, s), 4.57-4.68 (6H, m), 7.11 (1H, dd, J = 8.5, 1.2 Hz), 7.30 (1H, dd, J = 7.9, 7.9 Hz), 7.40 (1H, d, J = 7.3 Hz), 7.43 (1H, d, J = 1.2 Hz), 7.63-7.67 (2H, m), 8.00 (1H, s). |
| 167 | 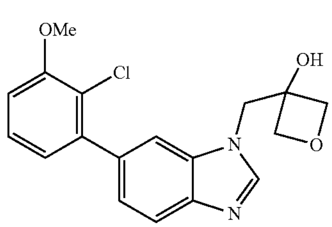 [SMILES: COc1cccc(-c2ccc3ncn(CC4(O)COC4)c3c2)c1Cl] | $^1$H-NMR (CDCl$_3$) δ: 3.94 (3H, s), 4.51 (1H, s), 4.57 (2H, s), 4.65 (4H, dd, J = 21.7, 7.6 Hz), 6.93-6.97 (2H, m), 7.21-7.28 (2H, m), 7.58-7.60 (2H, m), 7.95 (1H, s). |

TABLE 9-continued

| Example | Chemical Structure | Spectrum data |
| --- | --- | --- |
| 168 | (2-chloro-3-(trifluoromethyl)phenyl)-benzimidazole with oxetanyl-methyl | $^1$H-NMR (CDCl$_3$) δ: 3.91 (1H, s), 4.59-4.66 (6H, m), 7.21 (1H, dd, J = 8.2, 1.5 Hz), 7.41 (1H, dd, J = 7.9, 7.9 Hz), 7.53 (1H, dd, J = 7.6, 1.5 Hz), 7.58 (1H, d, J = 1.2 Hz), 7.68-7.73 (2H, m), 8.01 (1H, s). |
| 169 | (3-chloro-5-methylphenyl)-benzimidazole with oxetanyl-methyl | $^1$H-NMR (CDCl$_3$) δ: 2.40 (3H, s), 4.60-4.72 (6H, m), 4.78 (1H, s), 7.15 (1H, s), 7.26 (1H, s), 7.32 (1H, dd, J = 8.5, 1.8 Hz), 7.36 (1H, s), 7.53 (1H, d, J = 7.9 Hz), 7.64 (1H, d, J = 1.2 Hz), 7.92 (1H, s). |
| 170 | (4-fluorophenyl)-benzimidazole with 3-hydroxy-3-methylbutyl | $^1$H-NMR (CDCl$_3$) δ: 1.33 (6H, s), 1.41 (1H, s), 2.04-2.06 (2H, m), 4.35-4.39 (2H, m), 7.12-7.14 (2H, m), 7.44 (1H, dd, J = 8.5, 1.8 Hz), 7.51 (1H, d, J = 1.2 Hz), 7.56-7.59 (2H, m), 7.82 (1H, d, J = 8.5 Hz), 7.93 (1H, s). |
| 171 | (4-chlorophenyl)-benzimidazole with 3-hydroxy-3-methylbutyl | $^1$H-NMR (CDCl$_3$) δ: 1.33 (6H, s), 1.41 (1H, s), 2.04-2.06 (2H, m), 4.35-4.39 (2H, m), 7.40-7.41 (2H, m), 7.45 (1H, dd, J = 8.2, 1.5 Hz), 7.52 (1H, d, J = 1.2 Hz), 7.54-7.56 (2H, m), 7.83 (1H, d, J = 8.5 Hz), 7.93 (1H, s). |
| 172 | (4-(trifluoromethyl)phenyl)-benzimidazole with 3-hydroxy-3-methylbutyl | $^1$H-NMR (CDCl$_3$) δ: 1.34 (6H, s), 1.36 (1H, s), 2.04-2.06 (2H, m), 4.37-4.41 (2H, m), 7.50 (1H, dd, J = 8.5, 1.8 Hz), 7.58 (1H, s), 7.71 (4H, m), 7.86 (1H, d, J = 8.5 Hz), 7.96 (1H, s). |
| 173 | (2-methoxy-4-(trifluoromethyl)phenyl)-benzimidazole with 3-hydroxy-3-methylbutyl | $^1$H-NMR (CDCl$_3$) δ: 1.32 (6H, s), 1.33 (1H, s), 2.02-2.07 (2H, m), 3.86 (3H, s), 4.33-4.37 (2H, m), 7.19 (1H, d, J = 1.2 Hz), 7.30 (1H, dd, J = 8.2, 1.5 Hz), 7.40 (1H, dd, J = 8.2, 1.5 Hz), 7.46 (1H, d, J = 7.9 Hz), 7.53 (1H, d, J = 1.2 Hz), 7.82 (1H, d, J = 7.9 Hz), 7.94 (1H, s). |
| 174 | (2-fluoro-4-(trifluoromethyl)phenyl)-benzimidazole with 3-hydroxy-3-methylbutyl | $^1$H-NMR (CDCl$_3$) δ: 1.33 (6H, s), 2.03-2.07 (2H, m), 4.36-4.40 (2H, m), 7.42-7.50 (3H, m), 7.59-7.64 (2H, m), 7.87 (1H, d, J = 8.5 Hz), 7.97 (1H, s). |

Example 175: Preparation of 1-[5-(4-fluorophenyl)-1H-benzimidazol-1-yl]-2-methylpropan-2-ol (Compound 175)

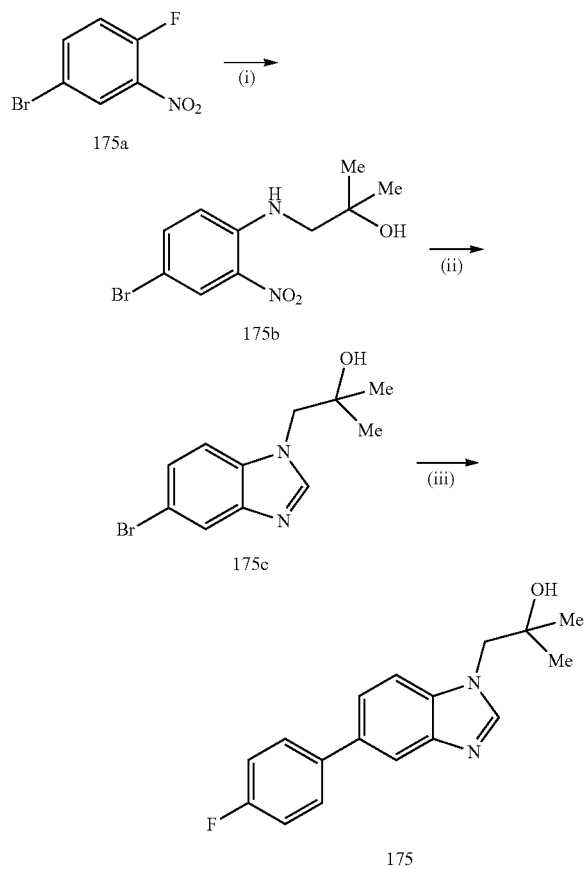

Step (i): Preparation of 1-[(4-bromo-2-nitrophenyl)amino]-2-methylpropan-2-ol (Compound 175b)

Compound 175b (4.81 g) was prepared according to the process of Step (i) in Example 1 by using Compound 175a (5.0 g) instead of Compound 61.

Step (ii): Preparation of 1-(5-bromo-1H-benzimidazol-1-yl)-2-methylpropan-2-ol (Compound 175c)

Compound 175c (3.52 g) was prepared according to the process of Step (ii) in Example 59 by using Compound 175b (4.80 g) instead of Compound 86.

Step (iii): Preparation of 1-[5-(4-fluorophenyl)-1H-benzimidazol-1-yl]-2-methylpropan-2-ol (Compound 175)

Compound 175 (29 mg) was prepared according to the process of Step (iv) in Example 5 by using Compound 175c (50 mg) instead of Compound 69.

$^1$H-NMR (CDCl$_3$) δ: 1.31 (6H, s), 4.19 (2H, s), 7.10-7.13 (2H, m), 7.49 (2H, m), 7.54-7.57 (2H, m), 7.92 (1H, s), 8.23 (1H, s).

Examples 176-223

Examples 176 to 223 shown in the following table were prepared according to the process of Example 175 by using each appropriate starting material.

TABLE 10

| Example | Chemical Structure | Spectrum data |
|---|---|---|
| 176 | 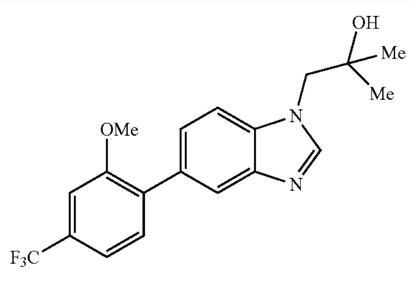 [SMILES: COc1cc(C(F)(F)F)ccc1-c1ccc2c(c1)ncn2CC(C)(C)O] | $^1$H-NMR (CDCl$_3$) δ: 1.32 (6H, s), 3.85 (3H, s), 4.20 (2H, s), 7.18 (1H, s), 7.29 (1H, d, J = 7.3 Hz), 7.44 (1H, d, J = 7.9 Hz), 7.46-7.51 (2H, m), 7.95 (1H, s), 8.28 (1H, s). |
| 177 | 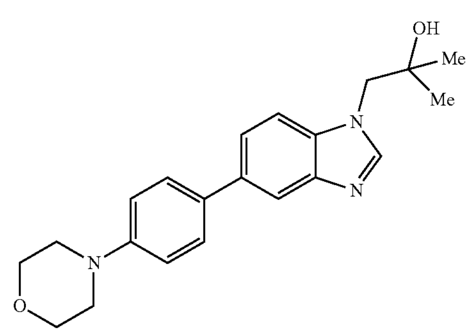 [SMILES: CC(C)(O)Cn1cnc2cc(-c3ccc(N4CCOCC4)cc3)ccc21] | $^1$H-NMR (CDCl$_3$) δ: 1.31 (6H, s), 3.55-3.57 (4H, m), 3.83-3.85 (4H, m), 4.20 (2H, s), 6.73 (1H, d, J = 8.5 Hz), 7.48-7.51 (2H, m), 7.77-7.80 (1H, m), 7.91 (1H, s), 8.28 (1H, s), 8.47 (1H, s). |

TABLE 10-continued

| Example | Chemical Structure | Spectrum data |
| --- | --- | --- |
| 178 | (4-chlorophenyl-benzimidazole with 2-hydroxy-2-methylpropyl) | $^1$H-NMR (CDCl$_3$) δ: 1.31 (6H, s), 4.20 (2H, s), 7.38-7.41 (2H, m), 7.51-7.55 (4H, m), 7.94 (1H, s), 8.28 (1H, s). |
| 179 | (4-trifluoromethoxyphenyl-benzimidazole with 2-hydroxy-2-methylpropyl) | $^1$H-NMR (CDCl$_3$) δ: 1.32 (6H, s), 4.22 (2H, s), 7.28 (2H, m), 7.52 (2H, m), 7.61 (2H, m), 7.96 (1H, d, J = 1.2 Hz), 8.36 (1H, s). |
| 180 | (6-trifluoromethylpyridin-3-yl-benzimidazole with 2-hydroxy-2-methylpropyl) | $^1$H-NMR (CDCl$_3$) δ: 1.32 (6H, s), 4.21 (2H, s), 7.55-7.59 (2H, m), 7.74 (1H, d, J = 7.9 Hz), 8.01 (1H, d, J = 1.2 Hz), 8.06 (1H, dd, J = 8.2, 2.1 Hz), 8.29 (1H, s), 8.96 (1H, d, J = 1.8 Hz). |
| 181 | (2-fluoro-4-trifluoromethylphenyl-benzimidazole with 2-hydroxy-2-methylpropyl) | $^1$H-NMR (CDCl$_3$) δ: 1.32 (6H, s), 4.21 (2H, s), 7.41-7.61 (5H, m), 7.97 (1H, s), 8.31 (1H, s). |
| 182 | (6-methoxypyridin-3-yl-benzimidazole with 2-hydroxy-2-methylpropyl) | $^1$H-NMR (CDCl$_3$) δ: 1.31 (6H, s), 3.97 (3H, s), 4.20 (2H, s), 6.82 (1H, d, J = 8.5 Hz), 7.47-7.52 (2H, m), 7.81 (1H, dd, J = 8.5, 1.8 Hz), 7.91 (1H, s), 8.28 (1H, s), 8.40 (1H, d, J = 2.4 Hz). |
| 183 | (6-methylpyridin-3-yl-benzimidazole with 2-hydroxy-2-methylpropyl) | $^1$H-NMR (CDCl$_3$) δ: 1.27 (6H, s), 2.56 (3H, s), 4.10 (2H, s), 7.17-7.19 (1H, m), 7.41-7.47 (2H, m), 7.76 (1H, dd, J = 8.2, 1.5 Hz), 7.85 (1H, s), 7.98 (1H, s), 8.64 (1H, s). |

TABLE 10-continued

| Example | Chemical Structure | Spectrum data |
| --- | --- | --- |
| 184 | 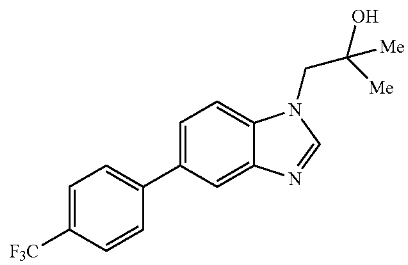 [SMILES: CC(C)(O)Cn1cnc2cc(-c3ccc(C(F)(F)F)cc3)ccc21] | $^1$H-NMR (CDCl$_3$) δ: 1.32 (6H, s), 4.21 (2H, s), 7.55 (2H, m), 7.68-7.71 (4H, m), 8.00 (1H, s), 8.29 (1H, s). |
| 185 | 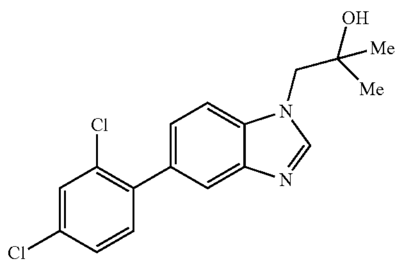 [SMILES: CC(C)(O)Cn1cnc2cc(-c3ccc(Cl)cc3Cl)ccc21] | $^1$H-NMR (CDCl$_3$) δ: 1.32 (6H, s), 1.77 (1H, s), 4.14 (2H, s), 7.29-7.34 (3H, m), 7.47-7.49 (2H, m), 7.80 (1H, d, J = 1.2 Hz), 8.01 (1H, s). |
| 186 | 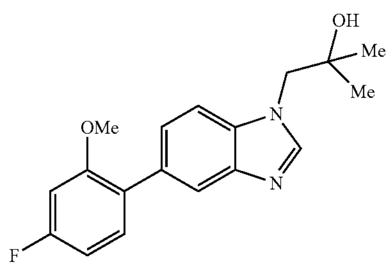 [SMILES: COc1cc(F)ccc1-c1ccc2c(c1)ncn2CC(C)(C)O] | $^1$H-NMR (CDCl$_3$) δ: 1.31 (6H, s), 1.70 (1H, br s), 3.79 (3H, s), 4.13 (2H, s), 6.69-6.75 (2H, m), 7.26-7.31 (1H, m), 7.39-7.46 (2H, m), 7.88 (1H, d, J = 1.2 Hz), 7.97 (1H, s). |
| 187 | 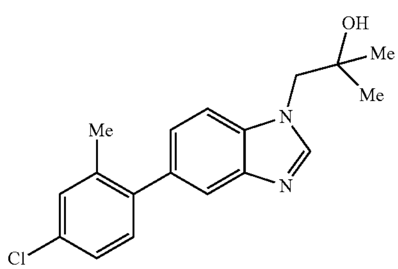 [SMILES: Cc1cc(Cl)ccc1-c1ccc2c(c1)ncn2CC(C)(C)O] | $^1$H-NMR (CDCl$_3$) δ: 1.32 (6H, s), 1.73 (1H, s), 2.24 (3H, s), 4.15 (2H, s), 7.16-7.21 (3H, m), 7.25 (1H, s), 7.46 (1H, d, J = 8.5 Hz), 7.67 (1H, d, J = 1.2 Hz), 8.00 (1H, s). |
| 188 | 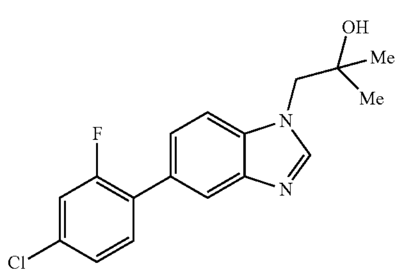 | $^1$H-NMR (CDCl$_3$) δ: 1.31 (6H, s), 1.81 (1H, s), 4.14 (2H, s), 7.17-7.21 (2H, m), 7.38-7.50 (3H, m), 7.89 (1H, s), 8.00 (1H, s). |
| 189 | 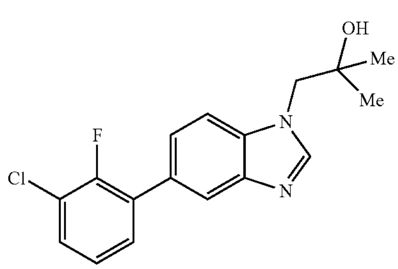 [SMILES: CC(C)(O)Cn1cnc2cc(-c3cccc(Cl)c3F)ccc21] | $^1$H-NMR (CDCl$_3$) δ: 1.32 (6H, s), 1.77 (1H, s), 4.15 (2H, s), 7.11-7.15 (1H, m), 7.33-7.38 (2H, m), 7.44-7.52 (2H, m), 7.91 (1H, s), 8.00 (1H, s). |

TABLE 10-continued
| Example | Chemical Structure | Spectrum data |
|---|---|---|
| 190 | 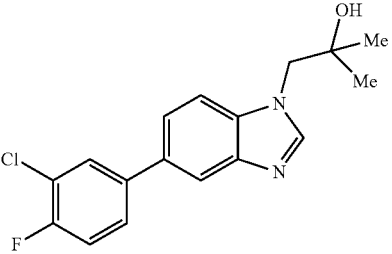 [SMILES: CC(C)(O)Cn1cnc2cc(-c3ccc(F)c(Cl)c3)ccc21] | $^1$H-NMR (CDCl$_3$) δ: 1.31 (6H, s), 1.78 (1H, s), 4.14 (2H, s), 7.19 (1H, m), 7.41-7.50 (3H, m), 7.61 (1H, dd, J = 6.7, 2.4 Hz), 7.88 (1H, d, J = 1.2 Hz), 8.00 (1H, s). |
| 191 | 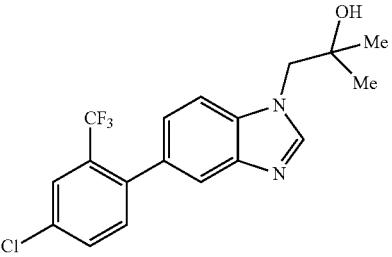 [SMILES: CC(C)(O)Cn1cnc2cc(-c3ccc(Cl)cc3C(F)(F)F)ccc21] | $^1$H-NMR (CDCl$_3$) δ: 1.32 (6H, s), 1.64 (1H, s), 4.14 (2H, s), 7.21 (1H, d, J = 8.2 Hz), 7.31 (1H, d, J = 8.2 Hz), 7.44 (1H, d, J = 8.7 Hz), 7.51 (1H, d, J = 8.2 Hz), 7.71 (2H, m), 8.02 (1H, br s). |
| 192 | 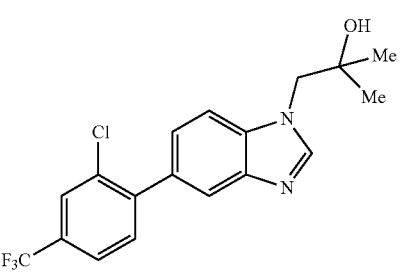 [SMILES: CC(C)(O)Cn1cnc2cc(-c3ccc(C(F)(F)F)cc3Cl)ccc21] | $^1$H-NMR (CDCl$_3$) δ: 1.32 (6H, s), 1.75 (1H, s), 4.15 (2H, s), 7.34-7.38 (1H, m), 7.49-7.58 (3H, m), 7.74 (1H, s), 7.84 (1H, s), 8.03 (1H, s). |
| 193 | 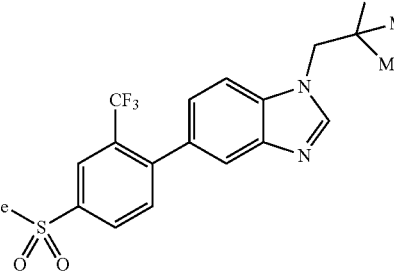 | $^1$H-NMR (CDCl$_3$) δ: 1.33 (6H, s), 1.69 (1H, s), 3.14 (3H, s), 4.16 (2H, s), 7.21-7.26 (1H, m), 7.47-7.53 (1H, m), 7.59-7.64 (1H, m), 7.73-7.76 (1H, m), 8.04-8.15 (2H, m), 8.33 (1H, br s). |
| 194 | 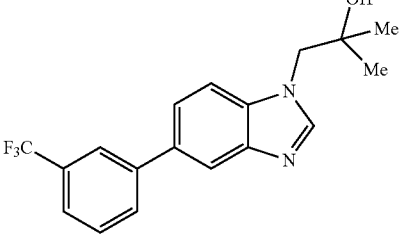 | $^1$H-NMR (CDCl$_3$) δ: 1.32 (6H, s), 1.86 (1H, s), 4.15 (2H, s), 7.51-7.58 (4H, m), 7.78 (1H, d, J = 7.3 Hz), 7.84 (1H, s), 7.95 (1H, s), 8.00 (1H, s). |

TABLE 10-continued

| Example | Chemical Structure | Spectrum data |
|---|---|---|
| 195 | 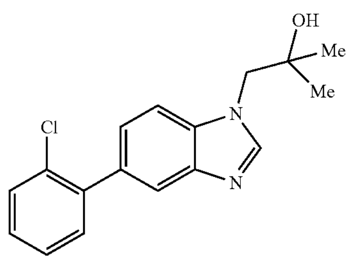 [SMILES: CC(C)(O)Cn1cnc2cc(-c3ccccc3Cl)ccc21] | $^1$H-NMR (CDCl$_3$) δ: 1.33 (6H, s), 1.70 (1H, s), 4.15 (2H, s), 7.25-7.33 (2H, m), 7.37 (1H, s), 7.39 (1H, d, J = 1.8 Hz), 7.46-7.49 (2H, m), 7.84 (1H, d, J = 1.2 Hz), 8.00 (1H, s). |
| 196 | 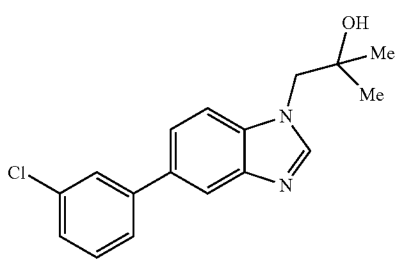 [SMILES: CC(C)(O)Cn1cnc2cc(-c3cccc(Cl)c3)ccc21] | $^1$H-NMR (CDCl$_3$) δ: 1.32 (6H, s), 1.78 (1H, s), 4.14 (2H, s), 7.28 (1H, m), 7.35 (1H, dd, J = 7.9, 7.9 Hz), 7.47-7.51 (3H, m), 7.59 (1H, dd, J = 1.8, 1.8 Hz), 7.93 (1H, s), 7.99 (1H, s). |
| 197 | 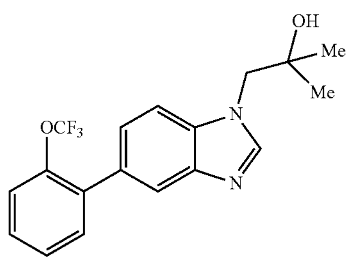 [SMILES: CC(C)(O)Cn1cnc2cc(-c3ccccc3OC(F)(F)F)ccc21] | $^1$H-NMR (CDCl$_3$) δ: 1.32 (6H, s), 1.73 (1H, s), 4.15 (2H, s), 7.34-7.41 (4H, m), 7.45-7.49 (2H, m), 7.86 (1H, d, J = 1.2 Hz), 8.00 (1H, s). |
| 198 | 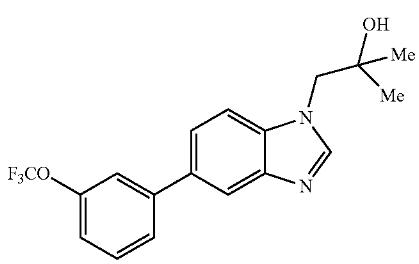 [SMILES: CC(C)(O)Cn1cnc2cc(-c3cccc(OC(F)(F)F)c3)ccc21] | $^1$H-NMR (CDCl$_3$) δ: 1.32 (6H, s), 1.80 (1H, s), 4.15 (2H, s), 7.16 (1H, d, J = 8.5 Hz), 7.42-7.55 (5H, m), 7.94 (1H, s), 8.00 (1H, s). |
| 199 | 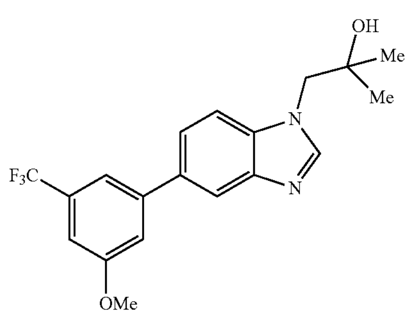 [SMILES: COc1cc(-c2ccc3c(c2)ncn3CC(C)(C)O)cc(C(F)(F)F)c1] | $^1$H-NMR (CDCl$_3$) δ: 1.32 (6H, s), 1.95 (1H, s), 3.89 (3H, s), 4.15 (2H, s), 7.07 (1H, s), 7.28 (1H, s), 7.42 (1H, s), 7.50 (2H, m), 7.92 (1H, s), 8.00 (1H, s). |

TABLE 10-continued

| Example | Chemical Structure | Spectrum data |
|---|---|---|
| 200 | 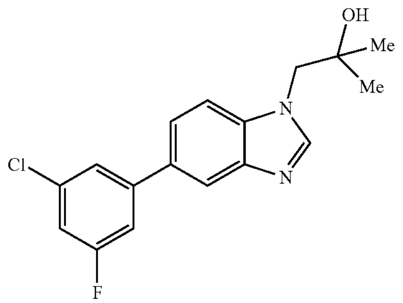 [SMILES: CC(C)(O)Cn1cnc2cc(-c3cc(F)cc(Cl)c3)ccc21] | $^1$H-NMR (CDCl$_3$) δ: 1.32 (6H, s), 1.88 (1H, s), 4.14 (2H, s), 7.03 (1H, m), 7.17-7.21 (1H, m), 7.37 (1H, d, J = 1.8 Hz), 7.44-7.52 (2H, m), 7.89 (1H, d, J = 1.2 Hz), 8.00 (1H, s). |
| 201 | 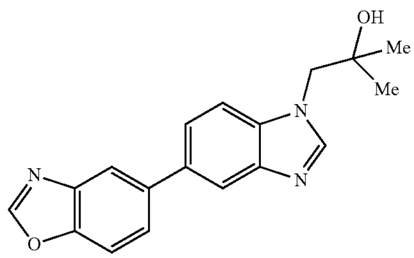 [SMILES: CC(C)(O)Cn1cnc2cc(-c3ccc4ocnc4c3)ccc21] | $^1$H-NMR (DMSO-d6) δ: 1.12 (6H, s), 4.17 (2H, s), 4.80 (1H, s), 7.59 (1H, dd, J = 8.4, 1.6 Hz), 7.73-7.78 (2H, m), 7.83 (1H, d, J = 8.8 Hz), 7.93 (1H, d, J = 1.6 Hz), 8.07 (1H, d, J = 1.6 Hz), 8.15 (1H, s), 8.77 (1H, s). |
| 202 | 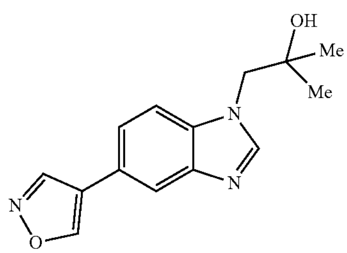 [SMILES: CC(C)(O)Cn1cnc2cc(-c3cnoc3)ccc21] | $^1$H-NMR (DMSO-d6) δ: 1.10 (6H, s), 4.15 (2H, s), 4.78 (1H, s), 7.56 (1H, dd, J = 8.4, 1.2 Hz), 7.71 (1H, d, J = 8.4 Hz), 8.01 (1H, d, J = 1.2 Hz), 8.13 (1H, s), 9.20 (1H, s), 9.41 (1H, s). |
| 203 | 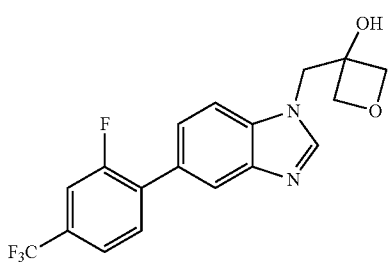 | $^1$H-NMR (DMSO-d6) δ: 4.43 (2H, d, J = 6.8 Hz), 4.55 (2H, d, J = 6.8 Hz), 4.61 (2H, s), 6.26 (1H, s), 7.46-7.49 (1H, m), 7.65-7.68 (1H, m), 7.77-7.86 (4H, m), 8.35 (1H, s). |
| 204 | 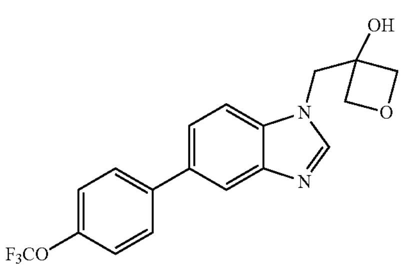 [SMILES: OC1(Cn2cnc3cc(-c4ccc(OC(F)(F)F)cc4)ccc32)COC1] | $^1$H-NMR (DMSO-d6) δ: 4.43 (2H, d, J = 7.2 Hz), 4.54 (2H, d, J = 7.2 Hz), 4.59 (2H, s), 6.25 (1H, s), 7.43 (2H, m), 7.57 (1H, dd, J = 8.4, 2.0 Hz), 7.78 (1H, d, J = 8.4 Hz), 7.81-7.84 (2H, m), 7.92-7.91 (1H, m), 8.30 (1H, s). |
| 205 | 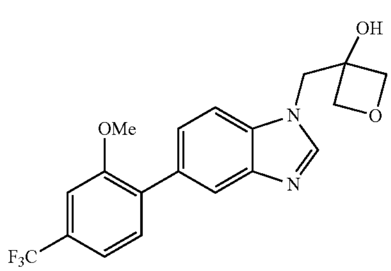 [SMILES: COc1cc(C(F)(F)F)ccc1-c1ccc2c(c1)ncn2CC1(O)COC1] | $^1$H-NMR (CDCl$_3$) δ: 3.84 (3H, s), 4.58-4.65 (6H, m), 7.17 (1H, s), 7.27 (1H, d, J = 7.9 Hz), 7.39 (1H, d, J = 7.3 Hz), 7.45 (1H, dd, J = 8.5, 1.2 Hz), 7.57 (1H, d, J = 8.5 Hz), 7.85 (1H, d, J = 1.8 Hz), 8.00 (1H, s). |

TABLE 10-continued

| Example | Chemical Structure | Spectrum data |
|---|---|---|
| 206 | 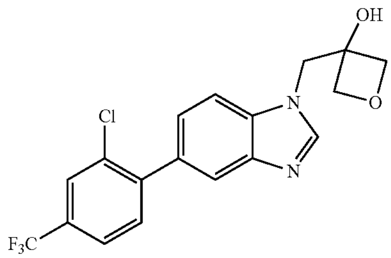 [SMILES: OC1(Cn2cnc3cc(-c4ccc(C(F)(F)F)cc4Cl)ccc32)COC1] | $^1$H-NMR (CDCl$_3$) δ: 4.60-4.66 (6H, m), 7.38 (1H, dd, J = 8.2, 1.5 Hz), 7.46 (1H, d, J = 7.9 Hz), 7.56 (1H, dd, J = 7.9, 1.2 Hz), 7.61 (1H, d, J = 7.9 Hz), 7.74 (1H, d, J = 1.2 Hz), 7.78 (1H, d, J = 1.2 Hz), 8.05 (1H, s). |
| 207 | 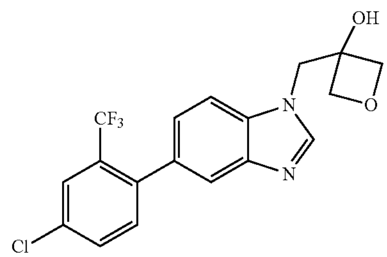 [SMILES: OC1(Cn2cnc3cc(-c4ccc(Cl)cc4C(F)(F)F)ccc32)COC1] | $^1$H-NMR (CDCl$_3$) δ: 4.59-4.65 (6H, m), 7.22-7.27 (2H, m), 7.51 (1H, dd, J = 8.2, 2.1 Hz), 7.55 (1H, d, J = 8.5 Hz), 7.65 (1H, s), 7.72 (1H, d, J = 1.8 Hz), 8.02 (1H, s). |
| 208 | 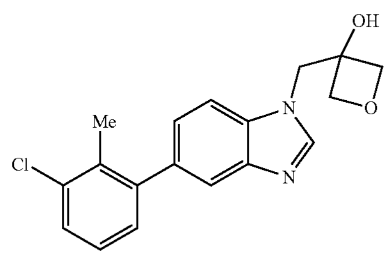 [SMILES: Cc1c(Cl)cccc1-c1ccc2c(c1)ncn2CC1(O)COC1] | $^1$H-NMR (CDCl$_3$) δ: 2.25 (3H, s), 3.65 (1H, br s), 4.60-4.66 (6H, m), 7.09-7.16 (2H, m), 7.21 (1H, dd, J = 8.5, 1.6 Hz), 7.35 (1H, dd, J = 7.8, 1.8 Hz), 7.56 (1H, d, J = 8.2 Hz), 7.61 (1H, d, J = 0.9 Hz), 8.03 (1H, s). |
| 209 | 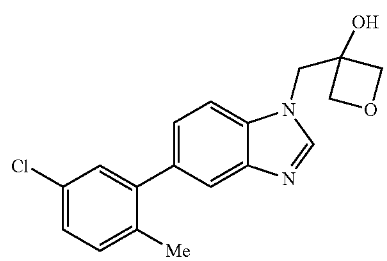 [SMILES: Cc1ccc(Cl)cc1-c1ccc2c(c1)ncn2CC1(O)COC1] | $^1$H-NMR (CDCl$_3$) δ: 2.19 (3H, s), 3.59 (1H, s), 4.59-4.67 (6H, m), 7.16-7.24 (4H, m), 7.56 (1H, d, J = 8.7 Hz), 7.60 (1H, d, J = 0.9 Hz), 8.01 (1H, s). |
| 210 | 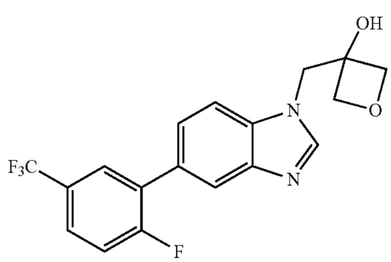 | $^1$H-NMR (CDCl$_3$) δ: 3.37 (1H, d, J = 7.3 Hz), 4.61-4.66 (6H, m), 7.22-7.27 (1H, m), 7.47 (1H, m), 7.54-7.59 (1H, m), 7.62 (1H, d, J = 8.5 Hz), 7.68 (1H, dd, J = 7.3, 1.8 Hz), 7.84 (1H, s), 8.02 (1H, s). |
| 211 | 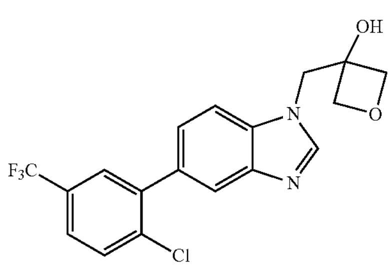 [SMILES: OC1(Cn2cnc3cc(-c4cc(C(F)(F)F)ccc4Cl)ccc32)COC1] | $^1$H-NMR (CDCl$_3$) δ: 3.83 (1H, s), 4.61-4.68 (6H, m), 7.37 (1H, dd, J = 8.5, 1.2 Hz), 7.50-7.62 (4H, m), 7.71 (1H, d, J = 1.8 Hz), 8.02 (1H, s). |

TABLE 10-continued

| Example | Chemical Structure | Spectrum data |
|---|---|---|
| 212 | 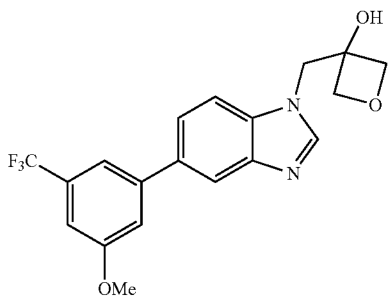 [SMILES: COc1cc(-c2ccc3c(c2)ncn3CC2(O)COC2)cc(C(F)(F)F)c1] | $^1$H-NMR (CDCl$_3$) δ: 3.87 (3H, s), 4.27 (1H, s), 4.60 (2H, s), 4.68 (4H, dd, J = 21.1, 7.6 Hz), 7.05 (1H, s), 7.17 (1H, s), 7.30 (1H, s), 7.46 (1H, dd, J = 8.5, 1.8 Hz), 7.59 (1H, d, J = 8.5 Hz), 7.68 (1H, d, J = 1.2 Hz), 7.94 (1H, s). |
| 213 | 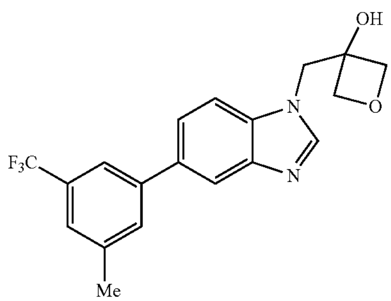 [SMILES: Cc1cc(-c2ccc3c(c2)ncn3CC2(O)COC2)cc(C(F)(F)F)c1] | $^1$H-NMR (CDCl$_3$) δ: 4.46 (1H, s), 4.60 (2H, s), 4.69 (4H, dd, J = 23.5, 7.5 Hz), 7.35 (1H, s), 7.43-7.49 (3H, m), 7.58 (1H, d, J = 8.7 Hz), 7.64 (1H, s), 7.92 (1H, s). |
| 214 | 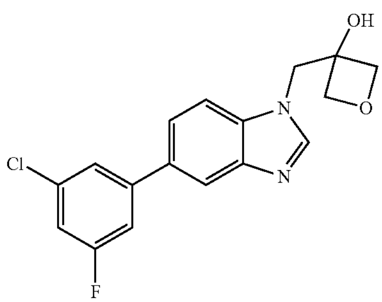 [SMILES: OC1(Cn2cnc3cc(-c4cc(F)cc(Cl)c4)ccc32)COC1] | $^1$H-NMR (CDCl$_3$) δ: 3.45 (1H, s), 4.59-4.67 (6H, m), 7.03 (1H, m), 7.14 (1H, m), 7.32 (1H, s), 7.45 (1H, dd, J = 8.5, 1.6 Hz), 7.59 (1H, d, J = 8.7 Hz), 7.78 (1H, s), 7.99 (1H, s). |
| 215 | 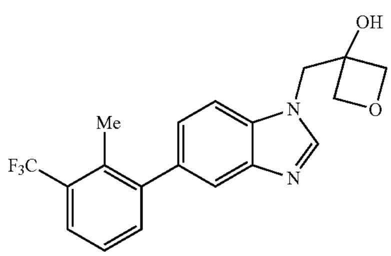 [SMILES: Cc1c(-c2ccc3c(c2)ncn3CC2(O)COC2)cccc1C(F)(F)F] | $^1$H-NMR (CDCl$_3$) δ: 2.30 (3H, d, J = 1.2 Hz), 3.80 (1H, s), 4.61-4.67 (6H, m), 7.20 (1H, dd, J = 8.2, 1.5 Hz), 7.29 (1H, dd, J = 7.6, 7.6 Hz), 7.36 (1H, d, J = 6.7 Hz), 7.56-7.64 (3H, m), 8.03 (1H, s). |
| 216 | 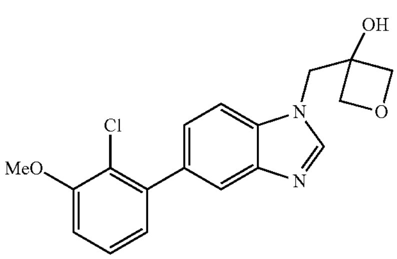 [SMILES: COc1cccc(-c2ccc3c(c2)ncn3CC2(O)COC2)c1Cl] | $^1$H-NMR (CDCl$_3$) δ: 3.27 (1H, s), 3.94 (3H, s), 4.60-4.65 (6H, m), 6.95 (2H, m), 7.24-7.28 (1H, m), 7.39 (1H, dd, J = 8.2, 1.5 Hz), 7.57 (1H, d, J = 8.5 Hz), 7.78 (1H, d, J = 1.8 Hz), 8.01 (1H, s). |

TABLE 10-continued
| Example | Chemical Structure | Spectrum data |
|---|---|---|
| 217 | 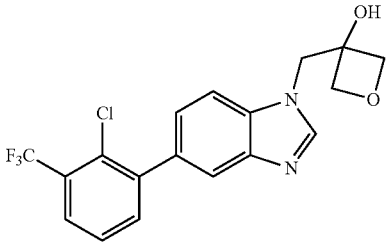 [SMILES: OC1(Cn2cnc3cc(-c4cccc(C(F)(F)F)c4Cl)ccc32)COC1] | ¹H-NMR (CDCl₃) δ: 3.23 (1H, br s), 4.61-4.64 (7H, m), 7.35 (1H, dd, J = 8.2, 1.5 Hz), 7.40 (1H, m), 7.52 (1H, dd, J = 7.9, 1.2 Hz), 7.60 (1H, d, J = 8.5 Hz), 7.70 (1H, dd, J = 7.9, 1.8 Hz), 7.75 (1H, d, J = 1.2 Hz), 8.05 (1H, s). |
| 218 | 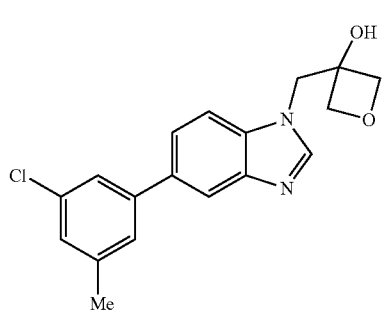 [SMILES: Cc1cc(Cl)cc(-c2ccc3c(c2)ncn3CC2(O)COC2)c1] | ¹H-NMR (CDCl₃) δ: 2.36 (3H, s), 4.56-4.73 (6H, m), 7.13 (2H, m), 7.23-7.25 (1H, m), 7.41 (1H, dd, J = 8.2, 1.5 Hz), 7.55 (1H, d, J = 8.5 Hz), 7.61 (1H, d, J = 1.8 Hz), 7.89 (1H, s). |
| 219 | 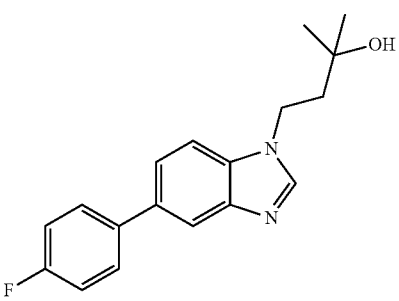 [SMILES: CC(C)(O)CCn1cnc2cc(-c3ccc(F)cc3)ccc21] | ¹H-NMR (CDCl₃) δ: 1.34 (6H, s), 1.37 (1H, s), 2.03-2.08 (2H, m), 4.34-4.38 (2H, m), 7.11-7.13 (2H, m), 7.44-7.50 (2H, m), 7.56-7.58 (2H, m), 7.93 (2H, s). |
| 220 | 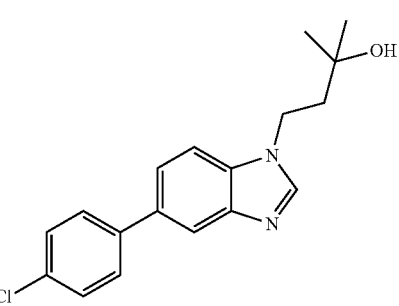 | ¹H-NMR (CDCl₃) δ: 1.33 (6H, s), 1.35 (1H, s), 2.04-2.06 (2H, m), 4.34-4.38 (2H, m), 7.39-7.41 (2H, m), 7.44-7.50 (2H, m), 7.53-7.57 (2H, m), 7.94 (1H, s), 7.95 (1H, s). |
| 221 | 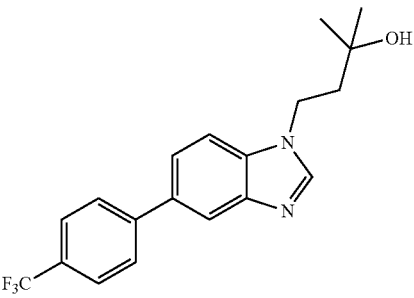 [SMILES: CC(C)(O)CCn1cnc2cc(-c3ccc(C(F)(F)F)cc3)ccc21] | ¹H-NMR (CDCl₃) δ: 1.34 (6H, s), 1.38 (1H, s), 2.04-2.08 (2H, m), 4.35-4.39 (2H, m), 7.48-7.55 (2H, m), 7.67-7.74 (4H, m), 7.96 (1H, s), 8.01 (1H, d, J = 1.2 Hz). |

TABLE 10-continued

| Example | Chemical Structure | Spectrum data |
|---|---|---|
| 222 | (benzimidazole with 2-OMe, 4-CF3 phenyl substituent and 3-hydroxy-3-methylbutyl on N) | $^1$H-NMR (CDCl$_3$) δ: 1.34 (6H, s), 2.04-2.08 (2H, m), 3.85 (3H, s), 4.34-4.38 (2H, m), 7.18 (1H, s), 7.29 (1H, d, J = 7.9 Hz), 7.45-7.46 (3H, m), 7.94 (2H, s). |
| 223 | (benzimidazole with 2-F, 4-CF3 phenyl substituent and 3-hydroxy-3-methylbutyl on N) | $^1$H-NMR (CDCl$_3$) δ: 1.34 (6H, s), 2.04-2.08 (2H, m), 4.36-4.40 (2H, m), 7.42-7.48 (4H, m), 7.59-7.61 (1H, m), 7.96-7.97 (2H, m). |

Example 224: Preparation of 1-{5-[2-fluoro-4-(trifluoromethyl)phenoxy]-1H-benzimidazol-1-yl}-2-methylpropan-2-ol

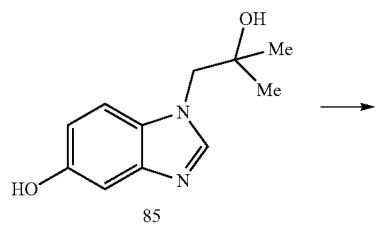

85

→

-continued

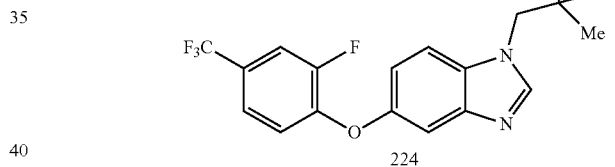

224

Compound 224 (13 mg) was prepared according to the process of Step (v) in Example 13 by using Compound 85 (50 mg).

LCMS: T=0.743, m/z=369

Examples 225 and 226

Examples 225 and 226 shown in the following table were prepared according to the process of Example 224 by using each appropriate starting material.

TABLE 11

| Example | Chemical Structure | Spectrum data |
|---|---|---|
| 225 | (4-CF3-phenoxy benzimidazole with 2-hydroxy-2-methylpropyl on N) | $^1$H-NMR (DMSO-d6) δ: 1.11 (6H, s), 4.16 (2H, s), 4.79 (1H, s), 7.03-7.07 (3H, m), 7.39 (1H, d, J = 2.4 Hz), 7.68 (2H, m), 7.73 (1H, d, J = 8.4 Hz), 8.17 (1H, s). |

| Example | Chemical Structure | Spectrum data |
|---|---|---|
| 226 | ![structure] | ¹H-NMR (DMSO-d6) δ: 4.43 (2H, d, J = 7.2 Hz), 4.54 (2H, d, J = 7.2 Hz), 4.58 (2H, s), 6.25 (1H, s), 7.05-7.07 (3H, m), 7.40 (1H, d, J = 2.8 Hz), 7.68 (1H, d, J = 9.2 Hz), 7.76 (1H, d, J = 9.2 Hz), 8.32 (1H, s). |

Example 227: Preparation of (2R)-2-methyl-3-(6-{[5-(trifluoromethyl)pyridin-2-yl]oxy}-1H-benzimidazol-1-yl)propane-1,2-diol

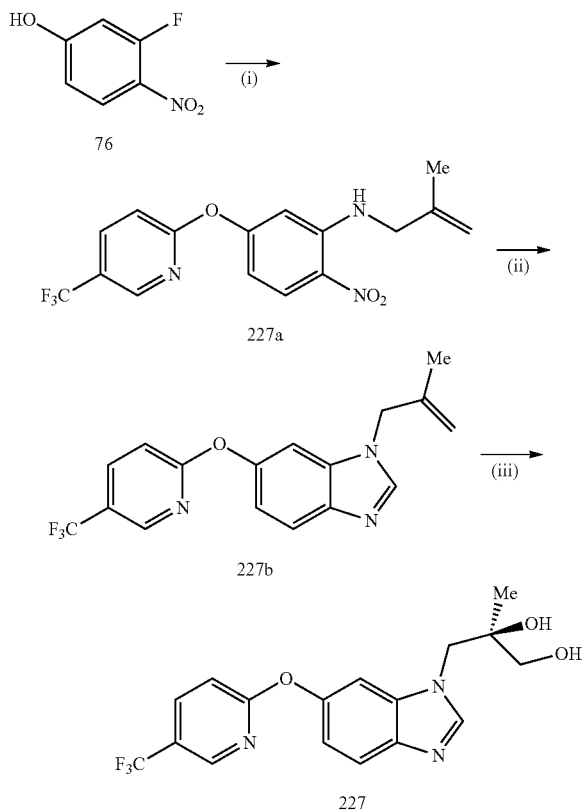

Step (i): Preparation of N-(2-methylprop-2-en-1-yl)-2-nitro-5-{[5-(trifluoromethyl)pyridin-2-yl]oxy}aniline (Compound 227a)

Compound 227a (1.64 g) was prepared according to the process of Step (i) in Example 59 by using the appropriate starting material.

Step (ii): Preparation of 1-(2-methylprop-2-en-1-yl)-6-{[5-(trifluoromethyl)pyridin-2-yl]oxy}-1H-benzimidazole (Compound 227b)

Compound 227b (1.25 g) was prepared according to the process of Step (ii) in Example 59 by using Compound 227a.

Step (iii): Preparation of (2R)-2-methyl-3-(6-{[5-(trifluoromethyl)pyridin-2-yl]oxy}-1H-benzimidazol-1-yl)propane-1,2-diol (Compound 198)

Under a nitrogen atmosphere, water (1 mL), AD-mix-β (200 mg) and methanesulfonamide (14 mg) were added to a solution of Compound 227b (50 mg) in tert-butanol (1 mL), and the reaction mixture was stirred at room temperature for 5 hours. The reaction mixture was directly purified by amino silica gel column chromatography (eluate: chloroform/methanol=95/5) to give Compound 227 (26 mg).

LCMS: T=0.537, m/z=368

Example 228: Preparation of (3R)-2-methyl-3-(6-{[5-(trifluoromethyl)pyridin-2-yl]oxy}-1H-benzimidazol-1-yl) butan-2-ol

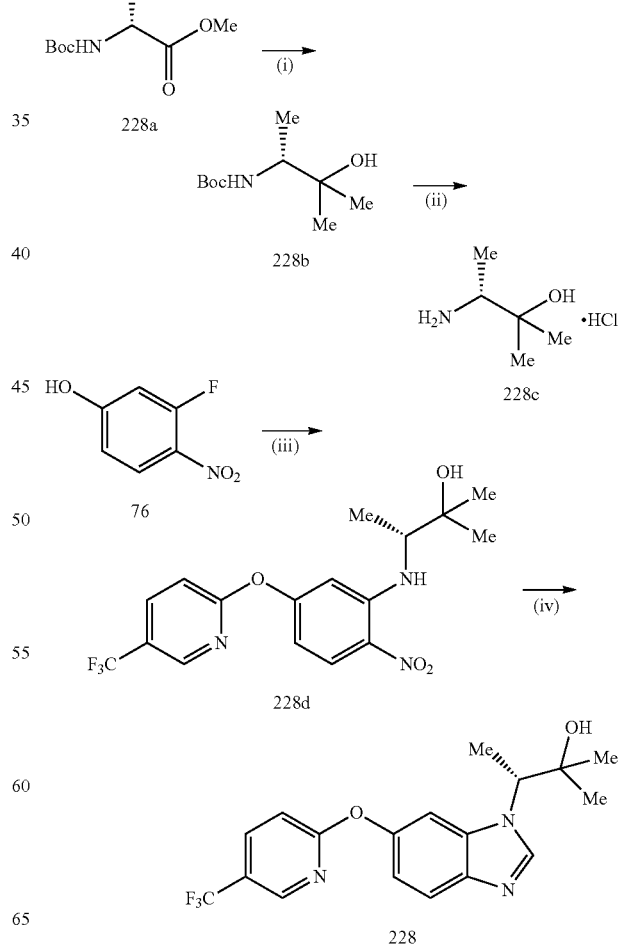

Step (i): Preparation of tert-butyl [(2R)-3-hydroxy-3-methylbutan-2-yl]carbamate (Compound 228b)

Under a nitrogen atmosphere, 3 mol/L methylmagnesium bromide/diethyl ether (5.90 mL) was added to a solution of Boc-D-alanine methyl ester (1.0 g) in diethyl ether (25 mL) at 0° C., and the mixture was stirred at room temperature for 3 hours. The reaction mixture was quenched with aqueous ammonium chloride and then extracted with ethyl acetate, and the organic layer was dried over anhydrous sodium sulfate. The concentrated residue was purified by silica gel column chromatography (eluate: hexane/ethyl acetate=70/30) to give Compound 228b (0.86 g).

Step (ii): Preparation of (3R)-3-amino-2-methylbutan-2-ol monohydrochloride (Compound 228c)

Under a nitrogen atmosphere, 4 mol/L hydrocholic acid/ethyl acetate was added to a solution of Compound 228b (0.86 g) in ethyl acetate (5 mL), and the mixture was stirred at room temperature for 2 hours. The solvent in reaction mixture was removed by azeotropy with toluene, and the obtained residue was slurry-washed with ethyl acetate to give Compound 228c (0.54 g).

Step (iii): Preparation of (3R)-2-methyl-3-[(2-nitro-5-{[5-(trifluoromethyl)pyridin-2-yl]oxy}phenyl) amino]butan-2-ol (Compound 228d)

Compound 228d (490 mg) was prepared according to the process of Step (i) in Example 59 by using Compound 76 (200 mg) and Compound 228c (213 mg).

Step (iv): Preparation of (3R)-2-methyl-3-(6-{[5-(trifluoromethyl)pyridin-2-yl]oxy}-1H-benzimidazol-1-yl)butan-2-ol (Compound 228)

Compound 228 (102 mg) was prepared according to the process of Step (ii) in Example 59 by using Compound 228d (490 mg).
$^{1}$H-NMR (CDCl$_3$) δ: 1.15 (3H, s), 1.33 (3H, s), 1.64 (3H, d, J=7.3 Hz), 1.73 (1H, s), 4.27 (1H, q, J=7.1 Hz), 7.00 (1H, d, J=9.2 Hz), 7.03 (1H, dd, J=8.9, 2.1 Hz), 7.25 (1H, d, J=2.4 Hz), 7.78 (1H, d, J=8.5 Hz), 7.88 (1H, dd, J=8.5, 2.4 Hz), 8.11 (1H, s), 8.41 (1H, d, J=2.4 Hz).

Example 229

Example 229 shown in the following table was prepared according to the process of Example 228 by using the appropriate starting material.

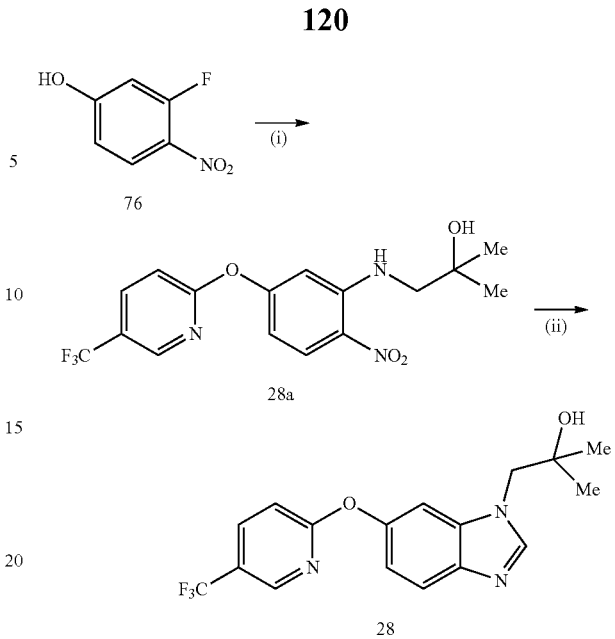

Example 28

2-Methyl-1-(6-{[5-(trifluoromethyl)pyridin-2-yl]oxy}-1H-benzimidazol-1-yl)propan-2-ol (Compound 28) can be prepared in the following manner.

Step (i): Preparation of 2-methyl-1-[(2-nitro-5-{[5-(trifluoromethyl)pyridin-2-yl]oxy}phenyl)amino]propan-2-ol (Compound 28a)

To a solution of Compound 76 (1.00 g) in NMP (16 mL) at room temperature was added diisopropylethylamine (2.06 g). To the mixture was added 1-amino-2-methylpropan-2-ol (0.74 g), and the reaction mixture was heated to 100° C. and stirred for 4 hours. The reaction solution was cooled to room temperature, and cesium carbonate (3.11 g) and 2-fluoro-5-(trifluoromethyl)pyridine (1.37 g) were added thereto. The reaction mixture was heated to 100° C. and stirred for 3 hours. The reaction solution was cooled to room temperature, and ethyl acetate, hexane and water were added thereto. And, the objective product was extracted in the organic layer. The organic layer was washed with water, and dried over anhydrous sodium sulfate. The organic layer was concentrated under reduced pressure, and the obtained residue was slurry-washed (eluate: hexane/ethyl acetate=9/1) to give Compound 28a (1.53 g).

Step (ii): Preparation of 2-methyl-1-(6-{[5-(trifluoromethyl)pyridin-2-yl]oxy}-1H-benzimidazol-1-yl)propan-2-ol (Compound 28)

To a solution of Compound 28a (0.50 g) in methanol (6.7 mL) were added trimethyl orthoformate (3.7 mL), formic

TABLE 12

| Example | Chemical Structure | Spectrum data |
|---------|-------------------|---------------|
| 229 | (structure) | $^{1}$H-NMR (CDCl$_3$) δ: 1.14 (3H, s), 1.33 (3H, s), 1.64 (3H, d, J = 7.3 Hz), 1.82 (1H, s), 4.27 (1H, q, J = 7.2 Hz), 6.99 (1H, d, J = 8.7 Hz), 7.02 (1H, dd, J = 8.7, 2.3 Hz), 7.25 (1H, d, J = 2.3 Hz), 7.77 (1H, d, J = 8.7 Hz), 7.88 (1H, dd, J = 8.7, 2.7 Hz), 8.10 (1H, s), 8.41 (1H, s). | acid (0.52 mL) and zinc (0.44 g), and the mixture was stirred heating at 70° C. for 2 hours. The reaction mixture was filtered through Celite, and the filtrate was concentrated under reduced pressure. The obtained residue was dissolved in ethyl acetate, washed with a water solution of Rochelle salt and brine, and dried over anhydrous sodium sulfate. The concentrated crude crystal was purified by recrystallization from hexane/ethyl acetate (=1:5) to give Compound 28 (0.33 g).

Pharmacological Test

Measurement of Na Ion Current in Voltage-Dependent Na Channel Gene Expressed Cell Nav 1.7 current was measured by automated patch clamp assay using cells stably-expressing human SCN9A.

Cells Stably-expressing Human SCN9A

Tetracycline-induced cells stably-expressing SCN9A were obtained from ChanTest Corporation. The cells were passaged in Ham's F-12 medium containing 10% fetal bovine serum, 100 units/mL Penicillin-Streptomycin, 0.01 mg/mL Blasticidin, and 0.4 mg/mL Zeocin. The day before the measurement, the medium was replaced with Ham's F-12 medium containing 1 µg/mL tetracycline, 100 µmol/L sodium butyrate, 10% fetal bovine serum, and 100 units/mL Penicillin-Streptomycin. Next day, the Na ion current was measured by automated patch clamp assay.

Electrophysiologic Measurement of Na Ion Current

The Na ion current was measured by automated patch clamp assay using the following extracellular solution and intracellular solution.

Extracellular solution (mmol/L): NaCl 130, $MgCl_2$ 2, $CaCl_2$ 2, $CdCl_2$ 0.1, $NiCl_2$ 0.1, Tetraethylammonium-Cl 18, 4-aminopyridine 1, HEPES 10, (adjusting pH 7.4 with NaOH)

Intracellular solution (mmol/L): CsF 120, EGTA 10, NaCl 15, HEPES 10, (adjusting pH 7.2 with CsOH)

The control of the stimulating pulse and the data acquisition were carried out using EPC10 amplifier and Patch Master Software (HEKA). Data were sampled at 10 kHz, and low-pass filtered at 3 kHz. All the measurements were carried out at room temperature. The holding potential was set at a potential inactivating 50% Nav 1.7 channel (around −60 mV), and depolarizing pulse of 20 milliseconds (+10 mV) was given once. The inhibitory rate of the test compounds was calculated based on the results of cells whose peak current was 500 pA or more when the depolarizing pulse was given and whose whole-cell parameter did not greatly vary until the end of the data acquisition. The inhibitory rate of the Na ion current by the test compounds was calculated according to the following calculating formula with the peak current value generated by the depolarizing pulse.

Inhibitory rate of Na ion current (%)=100×[(Peak current value in the absence of Test Compound)−(Peak current value in the presence of Test Compound)]/(Peak current value in the absence of Test Compound)

Result:

The inhibitory rate of Na ion current by each Example Compound was evaluated. The results showed that the compounds of the present invention exhibit the inhibitory effect for Nav 1.7. The inhibitory rate (%) wherein the concentration of each compound is 10 µmol/L is shown in the following table.

TABLE 13

| Example | Inhibitory rate (%) | Example | Inhibitory rate (%) | Example | Inhibitory rate (%) | Example | Inhibitory rate (%) |
|---|---|---|---|---|---|---|---|
| 1 | 83 | 2 | 85 | 3 | 65 | 4 | 52 |
| 5 | 39 | 6 | 41 | 7 | 67 | 8 | 32 |
| 9 | 77 | 10 | 52 | 11 | 75 | 12 | 58 |
| 13 | 25 | 14 | 68 | 15 | 57 | 16 | 67 |
| 17 | 31 | 18 | 41 | 19 | 39 | 20 | 91 |
| 21 | 12 | 22 | 73 | 23 | 47 | 24 | 56 |
| 25 | 72 | 26 | 39 | 27 | 31 | 28 | 82 |
| 29✕ | 16 | 30 | 42 | 31 | 21 | 32 | 35 |
| 33 | 41 | 34 | 20 | 35 | 39 | 36 | 42 |
| 37 | 44 | 38 | 43 | 39 | 46 | 40 | 42 |
| 41 | 29 | 42 | 31 | 43 | 20 | 44 | 26 |
| 45 | 42 | 46 | 33 | 47 | 38 | 48 | 17 |
| 49✕ | 23 | 50 | 25 | 51 | 44 | 52 | 46 |
| 53 | 69 | 54 | 62 | 55 | 37 | 56 | 45 |
| 57 | 47 | 58 | 48 | 59 | 49 | 60 | 52 |
| 90 | 15 | 91 | 24 | 92 | 16 | 93 | 42 |
| 94 | 73 | 95✕ | 66 | 96✕ | 32 | 97 | 83 |
| 98 | 25 | 99 | 12 | 100 | 10 | 101 | 43 |
| 102 | 59 | 103 | 10 | 104 | 57 | 105 | 38 |
| 106 | 50 | 107 | 51 | 108 | 57 | 109 | 30 |
| 110 | 58 | 111 | 52 | 112 | 39 | 113 | 68 |
| 114 | 26 | 115 | 31 | 116 | 33 | 117✕ | 44 |
| 118 | 33 | 119 | 36 | 120 | 13 | 121 | 21 |
| 122 | 14 | 123 | 64 | 124 | 61 | 125 | 13 |
| 126✕ | 7 | 127✕ | 16 | 128 | 24 | 129 | 51 |
| 130 | 48 | 131 | 62 | 132 | 65 | 133 | 60 |
| 134 | 50 | 135 | 29 | 136 | 70 | 137 | 38 |
| 138 | 34 | 139 | 35 | 140 | 24 | 141 | 53 |
| 142 | 55 | 143 | 35 | 144 | 19 | 145 | 15 |
| 146 | 17 | 147 | 15 | 148 | 59 | 149 | 34 |
| 150 | 47 | 151 | 44 | 152 | 38 | 153 | 25 |
| 154 | 52 | 155 | 55 | 156 | 54 | 157 | 51 |
| 158 | 53 | 159 | 45 | 160 | 25 | 161 | 49 |
| 162 | 63 | 163 | 47 | 164 | 63 | 165 | 35 |
| 166 | 54 | 167 | 71 | 168 | 77 | 169 | 46 |
| 170 | 32 | 171 | 60 | 172 | 64 | 173 | 80 |

TABLE 13-continued

| Example | Inhibitory rate (%) | Example | Inhibitory rate (%) | Example | Inhibitory rate (%) | Example | Inhibitory rate (%) |
|---|---|---|---|---|---|---|---|
| 174 | 66 | 175 | 16 | 176 | 73 | 177 | 54 |
| 178 | 34 | 179 | 61 | 180 | 33 | 181 | 45 |
| 182* | 11 | 183* | 30 | 184 | 67 | 185 | 45 |
| 186 | 22 | 187 | 45 | 188 | 51 | 189 | 42 |
| 190 | 42 | 191 | 52 | 192 | 78 | 193 | 23 |
| 194 | 43 | 195 | 31 | 196 | 49 | 197 | 33 |
| 198 | 58 | 199 | 84 | 200 | 52 | 201 | 32 |
| 202 | 21 | 203 | 26 | 204 | 28 | 205 | 46 |
| 206 | 69 | 207 | 65 | 208 | 43 | 209 | 48 |
| 210 | 48 | 211 | 44 | 212 | 55 | 213 | 41 |
| 214 | 42 | 215 | 84 | 216 | 53 | 217 | 60 |
| 218 | 53 | 219 | 40 | 220 | 52 | 221 | 45 |
| 222 | 45 | 223 | 47 | 224 | 53 | 225 | 64 |
| 226 | 45 | 227 | 11 | 228* | 66 | 229 | 32 |

* The results of inhibitory rate in Examples 29, 49, 95, 96, 117, 126, 127, 182, 183, and 228 show inhibitory rate (%) wherein the concentration of each compound is 100 μmol/L.

Test (2)
Evaluation of Analgesic Effect in Streptozotocin-Induced Diabetic Peripheral Neuropathy Models Using some typical compounds among the compounds of the present invention, the inhibitory effect for neuropathic pain was determined through the evaluation of analgesic effect in rats streptozotocin (STZ)-induced diabetic peripheral neuropathy model.

The disease animal model was prepared by means of a partially-modified method of *Fox* et al. (Pain 81, 307-316, 1999). STZ was intraperitoneally administered to 9-week old male Wistar rats in 45 mg/kg of body weight to prepare animal model suffering from diabetic peripheral neuropathy. The analgesic effect was evaluated by von Frey test. Specifically, mechanical sensitivity was measured by applying hairs (von Frey hair) to the plantar surface of the animal's hind paw, and then the reaction thresholds (50% paw withdrawal thresholds) for the mechanical stimulation was determined by using a formula based on *Chaplan* et al. (Journal of Neuroscience Methods 53, 55-63, 1994).

It was already confirmed in a preliminary study that the reaction thresholds of the animal's hind paw markedly decreased on the 21st day or later after administering STZ, hence the evaluation of the analgesic effect using the test compounds was done on any one day between the 21st day and the 30th day after administering STZ. One and two days before evaluating the test compounds, the reaction thresholds were measured to obtain an average thereof, and the average value was used as a reference value obtained before the test compounds would be administered.

In order to reduce the variations of the averaged values among the test groups and the measured values in each group, the animals were divided into 4 to 5 groups.

In the evaluation test of the test compounds, the reaction thresholds were measured after administering each test compound. One hour before measuring the reaction thresholds, each test compound was administered in 3 mg/kg of body weight. The strength of analgesic effect of each test compound is expressed as the extension width (g) of reaction thresholds which is obtained by the calculation formula of (reaction threshold obtained after administering test compound)−(reaction threshold obtained before administering test compound).

Result:
As shown in the following table, the extension widths of reaction thresholds in each compound of the present invention were 1.3 to 6.5 g. Each number in [ ] shows extension widths in the solvent-administration groups for each test.

TABLE 14

| Example | extension width (g) |
|---|---|
| 1 | 2.8 [1.8] |
| 20 | 2.9 [0.9] |
| 28 | 6 [1.9] |
| 59 | 5.1 [0.9] |
| 94 | 4.9 [0.7] |
| 101 | 1.4 [0] |
| 118 | 3.4 [0.4] |
| 123 | 1.3 [0] |
| 148 | 3.7 [0.4] |
| 179 | 6.5 [1.4] |
| 181 | 2.5 [1.4] |
| 205 | 1.6 [0.6] |
| 229 | 3.9 [0.6] |

The above result indicated that the compounds of the present invention exhibit good analgesic effects when the compounds are orally administered to rat models of diabetic peripheral neuropathy.

INDUSTRIAL APPLICABILITY

The compounds of the present invention can be used as a useful medicament for treating a disease involving Nav 1.7, for example, neuropathic pain, nociceptive pain, inflammatory pain, small-fiber neuropathy, erythromelalgia, paroxysmal extreme pain disorder, dysuria, and multiple sclerosis. Thus, The compounds of the present invention can be very useful pharmaceuticals.

The invention claimed is:
1. A compound of formula (I):

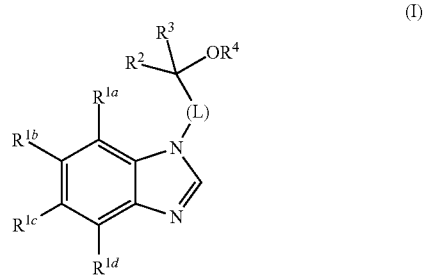

or a pharmaceutically acceptable salt thereof, wherein
$R^{1a}$, $R^{1b}$, $R^{1c}$, and $R^{1d}$ are each independently hydrogen, halogen, cyano, $C_{1-4}$ alkyl, $C_{1-4}$ alkoxy, $C_{1-4}$ alkylamino, $C_{3-7}$ cycloalkyl, $C_{3-7}$ cycloalkoxy, $C_{3-7}$ cycloalkylamino, $C_{6-10}$ aryl, $C_{6-10}$ aryloxy, 5- to 12-membered heteroaryl, or 5- to 12-membered heteroaryloxy;
 wherein each alkyl moiety of the alkyl, alkoxy and alkylamino of $R^{1a}$, $R^{1b}$, $R^{1c}$, and $R^{1d}$ is optionally substituted with 1 to 5 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally-substituted with 1 to 3 substituents independently selected from Substituent-group B;
 each cycloalkyl moiety of the cycloalkyl, the cycloalkoxy, and the cycloalkylamino of $R^{1a}$, $R^{1b}$, $R^{1c}$, and $R^{1d}$ is optionally substituted with 1 to 5 substituents independently selected from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B); and
 each aryl moiety of the aryl and the aryloxy and each heteroaryl moiety of the heteroaryl and the heteroaryloxy of $R^{1a}$, $R^{1b}$, $R^{1c}$, and $R^{1d}$ is optionally substituted with 1 to 5 substituents independently selected from the group consisting of halogen, cyano, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, 3- to 7-membered non-aromatic heterocyclyl optionally-substituted with 1 to 3 substituents selected independently from Substituent-group B, $C_{1-4}$ alkylthio optionally-substituted with 1 to 3 substituents selected independently from Substituent-group A, and $C_{1-4}$ alkylsulfonyl optionally-substituted with 1 to 3 substituents selected independently from Substituent-group A;
 provided that at least one of $R^{1a}$, $R^{1b}$, $R^{1c}$ and $R^{1d}$ is $C_{6-10}$ aryl, $C_{6-10}$ aryloxy, 5- to 12-membered heteroaryl or 5- to 12-membered heteroaryloxy;
$R^2$ and $R^3$ are each independently hydrogen, $C_{1-6}$ alkyl which is optionally substituted with 1 to 5 substituents independently selected from the group consisting of cyano, halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, and $C_{3-7}$ cycloalkoxy optionally-substituted with 1 to 3 substituents selected independently from Substituent-group B, or $C_{3-10}$ cycloalkyl;
$R^4$ is hydrogen, $C_{1-6}$ alkyl which is optionally substituted with 1 to 3 substituents independently selected from the group consisting of halogen, hydroxyl, $C_{1-4}$alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally-substituted with 1 to 3 substituents independently selected from Substituent-group B, or $C_{3-7}$ cycloalkyl which optionally substituted with 1 to 3 substituents independently selected from the group consisting of halogen, hydroxyl, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, and $C_{3-7}$ cycloalkoxy optionally-substituted with 1 to 3 substituents independently selected from Substituent-group B;
m is 1, 2 or 3;
L is $CR^7R^8$, provided that when m is 2 or 3, each $CR^7R^8$ are independently the same or different;
$R^7$ and $R^8$ are each independently hydrogen, hydroxyl, $C_{1-4}$ alkyl, $C_{1-4}$ alkoxy, $C_{3-7}$ cycloalkyl, or $C_{3-7}$ cycloalkoxy,
 wherein each alkyl moiety of the alkyl and the alkoxy of $R^7$ and $R^8$ is optionally substituted with 1 to 3 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3substituents independently selected from Substituent-group B, and 3- to 7-membered non-aromatic heterocyclyl optionally-substituted with 1 to 3 substituents independently selected from Substituent-group B;
 wherein each cycloalkyl moiety of the cycloalkyl and the cycloalkoxy of $R^7$ and $R^8$ is optionally substituted with 1 to 3 substituents independently selected from the group consisting of halogen, hydroxyl, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, and $C_{3-7}$ cycloalkoxy optionally-substituted with 1 to 3 substituents independently selected from Substituent-group B; or
$R^2$ and $R^3$ may be combined together with the carbon atom to which they are attached to form the following group of formula (II) with —$OR^4$:

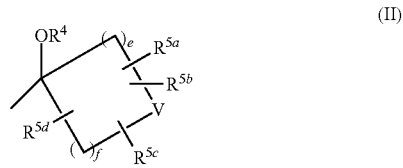

wherein:

e and f are each independently 1, 2 or 3;

V is single bond or oxygen atom;

$R^{5a}$, $R^{5b}$, $R^{5c}$, and $R^{5d}$ are each independently hydrogen, halogen, hydroxyl, $C_{1-4}$ alkyl, or $C_{1-4}$ alkoxy;

wherein each alkyl moiety of the alkyl and the alkoxy of $R^{5a}$, $R^{5b}$, $R^{5c}$, and $R^{5d}$ is optionally substituted with 1 to 3 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally substituted with 1 to 3 substituents independently selected from Substituent-group B; or in $R^2$, $R^3$, $-OR^4$ and $CR^7R^8$ of L, $R^2$ and $R^7$ may be combined together with the carbon atom to which they are attached to form the following group of formula (IV) with $R^3$, $-OR^4$ and $R^8$:

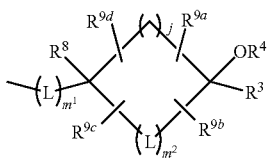

(IV)

wherein:

$m^1$ is 0 or 1; and $m^2$ is 0 or 1 and j is 1, 2, 3 or 4 when $m^1$ is 1; or $m^2$ is 0, 1 or 2 and j is 1, 2, 3 or 4 when $m^1$ is 0;

$R^{9a}$, $R^{9b}$, $R^{9c}$, and $R^{9d}$ are each independently hydrogen, halogen, hydroxyl, $C_{1-4}$ alkyl, or $C_{1-4}$ alkoxy;

wherein each alkyl moiety of the alkyl and the alkoxy of $R^{9a}$, $R^{9b}$, $R^{9c}$, and $R^{9d}$ is optionally substituted with 1 to 3 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally-substituted with 1 to 3 substituents independently selected from Substituent-group B; or $R^3$ and $-OR^4$ may be combined together with the carbon atom to which they are attached to form the following group of formula (III) with $R^2$:

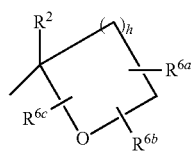

(III)

wherein:

h is 1, 2, 3, or 4; and $R^{6a}$, $R^{6b}$, and $R^{6c}$ are each independently hydrogen, halogen, hydroxyl, $C_{1-4}$ alkyl, or $C_{1-4}$ alkoxy;

wherein each alkyl moiety of the alkyl and the alkoxy of $R^{6a}$, $R^{6b}$, and $R^{6c}$ is optionally substituted with 1 to 3 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally-substituted with 1 to 3 substituents independently selected from Substituent-group B;

provided that all of $R^2$, $R^3$ and $-OR^4$ are not combined together to form a ring;

each Substituent-group A is independently halogen, hydroxyl, $C_{1-4}$ alkoxy, $C_{3-7}$ cycloalkyl, or $C_{3-7}$ cycloalkoxy; and each Substituent-group B is independently halogen, hydroxyl, $C_{1-4}$ alkyl, $C_{1-4}$ alkoxy, $C_{3-7}$ cycloalkyl, or $C_{3-7}$ cycloalkoxy;

provided that the following compounds are excluded from the compounds of Formula (I):

6-[6-chloro-2-(morpholin-4-yl)pyrimidin-4-yl]-1-(2-methoxyethyl)-1H-benzimidazole, 2-[5-(3,5-dimethyl-1,2-oxazol-4-yl)-1H-benzimidazol-1-yl]ethanol, 2-{5-[5-(tetrahydrofuran-3-yl)-4H-1,2,4-triazol-3-yl]-1H-benzimidazol-1-yl}ethanol, 2-{5-[3-(2-methoxyethyl)-1-(2,2,2-trifluoroethyl)-1H-1,2,4-triazol-5-yl]-1H-benzimidazol-1-yl}ethanol, 2-{5-[3-methyl-1-(1-methylpiperidin-4-yl)-1H-1,2,4-triazol-5-yl]-1H-benzimidazol-1-yl}ethanol, 2-butyl-6-[1-(2-hydroxyethyl)-1H-benzimidazol-6-yl]-3,4-dihydropyrrolo[1,2-a]pyrazin-1(2H)-one, 6-[1-(2-hydroxyethyl)-1H-benzimidazol-6-yl]-2-(3-methylbutyl)-3,4-dihydropyrrolo[1,2-a]pyrazin-1(2H)-one, 2-{5-[1-(2-hydroxyethyl)-1H-benzimidazol-5-yl]-1H-1,2,4-triazol-1-yl}ethanol, 6-(2-chlorophenyl)-1-(2-hydroxyethyl)-1H-benzimidazole-7-carbonitrile, 2-chloro-6-{7-fluoro-1-[(1S,3S)-3-methoxycyclohexyl]-1H-benzimidazol-5-yl}-9-(tetrahydro-2H-pyran-2-yl)-9H-purine, and 2-{5-[2-(tetrahydrofuran-3-yl)-1H-imidazol-1-yl]-1H-benzimidazol-1-yl}ethanol.

2. The compound of claim 1 or a pharmaceutically acceptable salt thereof, wherein:

$R^{1a}$, $R^{1b}$, $R^{1c}$, and $R^{1d}$ are each independently hydrogen, halogen, cyano, $C_{1-4}$ alkyl, $C_{1-4}$ alkoxy, $C_{6-10}$ aryl, $C_{6-10}$ aryloxy, 5- to 12-membered heteroaryl, or 5- to 12-membered heteroaryloxy;

wherein each alkyl moiety of the alkyl and the alkoxy of $R^{1a}$, $R^{1b}$, $R^{1c}$, and $R^{1d}$ is optionally substituted with 1 to 3 independently selected halogens;

wherein each aryl moiety of the aryl and the aryloxy and each heteroaryl moiety of the heteroaryl and the heteroaryloxy of $R^{1a}$, $R^{1b}$, $R^{1c}$, and $R^{1d}$ is optionally substituted with 1 to 3 substituents independently selected from the group consisting of halogen, cyano, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, and $C_{1-4}$ alkylsulfonyl optionally-substituted with 1 to 3 substituents independently selected from Substituent-group A.

3. The compound of claim 1, or a pharmaceutically acceptable salt thereof, wherein:
$R^{1a}, R^{1b}, R^{1c},$ and $R^{1d}$ are each independently hydrogen, $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy of $R^{1a}, R^{1b}, R^{1c},$ and $R^{1d}$ is optionally substituted with 1 to 3 substituents independently selected from the group consisting of halogen and $C_{1-4}$ alkyl optionally-substituted with 1 to 3 substituents independently selected from Substituent-group A.

4. The compound of claim 1, or a pharmaceutically acceptable salt thereof, wherein $R^{1a}$ and $R^{1d}$ are each hydrogen.

5. The compound of claim 1, or a pharmaceutically acceptable salt thereof, wherein:
$R^2$ and $R^3$ are each independently hydrogen or $C_{1-6}$ alkyl which may be independently substituted with 1 to 5 substituents independently selected from the group consisting of cyano, halogen, hydroxyl, and $C_{1-4}$ alkoxy optionally-substituted with 1 to 3 substituents independently selected from Substituent-group A, provided that both of $R^2$ and $R^3$ are not hydrogen; or
$R^2$ and $R^3$ may be combined together with the carbon atom to which they are attached to form the following group of formula (IIa) with —$OR^4$:

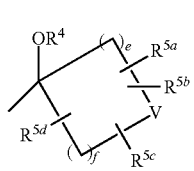

(IIa)

wherein:
e and f are each independently 1 or 2;
$R^{5a}, R^{5b}, R^{5c},$ and $R^{5d}$ are each independently hydrogen or halogen; or
in $R^2, R^3,$ —$OR^4$ and $CR^7R^8$ in L:
$R^2$ and $R^7$ may be combined together with the carbon atom to which they are attached to form the following group of formula (IVa) with $R^3$, —$OR^4$, and $R^8$:

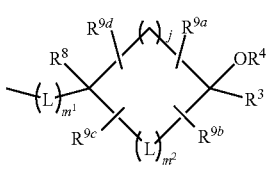

(IVa)

wherein
$m^1$ is 0;
$m^2$ is 1 or 2;
j is 1, 2 or 3;
$R^3$ is hydrogen or $C_{1-6}$ alkyl which may be independently substituted with 1 to 5 substituents independently selected from the group consisting of cyano, halogen, hydroxyl, and $C_{1-4}$ alkoxy optionally-substituted with 1 to 3 substituents independently selected from Substituent-group A;
and
$R^{9a}, R^{9b}, R^{9c},$ and $R^{9d}$ are each independently hydrogen or halogen.

6. The compound of claim 1, or a pharmaceutically acceptable salt thereof, wherein:
$R^2$ and $R^3$ are each independently $C_{1-6}$ alkyl optionally-substituted 1 to 5 independently selected halogens; or
$R^2$ and $R^3$ may be combined together with the carbon atom to which they are attached to form the following group of formula (IIb) with —$OR^4$:

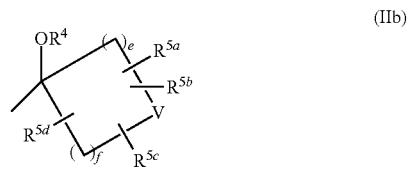

(IIb)

wherein:
e and f are each independently 1 or 2; and
$R^{5a}, R^{5b}, R^{5c},$ and $R^{5d}$ are each independently hydrogen or halogen; or
in $R^2, R^3,$ —$OR^4$ and $CR^7R^8$ in L:
$R^2$ and $R^7$ may be combined together with the carbon atom to which they are attached to form the following group of formula (IVa) with $R^3$, —$OR^4$ and $R^8$:

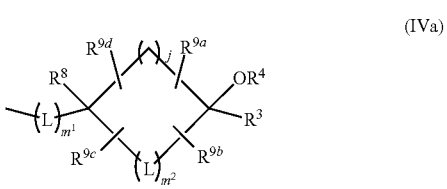

(IVa)

wherein:
$m^1$ is 0;
$m^2$ is 1 or 2;
j is 1, 2 or 3;
$R^4$ is hydrogen; and
$R^{9a}, R^{9b}, R^{9c},$ and $R^{9d}$ are each independently hydrogen or halogen.

7. The compound of claim 1, or a pharmaceutically acceptable salt thereof, wherein:
$R^2$ and $R^3$ are each independently hydrogen or $C_{1-6}$ alkyl optionally-substituted with 1 to 5 independently selected halogens.

8. The compound of claim 1, or a pharmaceutically acceptable salt thereof, wherein:
$R^4$ is hydrogen, $C_{1-4}$ alkyl optionally-substituted with 1 to 3 independently selected halogens, or $C_{3-7}$ cycloalkyl which is optionally substituted with 1 to 3 substituents independently selected from the group consisting of halogen, hydroxyl, and $C_{1-4}$ alkoxy optionally-substituted with 1 to 3 substituents independently selected from Substituent-group A; or
$R^3$ and —$OR^4$ may be combined together with the carbon atom to which they are attached to form the following group of formula (IIIa) with $R^2$:

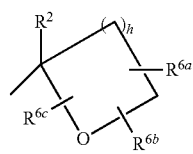

(IIIa)

wherein:
h is 1, 2, or 3;
$R^{6a}, R^{6b}$, and $R^{6c}$ are each independently hydrogen, halogen, or $C_{1-4}$ alkyl optionally-substituted with 1 to 3 independently selected halogens.

9. The compound of claim 1, or a pharmaceutically acceptable salt thereof, wherein:
$R^4$ is hydrogen, $C_{1-4}$ alkyl optionally-substituted with 1 to 3 independently selected halogens, or $C_{3-7}$ cycloalkyl which is optionally substituted with 1 to 3 substituents independently selected from the group consisting of halogen, hydroxyl, and $C_{1-4}$ alkoxy optionally-substituted with 1 to 3 substituents independently selected from Substituent-group A.

10. The compound of claim 1, or a pharmaceutically acceptable salt thereof, wherein $R^4$ is hydrogen.

11. The compound of claim 1, or a pharmaceutically acceptable salt thereof, wherein:
$R^7$ and $R^8$ are each independently hydrogen or $C_{1-4}$ alkyl which is optionally substituted with 1 to 3 substituents independently selected from the group consisting of halogen, hydroxyl, $C_{1-4}$ alkoxy optionally-substituted with 1 to 3 substituents independently selected from Substituent-group A, $C_{3-7}$ cycloalkyl optionally-substituted with 1 to 3 substituents independently selected from Substituent-group B, $C_{3-7}$ cycloalkoxy optionally-substituted with 1 to 3 substituents independently selected from Substituent-group B, and 3- to 7-membered non-aromatic heterocyclyl optionally-substituted with 1 to 3 substituents independently selected from Substituent-group B, and
m is 1 or 2.

12. The compound of claim 1, or a pharmaceutically acceptable salt thereof, wherein $R^7$ and $R^8$ are each hydrogen, and m is 1.

13. The compound of claim 1, or a pharmaceutically acceptable salt thereof, wherein:
$R^{1b}$ or $R^{1c}$ is $C_{6-10}$ aryl, $C_{6-10}$ aryloxy, 5- to 12-membered heteroaryl, or 5- to 12-membered heteroaryloxy;
wherein each aryl moiety of the aryl and the aryloxy and each heteroaryl moiety of the heteroaryl and the heteroaryloxy of $R^{1b}$ and $R^{1c}$ is optionally substituted with 1 to 3 substituents independently selected from the group consisting of halogen, cyano, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, and $C_{1-4}$ alkylsulfonyl optionally-substituted with 1 to 3 substituents independently selected from Substituent-group A.

14. The compound of claim 1, or a pharmaceutically acceptable salt thereof, wherein:
$R^{1b}$ is $C_{6-10}$ aryl, $C_{6-10}$ aryloxy, 5- to 12-membered heteroaryl, or 5- to 12-membered heteroaryloxy;
wherein each aryl moiety of the aryl and the aryloxy and each heteroaryl moiety of the heteroaryl and the heteroaryloxy of $R^{1b}$ is optionally substituted with 1 to 3 substituents independently selected from the group consisting of halogen, cyano, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, and $C_{1-4}$ alkylsulfonyl optionally-substituted with 1 to 3 substituents independently selected from Substituent-group A.

15. The compound of claim 1, or a pharmaceutically acceptable salt thereof, wherein:
$R^{1c}$ is $C_{6-10}$ aryl, $C_{6-10}$ aryloxy, 5- to 12-membered heteroaryl, or 5- to 12-membered heteroaryloxy;
wherein each aryl moiety of the aryl and the aryloxy and each heteroaryl moiety of the heteroaryl and the heteroaryloxy of $R^{1c}$ is optionally substituted with 1 to 3 substituents independently selected from the group consisting of halogen, cyano, $C_{1-4}$ alkyl optionally-substituted with 1 to 3 substituents independently selected from Substituent-group A, $C_{1-4}$ alkoxy optionally-substituted with 1 to 3 substituents independently selected from Substituent-group A, and $C_{1-4}$ alkylsulfonyl optionally-substituted with 1 to 3 substituents independently selected from Substituent-group A.

16. The compound of claim 1, or a pharmaceutically acceptable salt thereof, which is selected from the group of compounds consisting of:
1-[6-(4-fluorophenoxy)-1H-benzimidazol-1-yl]-2-methylpropan-2-ol,
6-(4-fluorophenoxy)-1-(tetrahydrofuran-2-ylmethyl)-1H-benzimidazole,
1-(tetrahydrofuran-2-ylmethyl)-6-[4-(trifluoromethyl)phenyl]-1H-benzimidazole,
2-methyl-1-{6-[4-(trifluoromethyl)phenyl]-1H-benzimidazol-1-yl}propan-2-ol,
1-[2-(cyclopentyloxy)ethyl]-6-[4-(trifluoromethyl)phenyl]-1H-benzimidazole,
2-methyl-1-{6-[5-(trifluoromethyl)pyridin-2-yl]-1H-benzimidazol-1-yl}propan-2-ol,
1-[2-(cyclopentyloxy)ethyl]-6-[5-(trifluoromethyl)pyridin-2-yl]-1H-benzimidazole,
2-methyl-1-[6-(4-methylphenoxy)-1H-benzimidazol-1-yl]propan-2-ol,
2-methyl-1-{6-[4-(trifluoromethyl)phenoxy]-1H-benzimidazol-1-yl}propan-2-ol,
1-[6-(4-chlorophenoxy)-1H-benzimidazol-1-yl]-2-methylpropan-2-ol,
2-methyl-1-{6-[4-(trifluoromethoxy)phenoxy]-1H-benzimidazol-1-yl}propan-2-ol,
2-methyl-1-{6-[(6-methylpyridin-3-yl)oxy]-1H-benzimidazol-1-yl}propan-2-ol,
2-methyl-1-(6-{[6-(trifluoromethyl)pyridin-3-yl]oxy}-1H-benzimidazol-1-yl)propan-2-ol,
2-methyl-1-(6-{[5-(trifluoromethyl)pyridin-2-yl]oxy}-1H-benzimidazol-1-yl)propan-2-ol,
2-methyl-1-(5-{[5-(trifluoromethyl)pyrazin-2-yl]oxy}-1H-benzimidazol-1-yl)propan-2-ol,
2-methyl-1-(5-{[5-(trifluoromethyl)pyrimidin-2-yl]oxy}-1H-benzimidazol-1-yl)propan-2-ol,
1-(5-{[3-fluoro-5-(trifluoromethyl)pyridin-2-yl]oxy}-1H-benzimidazol-1-yl)-2-methylpropan-2-ol,
1-{5-[(5-chloro-3-fluoropyridin-2-yl)oxy]-1H-benzimidazol-1-yl}-2-methylpropan-2-ol,
3-[(6-{[5-(trifluoromethyl)pyridin-2-yl]oxy}-1H-benzimidazol-1-yl)methyl]oxetan-3-ol,
1-[(6-{[5-(trifluoromethyl)pyridin-2-yl]oxy}-1H-benzimidazol-1-yl)methyl]cyclobutanol,
2-methyl-4-(6-{[5-(trifluoromethyl)pyridin-2-yl]oxy}-1H-benzimidazol-1-yl)butan-2-ol, 2-methyl-1-(6-{[5-(2,2,2-trifluoroethyl)pyridin-2-yl]oxy}-1H-benzimidazol-1-yl)propan-2-ol,
3-({6-[4-(trifluoromethyl)phenoxy]-1H-benzimidazol-1-yl}methy)oxetan-3-ol,
3-({6-[4-(trifluoromethoxy)phenoxy]-1H-benzimidazol-1-yl}methyl)oxetan-3-ol,
4-[6-(4-chlorophenoxy)-1H-benzimidazol-1-yl]-2-methylbutan-2-ol,
3-{[6-(2-chloro-4-fluorophenoxy)-1H-benzimidazol-1-yl]methyl}oxetan-3-ol,
cis-4-(6-{[5-(trifluoromethyl)pyridin-2-yl]oxy}-1H-benzimidazol-1-yl)cyclohexanol,
1-{6-[2-fluoro-4-(trifluoromethyl)phenyl]-1H-benzimidazol-1-yl}-2-methylpropan-2-ol,
1-[6-(4-chloro-2-fluorophenyl)-1H-benzimidazol-1-yl]-2-methylpropan-2-ol,
3-({6-[2-methoxy-4-(trifluoromethyl)phenyl]-1H-benzimidazol-1-yl}methyl)oxetan-3-ol,
4-{6-[2-methoxy-4-(trifluoromethyl)phenyl]-1H-benzimidazol-1-yl }-2-methylbutan-2-ol,
1-{5-[2-methoxy-4-(trifluoromethyl)phenyl]-1H-benzimidazol-1-yl}-2-methylpropan-2-ol,
2-methyl-1-{5-[4-(trifluoromethoxy)phenyl]-1H-benzimidazol-1-yl}propan-2-ol,
1-{5-[2-fluoro-4-(trifluoromethyl)phenyl]-1H-benzimidazol-1-yl}-2-methylpropan-2-ol,
3-({5-[2-methoxy-4-(trifluoromethyl)phenyl]-1H-benzimidazol-1-yl}methyl)oxetan-3-ol, and
(3S)-2-methyl-3-(6-{[5-(trifluoromethyl)pyridin-2-yl]oxy}-1H-benzimidazol-1-yl)butan-2-ol.

17. The compound of claim 1, or a pharmaceutically acceptable salt thereof, which is selected from the group of compounds consisting of:
1-[6-(4-fluorophenoxy)-1H-benzimidazol-1-yl]-2-methylpropan-2-ol,
2-methyl-1-{6-[4-(trifluoromethyl)phenyl]-1H-benzimidazol-1-yl}propan-2-ol,
2-methyl-1-{6-[5-(trifluoromethyl)pyridin-2-yl]-1H-benzimidazol-1-yl}propan-2-ol,
2-methyl-1-{6-[4-(trifluoromethyl)phenoxy]-1H-benzimidazol-1-yl}propan-2-ol,
1-[6-(4-chlorophenoxy)-1H-benzimidazol-1-yl]-2-methylpropan-2-ol,
2-methyl-1-{6-[4-(trifluoromethoxy)phenoxy]-1H-benzimidazol-1-yl}propan-2-ol,
2-methyl-1-{6-[(6-methylpyridin-3-yl)oxy]-1H-benzimidazol-1-yl}propan-2-ol,
2-methyl-1-(6-{[5-(trifluoromethyl)pyridin-2-yl]oxy}-1H-benzimidazol-1-yl)propan-2-ol,
2-methyl-1-(5-{[5-(trifluoromethyl)pyrazin-2-yl]oxy}-1H-benzimidazol-1-yl)propan-2-ol,
1-(5-{[3-fluoro-5-(trifluoromethyl)pyridin-2-yl]oxy}-1H-benzimidazol-1-yl)-2-methylpropan-2-ol,
2-methyl-4-(6-{[5-(trifluoromethyl)pyridin-2-yl]oxy}-1H-benzimidazol-1-yl)butan-2-ol,
2-methyl-1-(6-{[5-(2,2,2-trifluoroethyl)pyridin-2-yl]oxy}-1H-benzimidazol-1-yl)propan-2-ol,
3-({6-[4-(trifluoromethoxy)phenoxy]-1H-benzimidazol-1-yl}methyl)oxetan-3-ol,
4-[6-(4-chlorophenoxy)-1H-benzimidazol-1-yl]-2-methylbutan-2-ol,
cis-4-(6-{[5-(trifluoromethyl)pyridin-2-yl]oxy}-1H-benzimidazol-1-yl)cyclohexanol,
1-{6-[2-fluoro-4-(trifluoromethyl)phenyl]-1H-benzimidazol-1-yl}-2-methylpropan-2-ol,
3-({6-[2-methoxy-4-(trifluoromethyl)phenyl]-1H-benzimidazol-1-yl}methyl)oxetan-3-ol,
3-({5-[2-methoxy-4-(trifluoromethyl)phenyl]-1H-benzimidazol-1-yl}methyl)oxetan-3-ol, and
(3S)-2-methyl-3-(6-{[5-(trifluoromethyl)pyridin-2-yl]oxy}-1H-benzimidazol-1-yl)butan-2-ol.

18. A pharmaceutical composition comprising the compound of claim 1, or a pharmaceutically acceptable salt thereof, and a pharmaceutically acceptable additive agent.

19. A method of treating a disease involving NAV1.7 (SCN9A) in a subject, comprising administering to the subject the compound of claim 1, or a pharmaceutically acceptable salt thereof, as an active ingredient.

20. A pharmaceutical combination comprising the compound of claim 1, or a pharmaceutically acceptable salt thereof, and at least one drug selected from the group consisting of an antiepileptic agent, an antidepressive agent, a narcotic analgesic, an anti-inflammatory agent, a reductase inhibitor, and a prostaglandin derivative drug.

21. A method of treating neuropathic pain, nociceptive pain, inflammatory pain, small-fiber neuropathy, erythromelalgia, paroxysmal extreme pain disorder, dysuria, or multiple sclerosis in a mammal in need thereof, which comprises administering a therapeutically effective amount of the compound of claim 1, or a pharmaceutically acceptable salt thereof, to the mammal.

22. The method of claim 21, further comprising administering a therapeutically effective amount of at least one drug selected from the group consisting of an antiepileptic agent, an antidepressive agent, a narcotic analgesic, an anti-inflammatory agent, a reductase inhibitor, and a prostaglandin derivative drug.

23. The method of claim 21, further comprising administering a therapeutically effective amount of a narcotic analgesic.

24. The method of claim 23, wherein the narcotic analgesic is morphine, oxycodone, or tramadol.

25. A pharmaceutical combination comprising the compound of claim 1, or a pharmaceutically acceptable salt thereof, and a narcotic analgesic.

26. The pharmaceutical combination of claim 25, wherein the narcotic analgesic is morphine, oxycodone, or tramadol.

27. The compound of claim 1, or a pharmaceutically acceptable salt thereof, wherein $R^{1a}$ and $R^{1d}$ are hydrogen, at least one of $R^{1b}$ and $R^{1c}$ is $C_{6-10}$ aryl, $C_{6-10}$ aryloxy, 5- to 12-membered heteroaryl, or 5- to 12-membered heteroaryloxy, wherein each aryl moiety of the aryl and the aryloxy and each heteroaryl moiety of the heteroaryl and the heteroaryloxy may be independently substituted with 1 to 3 substituents selected independently from the group consisting of halogen and $C_{1-4}$ alkyl optionally-substituted with 1 to 3 substituents selected independently from Substituent-group A,
$R^2$ and $R^3$ are independently $C_{1-6}$ alkyl optionally-substituted with the same or different and 1 to 5 halogens, or $R^2$ and $R^3$ may be combined together with the carbon atom to which they are attached to form the following group of formula (IIb) with —$OR^4$

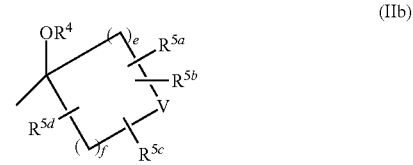

in formula (IIb),
e and f are independently 1 or 2,
$R^4$ is hydrogen, $C_{1-6}$ alkyl which may be substituted with 1 to 3 substituents selected independently from the group consisting of halogen, hydroxyl, $C_{1-4}$ alkoxy optionally-substituted with 1 to 3 substituents selected independently from Substituent-group A, $C_{3-7}$ cycloalkyl optionally-substituted with 1 to 3 substituents selected independently from Substituent-group B, $C_{3-7}$ cycloalkoxy optionally-substituted with 1 to 3 substituents selected independently from Substituent-group B, and 3- to 7-membered non-aromatic heterocyclyl optionally-substituted with 1 to 3 substituents selected independently from Substituent-group B, or $C_{3-7}$ cycloalkyl which may be independently substituted with 1 to 3 substituents selected independently from the group consisting of halogen, hydroxyl, $C_{1-4}$ alkyl optionally-substituted with 1 to 3 substituents selected independently from Substituent-group A, $C_{1-4}$ alkoxy optionally-substituted with 1 to 3 substituents selected independently from Substituent-group A, C3-7cycloalkyl optionally-substituted with 1 to 3 substituents selected independently from Substituent-group B, and $C_{3-7}$ cycloalkoxy optionally-substituted with 1 to 3 substituents selected independently from Substituent-group B, V is single bond or oxygen atom, $R^{5a}$, $R^{5b}$, $R^{5c}$, and $R^{5d}$ are independently hydrogen or halogen, or in $R^2$, $R^3$, —$OR^4$ and $CR^7R^8$ in L, $R^2$ and $R^7$ may be combined together with the carbon atom to which they are attached to form the following group of formula (IVa) with $R^3$, —$OR^4$ and $R^8$

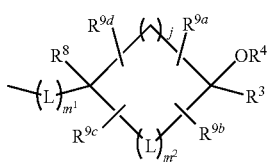
(IVa)

in formula (IVa), $m^1$ is 0, $m^2$ is 1 or 2, j is 1 or 2, $R^3$ is hydrogen or $C_{1-4}$ alkyl, $R^4$ is hydrogen, $R^8$ is hydrogen or $C_{1-4}$ alkyl, L is $CR^7R^8$, provided that when m is 2, each $CR^7R^8$ are independently the same or different, $R^{9a}$, $R^{9b}$, $R^{9c}$, and $R^{9d}$ are independently hydrogen or halogen, $R^4$ is hydrogen, $C_{1-4}$ alkyl optionally-substituted with the same or different and 1 to 3 halogens, or $C_{3-7}$ cycloalkyl optionally-substituted with the same or different and 1 to 3 halogens, or $R^3$ and —$OR^4$ may be combined together with the carbon atom to which they are attached to form the following group of formula (IIIa) with $R^2$

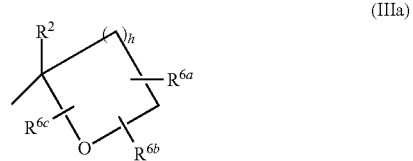
(IIIa)

in formula (IIIa), h is 1, 2 or 3, $R^2$ is hydrogen or $C_{1-4}$ alkyl optionally-substituted with the same or different and 1 to 3 halogens, $R^{6a}$, $R^{6b}$, and $R^{6c}$ are independently hydrogen, halogen, or $C_{1-4}$ alkyl optionally-substituted with the same or different and 1 to 3 halogens, m is 1 or 2, L is $CR^7R^8$, provided that when m is 2, each $CR^7R^8$ are independently the same or different, $R^7$ and $R^8$ are independently hydrogen or $C_{1-4}$ alkyl optionally-substituted with the same or different and 1 to 3 halogens.

\* \* \* \* \*

UNITED STATES PATENT AND TRADEMARK OFFICE
CERTIFICATE OF CORRECTION

PATENT NO. : 10,407,395 B2
APPLICATION NO. : 15/323185
DATED : September 10, 2019
INVENTOR(S) : Masafumi Komiya et al.

It is certified that error appears in the above-identified patent and that said Letters Patent is hereby corrected as shown below:

In the Specification

Column 1, Line 9, After "2016," delete "which published as WO2014/054635, and";

In the Claims

Column 124, Lines 55-65, Claim 1, delete " 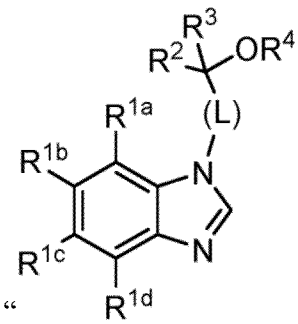 " and insert

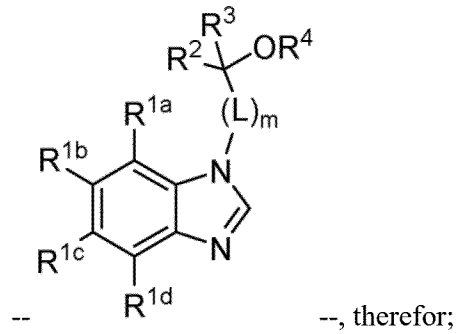 --, therefor;

Column 125, Line 9, Claim 1, delete "R1b,R1c,and" and insert -- R1b, R1c, and --, therefor;

Column 125, Line 23, Claim 1, delete "R1c,and" and insert -- R1c, and --, therefor;

Signed and Sealed this
Second Day of March, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,407,395 B2

Column 126, Line 6, Claim 1, delete "C1-4alkoxy" and insert -- C1-4 alkoxy --, therefor;

Column 126, Line 37, Claim 1, delete "3substituents" and insert -- 3 substituents --, therefor;

Column 127, Line 4 (Approx.), Claim 1, delete "R 5b, R5c,and" and insert -- R5b, R5c, and --, therefor;

Column 128, Line 3, Claim 1, delete "R6a ," and insert -- R6a, --, therefor;

Column 128, Line 33, Claim 1, delete "-yl }" and insert -- -yl} --, therefor;

Column 128, Line 52, Claim 2, delete "R1b,R1c,and" and insert -- R1b, R1c, and --, therefor;

Column 128, Line 57, Claim 2, delete "R1b,R1c," and insert -- R1b, R1c, --, therefor;

Column 128, Line 61, Claim 2, delete "R1a,R1b,R1c," and insert -- R1a, R1b, R1c, --, therefor;

Column 129, Line 6, Claim 3, delete "R1a,R1b,R1c ,and" and insert -- R1a, R1b, R1c, and --, therefor;

Column 131, Line 12, Claim 8, delete "R6a,R6b," and insert -- R6a, R6b, --, therefor;

Column 131, Line 63, Claim 14, delete "5 -" and insert -- 5- --, therefor;

Column 132, Line 33, Claim 16, delete "-yl }" and insert -- -yl} --, therefor;

Column 133, Line 4, Claim 16, delete "yl}methy)" and insert -- yl}methyl) --, therefor;

Column 133, Line 20, Claim 16, delete "-yl }" and insert -- -yl} --, therefor;

Column 134, Line 53, Claim 27, delete "(IIb)" and insert -- (IIb) --, therefor;

Column 135, Line 16, Claim 27, delete "C3-7cycloalkyl" and insert -- C3-7 cycloalkyl --, therefor.